US012799469B2

(12) United States Patent
Henrich et al.

(10) Patent No.: US 12,799,469 B2
(45) Date of Patent: Nov. 17, 2026

(54) COMPOSITIONS AND METHODS FOR TREATING CANCER

(71) Applicant: THE CHILDREN'S HOSPITAL OF PHILADELPHIA, Philadelphia, PA (US)

(72) Inventors: Ian Henrich, Philadelphia, PA (US); Margaret M. Chou, Bala Cynwyd, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 1096 days.

(21) Appl. No.: 17/296,722

(22) PCT Filed: Nov. 27, 2019

(86) PCT No.: PCT/US2019/063594
§ 371 (c)(1),
(2) Date: May 25, 2021

(87) PCT Pub. No.: WO2020/112991
PCT Pub. Date: Jun. 4, 2020

(65) Prior Publication Data

US 2022/0025349 A1 Jan. 27, 2022

Related U.S. Application Data

(60) Provisional application No. 62/893,492, filed on Aug. 29, 2019, provisional application No. 62/796,959, filed on Jan. 25, 2019, provisional application No. 62/771,869, filed on Nov. 27, 2018.

(51) Int. Cl.

| | |
|---|---|
| ***A61K 48/00*** | (2006.01) |
| ***A61K 38/21*** | (2006.01) |
| ***A61K 38/48*** | (2006.01) |
| ***A61P 35/02*** | (2006.01) |
| ***C12N 9/22*** | (2006.01) |
| ***C12N 9/48*** | (2006.01) |
| ***C12N 15/11*** | (2006.01) |

(52) U.S. Cl.
CPC ............ *C12N 9/485* (2013.01); *A61K 38/215* (2013.01); *A61K 38/4813* (2013.01); *A61P 35/02* (2018.01); *C12N 9/222* (2025.05); *C12Y 304/19012* (2013.01)

(58) Field of Classification Search
None
See application file for complete search history.

(56) References Cited

U.S. PATENT DOCUMENTS

2012/0164642 A1* 6/2012 Erickson-Johnson ...................... C12Q 1/6883 435/6.11
2017/0258915 A1 9/2017 de Fougerolles et al.
2018/0326012 A1 11/2018 Wei

FOREIGN PATENT DOCUMENTS

WO 2017/191274 A2 11/2017

OTHER PUBLICATIONS

Huang et al, The landscape of mRNA nanomedicine, Nature Medicine, 2022, pp. 2273-2287.*
Mak et al, Lost in translation: animal models and clinical trials in cancer treatment, Am J Transl Res 2014;6(2):114-118.*
Jain et al, Natural Killer Cell Activation by updates Ubiquitin-specific Protease 6 Mediates Tumor Suppression in Ewing Sarcoma, Cancer Res Commun; 3(8) Aug. 2023, p. 1615-1627.*
Li et al, Intratumoral injection of mRNA encoding survivin in combination with STAT3 inhibitor stattic enhances antitumor effects, Cancer Letters, 2024, pp. 1-12.*
Syed et al, Physiological roles and therapeutic implications of USP6, Cell Death Dicsovery, 2025, pp. 1-13.*
Islam, et al., "Biomaterials for mRNA delivery" Biomater. Sci. (201) 3:1519-1533.
Avci-Adali, et al., "In vitro synthesis of modified mRNA for induction of protein expression in human cells" J. Vis. Exp. (2014) 93:e51943.
Henrich, et al., "P211: Ubiquitin-specific protease 6 (USP6) oncogene confers dramatic sensitivity of sarcoma cells to the immunostimulatory effects of interferon" Journal for ImmunoTherapy of Cancer (2016) 4(Suppl 1):73, pp. 118-120.
Henrich, et al., "P462: Ubiquitin-specific protease 6 (USP6) oncogene promotes immune cell recruitment in sarcoma" Journal for ImmunoTherapy of Cancer (2017) 5(Suppl 2):87, pp. 223-224.
Henrich, et al., "USP6 Confers Sensitivity to IFN-Mediated Apoptosis through Modulation of TRAIL Signaling in Ewing Sarcoma" Mol. Cancer Res. (2018) 16(12):1834-1843.
Henrich, et al., "Ubiquitin-specific protease 6 (USP6) oncogene confers sensitivity of Ewing sarcoma to interferon cytotoxicity [abstract]" In: Proceedings of the AACR Conference on Advances in Sarcomas: From Basic Science to Clinical Translation; May 16-19, 2017; Philadelphia, PA. Philadelphia (PA): AACR; Clin. Cancer Res. (2018) 24 (2_Suppl): Abstract nr PR08.
Masuda-Robens, et al., "The TRE17 oncogene encodes a component of a novel effector pathway for Rho GTPases Cdc42 and Rac1 and stimulates actin remodeling" Mol. Cell Biol. (2003) 23(6):2151-61.

(Continued)

*Primary Examiner* — Maria Marvich
(74) *Attorney, Agent, or Firm* — Robert C. Netter, Jr.; Dann, Dorfman, Herrell & Skillman

(57) ABSTRACT

Compositions and methods for treating cancer are provided. In accordance with the instant invention, methods of inhibiting or treating cancer, particularly a "cold" cancer or a cancer lacking CD8+ tumor infiltrating lymphocytes (TILs) and/or other immunostimulatory features, in a subject are provided. In a particular embodiment, the method comprises administering an agent which increases ubiquitin-specific protease 6 (USP6) activity and/or expression to the subject.

20 Claims, 36 Drawing Sheets

Specification includes a Sequence Listing.

(56) References Cited

OTHER PUBLICATIONS

Madan, et al., "USP6 oncogene promotes Wnt signaling by deubiquitylating Frizzleds" Proc. Natl. Acad. Sci. (2016) 113:E2945-E2954.

Quick, et al., "Jak1-STAT3 Signals Are Essential Effectors of the USP6/TRE17 Oncogene in Tumorigenesis" Cancer Res. (2016) 76(18):5337-47.

Henrich, et al., "Abstract P030: Making cold tumors hot: Multi-faceted immune ignition by USP6" Cancer Immunol. Res. (2022) 10 (1_Supplement):P030.

Bannas, et al., "Nanobodies and Nanobody-Based Human Heavy Chain Antibodies as Antitumor Therapeutics" Front. Immunol. (2017) 8:1603.

Steinle, et al., "Concise Review: Application of In Vitro Transcribed Messenger RNA for Cellular Engineering and Reprogramming: Progress and Challenges" Stem Cells (2017) 35:68-79.

Sahin, et al., "mRNA-based therapeutics—developing a new class of drugs" Nat. Rev. Drug Discov. (2014) 13 (10):759-80.

Oliveira, et al., "Aneurysmal bone cyst variant translocations upregulate USP6 transcription by promoter swapping with the ZNF9, COL1A1, TRAP150, and OMD genes" Oncogene (2005) 24(21):3419-26.

Oliveira, et al., "USP6-induced neoplasms: the biologic spectrum of aneurysmal bone cyst and nodular fasciitis" Hum. Pathol. (2014) 45(1):1-11.

Henrich, et al., "Ubiquitin-Specific Protease 6 Functions as a Tumor Suppressor in Ewing Sarcoma through Immune Activation" Cancer Res. (2021) 81(8):2171-2183.

Henrich, et al., "Ubiquitin-specific protease 6 (USP6) mRNA lipid nanoparticles ignite anti-tumor immunity and suppress tumorigenesis in Ewing sarcoma" Mol Cancer Ther. (2025) 10.1158/1535-7163.MCT-24-0173.

* cited by examiner

GSE7007 Primary Ewing Sarcoma:
USP6 $^{high}$ vs. USP6 $^{low}$

| Gene Set | FDR | # Genes | NES |
|---|---|---|---|
| HALLMARK_INTERFERON_ALPHA_RESPONSE | 0.065 | 77 | 1.36 |
| HALLMARK_INTERFERON_GAMMA_RESPONSE | 0.053 | 171 | 1.35 |
| HALLMARK_IL6_JAK_STAT3_SIGNALING | 0.060 | 85 | 1.35 |

GSE37371 (U133A) Primary Ewing Sarcoma:
USP6 $^{high}$ vs. USP6 $^{low}$

| Gene Set | FDR | # Genes | NES |
|---|---|---|---|
| HALLMARK_INTERFERON_ALPHA_RESPONSE | 0.003 | 77 | 1.88 |
| HALLMARK_INTERFERON_GAMMA_RESPONSE | 0.034 | 171 | 1.60 |
| HALLMARK_IL6_JAK_STAT3_SIGNALING | 0.225 | 85 | 1.20 |

RNA-seq: USP6/RD-ES +Dox vs. –Dox

| Gene Set | FDR | # Genes | NES |
|---|---|---|---|
| HALLMARK_INTERFERON_ALPHA_RESPONSE | <0.001 | 87 | 2.36 |
| HALLMARK_INTERFERON_GAMMA_RESPONSE | <0.001 | 182 | 2.38 |
| HALLMARK_IL6_JAK_STAT3_SIGNALING | <0.001 | 84 | 2.03 |

GSE78991 Nodular Fasciitis vs. Other mesenchymal tumors

| Gene Set | FDR | # Genes | NES |
|---|---|---|---|
| HALLMARK_INTERFERON_ALPHA_RESPONSE | <0.001 | 96 | 2.79 |
| HALLMARK_INTERFERON_GAMMA_RESPONSE | <0.001 | 199 | 2.73 |

GSE10615 Germ cell tumors:
Seminoma (USP6 $^{high}$) vs. Yolk Sac Tumor (USP6 $^{low}$)

| Gene Set | FDR | # Genes | NES |
|---|---|---|---|
| HALLMARK_INTERFERON_ALPHA_RESPONSE | <0.001 | 77 | 2.01 |
| HALLMARK_INTERFERON_GAMMA_RESPONSE | <0.001 | 171 | 2.40 |
| HALLMARK_IL6_JAK_STAT3_SIGNALING | 0.014 | 85 | 1.52 |

FIG. 1A

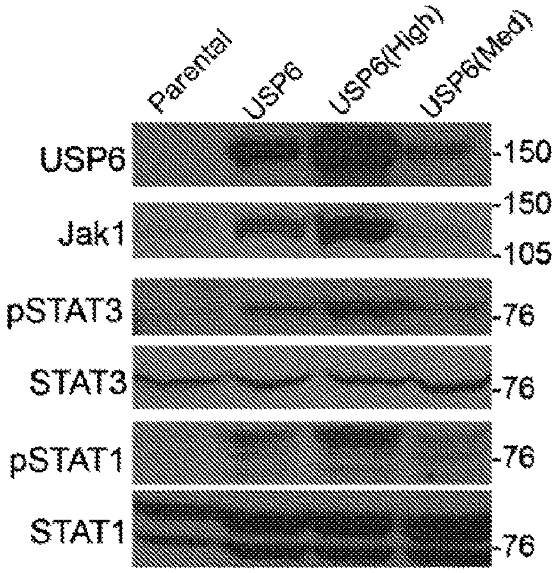

FIG. 1B

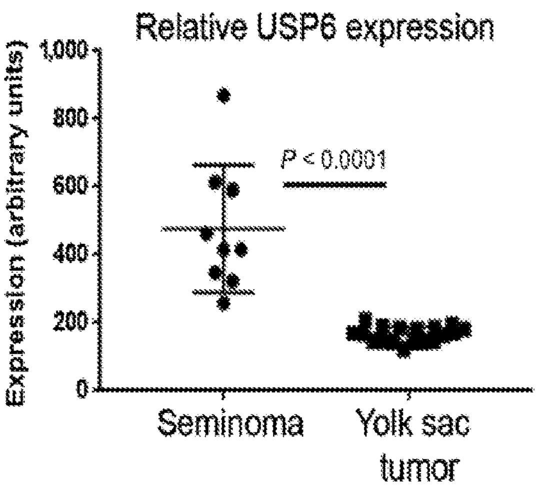

FIG. 1C

THP-1
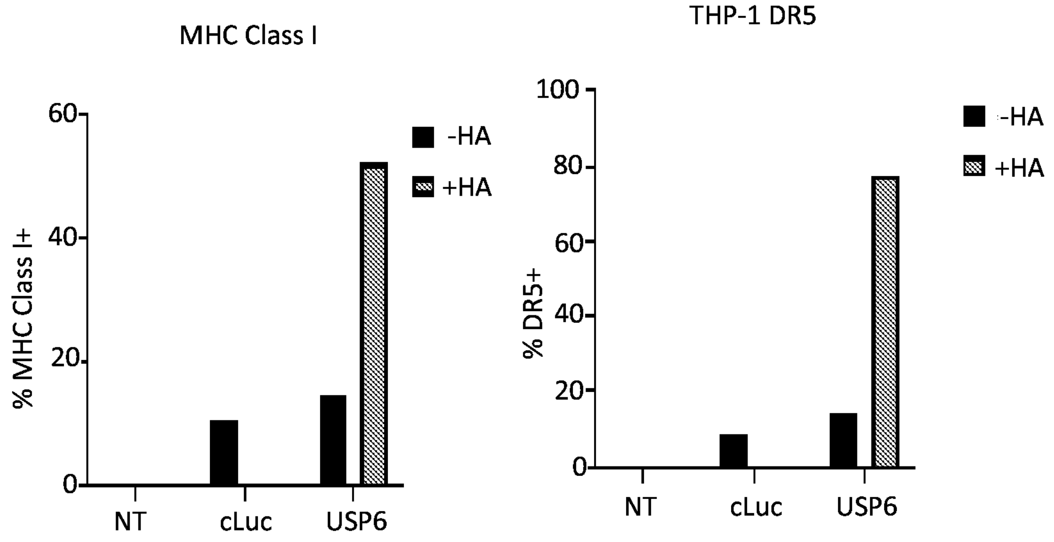
U937
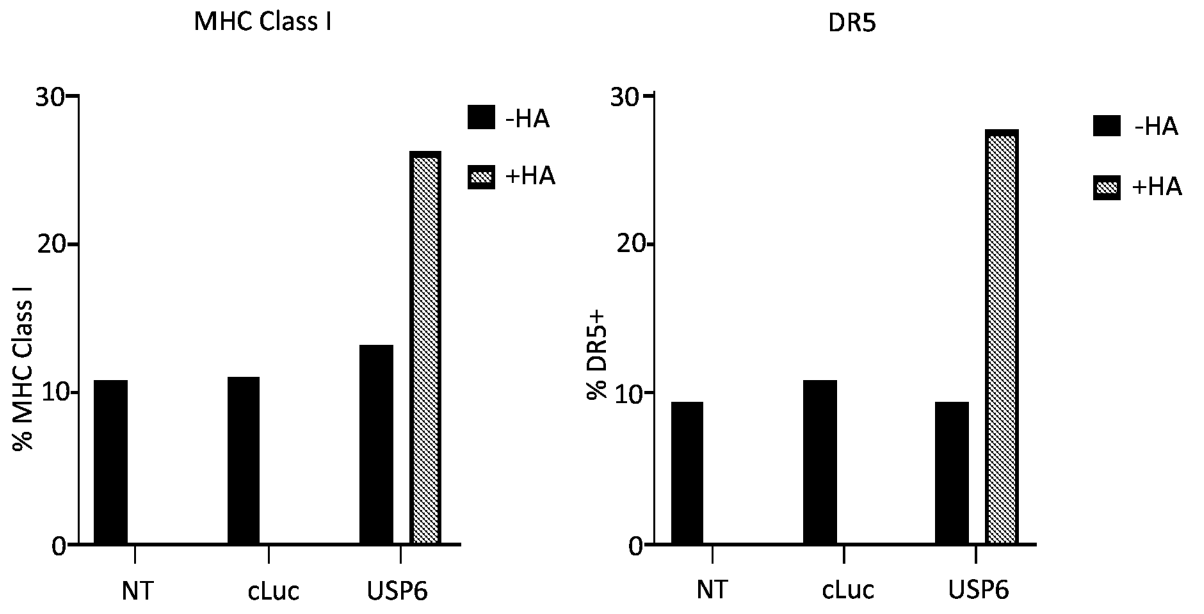
FIG. 16B

SEQUENCE LISTING

```
<160> NUMBER OF SEQ ID NOS: 7

<210> SEQ ID NO 1
<211> LENGTH: 1406
<212> TYPE: PRT
<213> ORGANISM: Homo sapiens

<400> SEQUENCE: 1

Met Asp Met Val Glu Asn Ala Asp Ser Leu Gln Ala Gln Glu Arg Lys
1               5                   10                  15

Asp Ile Leu Met Lys Tyr Asp Lys Gly His Arg Ala Gly Leu Pro Glu
            20                  25                  30

Asp Lys Gly Pro Glu Pro Val Gly Ile Asn Ser Ser Ile Asp Arg Phe
        35                  40                  45

Gly Ile Leu His Glu Thr Glu Leu Pro Pro Val Thr Ala Arg Glu Ala
    50                  55                  60

Lys Lys Ile Arg Arg Glu Met Thr Arg Thr Ser Lys Trp Met Glu Met
65                  70                  75                  80
```

```
Leu Gly Glu Trp Glu Thr Tyr Lys His Ser Ser Lys Leu Ile Asp Arg
                85                  90                  95

Val Tyr Lys Gly Ile Pro Met Asn Ile Arg Gly Pro Val Trp Ser Val
            100                 105                 110

Leu Leu Asn Ile Gln Glu Ile Lys Leu Lys Asn Pro Gly Arg Tyr Gln
        115                 120                 125

Ile Met Lys Glu Arg Gly Lys Arg Ser Ser Glu His Ile His His Ile
    130                 135                 140

Asp Leu Asp Val Arg Thr Thr Leu Arg Asn His Val Phe Phe Arg Asp
145                 150                 155                 160

Arg Tyr Gly Ala Lys Gln Arg Glu Leu Phe Tyr Ile Leu Leu Ala Tyr
                165                 170                 175

Ser Glu Tyr Asn Pro Glu Val Gly Tyr Cys Arg Asp Leu Ser His Ile
            180                 185                 190

Thr Ala Leu Phe Leu Leu Tyr Leu Pro Glu Glu Asp Ala Phe Trp Ala
        195                 200                 205

Leu Val Gln Leu Leu Ala Ser Glu Arg His Ser Leu Pro Gly Phe His
    210                 215                 220

Ser Pro Asn Gly Gly Thr Val Gln Gly Leu Gln Asp Gln Gln Glu His
225                 230                 235                 240

Val Val Pro Lys Ser Gln Pro Lys Thr Met Trp His Gln Asp Lys Glu
                245                 250                 255

Gly Leu Cys Gly Gln Cys Ala Ser Leu Gly Cys Leu Leu Arg Asn Leu
            260                 265                 270

Ile Asp Gly Ile Ser Leu Gly Leu Thr Leu Arg Leu Trp Asp Val Tyr
        275                 280                 285

Leu Val Glu Gly Glu Gln Val Leu Met Pro Ile Thr Ser Ile Ala Leu
    290                 295                 300

Lys Val Gln Gln Lys Arg Leu Met Lys Thr Ser Arg Cys Gly Leu Trp
305                 310                 315                 320

Ala Arg Leu Arg Asn Gln Phe Phe Asp Thr Trp Ala Met Asn Asp Asp
                325                 330                 335

Thr Val Leu Lys His Leu Arg Ala Ser Thr Lys Lys Leu Thr Arg Lys
            340                 345                 350

Gln Gly Asp Leu Pro Pro Pro Ala Lys Arg Glu Gln Gly Ser Leu Ala
        355                 360                 365

Pro Arg Pro Val Pro Ala Ser Arg Gly Gly Lys Thr Leu Cys Lys Gly
    370                 375                 380

Tyr Arg Gln Ala Pro Pro Gly Pro Pro Ala Gln Phe Gln Arg Pro Ile
385                 390                 395                 400

Cys Ser Ala Ser Pro Pro Trp Ala Ser Arg Phe Ser Thr Pro Cys Pro
                405                 410                 415

Gly Gly Ala Val Arg Glu Asp Thr Tyr Pro Val Gly Thr Gln Gly Val
            420                 425                 430

Pro Ser Leu Ala Leu Ala Gln Gly Gly Pro Gln Gly Ser Trp Arg Phe
        435                 440                 445

Leu Glu Trp Lys Ser Met Pro Arg Leu Pro Thr Asp Leu Asp Ile Gly
    450                 455                 460

Gly Pro Trp Phe Pro His Tyr Asp Phe Glu Trp Ser Cys Trp Val Arg
465                 470                 475                 480

Ala Ile Ser Gln Glu Asp Gln Leu Ala Thr Cys Trp Gln Ala Glu His
                485                 490                 495
```

-continued

```
Cys Gly Glu Val His Asn Lys Asp Met Ser Trp Pro Glu Glu Met Ser
            500                 505                 510

Phe Thr Ala Asn Ser Ser Lys Ile Asp Arg Gln Lys Val Pro Thr Glu
        515                 520                 525

Lys Gly Ala Thr Gly Leu Ser Asn Leu Gly Asn Thr Cys Phe Met Asn
    530                 535                 540

Ser Ser Ile Gln Cys Val Ser Asn Thr Gln Pro Leu Thr Gln Tyr Phe
545                 550                 555                 560

Ile Ser Gly Arg His Leu Tyr Glu Leu Asn Arg Thr Asn Pro Ile Gly
                565                 570                 575

Met Lys Gly His Met Ala Lys Cys Tyr Gly Asp Leu Val Gln Glu Leu
            580                 585                 590

Trp Ser Gly Thr Gln Lys Ser Val Ala Pro Leu Lys Leu Arg Arg Thr
        595                 600                 605

Ile Ala Lys Tyr Ala Pro Lys Phe Asp Gly Phe Gln Gln Gln Asp Ser
    610                 615                 620

Gln Glu Leu Leu Ala Phe Leu Leu Asp Gly Leu His Glu Asp Leu Asn
625                 630                 635                 640

Arg Val His Glu Lys Pro Tyr Val Glu Leu Lys Asp Ser Asp Gly Arg
                645                 650                 655

Pro Asp Trp Glu Val Ala Ala Glu Ala Trp Asp Asn His Leu Arg Arg
            660                 665                 670

Asn Arg Ser Ile Ile Val Asp Leu Phe His Gly Gln Leu Arg Ser Gln
        675                 680                 685

Val Lys Cys Lys Thr Cys Gly His Ile Ser Val Arg Phe Asp Pro Phe
    690                 695                 700

Asn Phe Leu Ser Leu Pro Leu Pro Met Asp Ser Tyr Met Asp Leu Glu
705                 710                 715                 720

Ile Thr Val Ile Lys Leu Asp Gly Thr Thr Pro Val Arg Tyr Gly Leu
                725                 730                 735

Arg Leu Asn Met Asp Glu Lys Tyr Thr Gly Leu Lys Lys Gln Leu Arg
            740                 745                 750

Asp Leu Cys Gly Leu Asn Ser Glu Gln Ile Leu Leu Ala Glu Val His
        755                 760                 765

Asp Ser Asn Ile Lys Asn Phe Pro Gln Asp Asn Gln Lys Val Gln Leu
    770                 775                 780

Ser Val Ser Gly Phe Leu Cys Ala Phe Glu Ile Pro Val Pro Ser Ser
785                 790                 795                 800

Pro Ile Ser Ala Ser Ser Pro Thr Gln Ile Asp Phe Ser Ser Ser Pro
                805                 810                 815

Ser Thr Asn Gly Met Phe Thr Leu Thr Thr Asn Gly Asp Leu Pro Lys
            820                 825                 830

Pro Ile Phe Ile Pro Asn Gly Met Pro Asn Thr Val Val Pro Cys Gly
        835                 840                 845

Thr Glu Lys Asn Phe Thr Asn Gly Met Val Asn Gly His Met Pro Ser
    850                 855                 860

Leu Pro Asp Ser Pro Phe Thr Gly Tyr Ile Ile Ala Val His Arg Lys
865                 870                 875                 880

Met Met Arg Thr Glu Leu Tyr Phe Leu Ser Pro Gln Glu Asn Arg Pro
                885                 890                 895

Ser Leu Phe Gly Met Pro Leu Ile Val Pro Cys Thr Val His Thr Arg
            900                 905                 910
```

```
Lys Lys Asp Leu Tyr Asp Ala Val Trp Ile Gln Val Ser Trp Leu Ala
        915                 920                 925

Arg Pro Leu Pro Pro Gln Glu Ala Ser Ile His Ala Gln Asp Arg Asp
    930                 935                 940

Asn Cys Met Gly Tyr Gln Tyr Pro Phe Thr Leu Arg Val Val Gln Lys
945                 950                 955                 960

Asp Gly Asn Ser Cys Ala Trp Cys Pro Gln Tyr Arg Phe Cys Arg Gly
                965                 970                 975

Cys Lys Ile Asp Cys Gly Glu Asp Arg Ala Phe Ile Gly Asn Ala Tyr
            980                 985                 990

Ile Ala Val Asp Trp His Pro Thr Ala Leu His Leu Arg Tyr Gln Thr
        995                 1000                1005

Ser Gln Glu Arg Val Val Asp Lys His Glu Ser Val Glu Gln Ser Arg
    1010                1015                1020

Arg Ala Gln Ala Glu Pro Ile Asn Leu Asp Ser Cys Leu Arg Ala Phe
1025                1030                1035                1040

Thr Ser Glu Glu Glu Leu Gly Glu Ser Glu Met Tyr Tyr Cys Ser Lys
                1045                1050                1055

Cys Lys Thr His Cys Leu Ala Thr Lys Lys Leu Asp Leu Trp Arg Leu
            1060                1065                1070

Pro Pro Phe Leu Ile Ile His Leu Lys Arg Phe Gln Phe Val Asn Asp
        1075                1080                1085

Gln Trp Ile Lys Ser Gln Lys Ile Val Arg Phe Leu Arg Glu Ser Phe
    1090                1095                1100

Asp Pro Ser Ala Phe Leu Val Pro Arg Asp Pro Ala Leu Cys Gln His
1105                1110                1115                1120

Lys Pro Leu Thr Pro Gln Gly Asp Glu Leu Ser Lys Pro Arg Ile Leu
                1125                1130                1135

Ala Arg Glu Val Lys Lys Val Asp Ala Gln Ser Ser Ala Gly Lys Glu
            1140                1145                1150

Asp Met Leu Leu Ser Lys Ser Pro Ser Ser Leu Ser Ala Asn Ile Ser
        1155                1160                1165

Ser Ser Pro Lys Gly Ser Pro Ser Ser Ser Arg Lys Ser Gly Thr Ser
    1170                1175                1180

Cys Pro Ser Ser Lys Asn Ser Ser Pro Asn Ser Ser Pro Arg Thr Leu
1185                1190                1195                1200

Gly Arg Ser Lys Gly Arg Leu Arg Leu Pro Gln Ile Gly Ser Lys Asn
                1205                1210                1215

Lys Pro Ser Ser Ser Lys Lys Asn Leu Asp Ala Ser Lys Glu Asn Gly
            1220                1225                1230

Ala Gly Gln Ile Cys Glu Leu Ala Asp Ala Leu Ser Arg Gly His Met
        1235                1240                1245

Arg Gly Gly Ser Gln Pro Glu Leu Val Thr Pro Gln Asp His Glu Val
    1250                1255                1260

Ala Leu Ala Asn Gly Phe Leu Tyr Glu His Glu Ala Cys Gly Asn Gly
1265                1270                1275                1280

Cys Gly Asp Gly Tyr Ser Asn Gly Gln Leu Gly Asn His Ser Glu Glu
                1285                1290                1295

Asp Ser Thr Asp Asp Gln Arg Glu Asp Thr His Ile Lys Pro Ile Tyr
            1300                1305                1310

Asn Leu Tyr Ala Ile Ser Cys His Ser Gly Ile Leu Ser Gly Gly His
        1315                1320                1325
```

-continued

```
Tyr Ile Thr Tyr Ala Lys Asn Pro Asn Cys Lys Trp Tyr Cys Tyr Asn
    1330                1335                1340

Asp Ser Ser Cys Glu Glu Leu His Pro Asp Glu Ile Asp Thr Asp Ser
1345                1350                1355                1360

Ala Tyr Ile Leu Phe Tyr Glu Gln Gln Gly Ile Asp Tyr Ala Gln Phe
                1365                1370                1375

Leu Pro Lys Ile Asp Gly Lys Lys Met Ala Asp Thr Ser Ser Thr Asp
            1380                1385                1390

Glu Asp Ser Glu Ser Asp Tyr Glu Lys Tyr Ser Met Leu Gln
        1395                1400                1405


<210> SEQ ID NO 2
<211> LENGTH: 4221
<212> TYPE: DNA
<213> ORGANISM: Homo sapiens

<400> SEQUENCE: 2

atggacatgg tagagaatgc agatagtttg caggcacagg agcggaagga catacttatg     60

aagtatgaca agggacaccg agctgggctg ccagaggaca aggggcctga gcccgttgga    120

atcaacagca gcattgatcg ttttggcatt ttgcatgaga cggagctgcc tcctgtgact    180

gcacgggagg cgaagaaaat tcggcgggag atgacacgaa cgagcaagtg gatggaaatg    240

ctgggagaat gggagacata taagcacagt agcaaactca tagatcgagt gtacaaggga    300

attcccatga acatccgggg cccggtgtgg tcagtcctcc tgaacattca ggaaatcaag    360

ttgaaaaacc ccggaagata ccagatcatg aaggagaggg gcaagaggtc atctgaacac    420

atccaccaca tcgacctgga cgtgaggacg actctccgga accatgtctt ctttagggat    480

cgatatggag ccaagcagag ggaactattc tacatcctcc tggcctattc ggagtataac    540

ccggaggtgg gctactgcag ggacctgagc cacatcaccg ccttgttcct cctttatctg    600

cctgaggagg acgcattctg ggcactggtg cagctgctgg ccagtgagag gcactccctg    660

ccaggattcc acagcccaaa tggtgggaca gtccaggggc tccaagacca acaggagcat    720

gtggtaccca agtcacaacc caagaccatg tggcatcagg acaaggaagg tctatgcggg    780

cagtgtgcct cgttaggctg ccttctccgg aacctgattg acgggatctc tctcgggctc    840

accctgcgcc tgtgggacgt gtatttggtg gaaggagaac aggtgttgat gccaataacc    900

agcattgctc ttaaggttca gcagaagcgc ctcatgaaga catccaggtg tggcctgtgg    960

gcacgtctgc ggaaccaatt cttcgatacc tgggccatga acgatgacac cgtgctcaag   1020

catcttaggg cctctacgaa gaaactaaca aggaagcaag ggacctgcc accccccagcc   1080

aaacgcgagc aagggtcctt ggcacccagg cctgtgccgg cttcacgtgg tgggaagacc   1140

ctctgcaagg ggtataggca ggcccctcca ggcccaccag cccagttcca gcggcccatt   1200

tgctcagctt ccccgccatg ggcatctcgt ttttccacgc cctgtcctgg tggggctgtc   1260

cgggaagaca cgtaccctgt gggcactcag ggtgtgccca gcctggccct ggctcaggga   1320

ggacctcagg gttcctggag attcctggag tggaagtcaa tgccccggct cccaacggac   1380

ctggatatag gggcccttg gttcccccat tatgattttg aatggagctg ctgggtccgt   1440

gccatatccc aggaggacca gctggccacc tgctggcagg ctgaacactg cggagaggtt   1500

cacaacaaag atatgagttg gcctgaggag atgtctttta cagcaaatag tagtaaaata   1560

gatagacaaa aggttcccac agaaaaggga gccacaggtc taagcaacct gggaaacaca   1620

tgcttcatga actcaagcat ccagtgcgtt agtaacacac agccactgac acagtatttt   1680
```

```
atctcaggga gacatcttta tgaactcaac aggacaaatc ccattggtat gaaggggcat   1740
atggctaaat gctatggtga tttagtgcag gaactctgga gtggaactca gaagagtgtt   1800
gccccattaa agcttcggcg gaccatagca aaatatgctc ccaagtttga tgggtttcag   1860
caacaagact cccaagaact tctggctttt ctcttggatg gtcttcatga agatctcaac   1920
cgagtccatg aaaagccata tgtggaactg aaggacagtg atggccgacc agactgggaa   1980
gtagctgcag aggcctggga caaccatcta agaagaaata gatcaattat tgtggatttg   2040
ttccatgggc agctaagatc tcaagtcaaa tgcaagacat gtgggcatat aagtgtccga   2100
tttgaccctt tcaatttttt gtctttgcca ctaccaatgg acagttacat ggacttagaa   2160
ataacagtga ttaagttaga tggtactacc cctgtacggt atggactaag actgaatatg   2220
gatgaaaagt acacaggttt aaaaaaacag ctgagggatc tctgtggact taattcagaa   2280
caaatcctac tagcagaagt acatgattcc aacataaaga actttcctca ggataaccaa   2340
aaagtacaac tctcagtgag cggatttttg tgtgcatttg aaattcctgt cccttcatct   2400
ccaatttcag cttctagtcc aacacaaata gatttctcct cttcaccatc tacaaatgga   2460
atgttcaccc taactaccaa tggggaccta cccaaaccaa tattcatccc caatggaatg   2520
ccaaacactg ttgtgccatg tggaactgag aagaacttca caaatggaat ggttaatggt   2580
cacatgccat ctcttcctga cagccccttt acaggttaca tcattgcagt ccaccgaaaa   2640
atgatgagga cagaactgta tttcctgtca cctcaggaga atcgccccag cctctttgga   2700
atgccattga ttgttccatg cactgtgcat acccggaaga aagacctata tgatgcggtt   2760
tggattcaag tatcctggtt agcaagacca ctcccacctc aggaagctag tattcatgcc   2820
caggatcgtg ataactgtat gggctatcaa tatccattca ctctacgagt tgtgcagaaa   2880
gatgggaact cctgtgcttg gtgcccacag tatagatttt gcagaggctg taaaattgat   2940
tgtggggaag acagagcttt cattggaaat gcctatattg ctgtggattg gcaccccaca   3000
gcccttcacc ttcgctatca aacatcccag gaaagggttg tagataagca tgagagtgtg   3060
gagcagagtc ggcgagcgca agccgagccc atcaacctgg acagctgtct ccgtgctttc   3120
accagtgagg aagagctagg ggaaagtgag atgtactact gttccaagtg taagacccac   3180
tgcttagcaa caaagaagct ggatctctgg aggcttccac ccttcctgat tattcacctt   3240
aagcgatttc aatttgtaaa tgatcagtgg ataaaatcac agaaaattgt cagatttctt   3300
cgggaaagtt ttgatccgag tgcttttttg gtaccacgag acccggccct ctgccagcat   3360
aaaccactca caccccaggg ggatgagctc tccaagccca ggattctggc aagagaggtg   3420
aagaaagtgg atgcgcagag ttcggctgga aaagaggaca tgctcctaag caaaagccca   3480
tcctcactca gcgctaacat cagcagcagc ccaaaaggtt ctccttcttc atcaagaaaa   3540
agtggaacca gctgtccctc cagcaaaaac agcagcccta atagcagccc acggactttg   3600
gggaggagca aagggaggct ccggctgccc cagattggca gcaaaaataa gccgtcaagt   3660
agtaagaaga acttggatgc cagcaaagag aatggggctg ggcagatctg tgagctggct   3720
gacgccttga gccgagggca tatgcggggg ggcagccaac cagagctggt cactcctcag   3780
gaccatgagg tagctttggc caatggattc ctttatgagc atgaagcatg tggcaatggc   3840
tgtggcgatg gctacagcaa tggtcagctt ggaaaccaca gtgaagaaga cagcactgat   3900
gaccaaagag aagacactca tattaagcct atttataatc tatatgcaat ttcatgccat   3960
tcaggaattc tgagtggggg ccattacatc acttatgcca aaaacccaaa ctgcaagtgg   4020
tactgttata atgacagcag ctgtgaggaa cttcaccctg atgaaattga caccgactct   4080
```

```
gcctacattc ttttctatga gcagcagggg atagactacg cacaatttct gccaaagatt   4140

gatggcaaaa agatggcaga cacaagcagt acggatgaag actctgagtc tgattacgaa   4200

aagtactcta tgttacagta a                                             4221


<210> SEQ ID NO 3
<211> LENGTH: 25
<212> TYPE: DNA
<213> ORGANISM: Artificial Sequence
<220> FEATURE:
<223> OTHER INFORMATION: Jak1 gRNA target

<400> SEQUENCE: 3

caccgtccca tacctcatcc ggtag                                           25


<210> SEQ ID NO 4
<211> LENGTH: 25
<212> TYPE: DNA
<213> ORGANISM: Artificial Sequence
<220> FEATURE:
<223> OTHER INFORMATION: STAT1 gRNA target

<400> SEQUENCE: 4

caccgtccca ttacaggctc agtcg                                           25


<210> SEQ ID NO 5
<211> LENGTH: 25
<212> TYPE: DNA
<213> ORGANISM: Artificial Sequence
<220> FEATURE:
<223> OTHER INFORMATION: STAT3 gRNA target

<400> SEQUENCE: 5

caccgagatt gcccggattg tggcc                                           25


<210> SEQ ID NO 6
<211> LENGTH: 11
<212> TYPE: DNA
<213> ORGANISM: Artificial Sequence
<220> FEATURE:
<223> OTHER INFORMATION: Synthetic Sequence

<400> SEQUENCE: 6

tttttttttt t                                                          11


<210> SEQ ID NO 7
<211> LENGTH: 13
<212> TYPE: DNA
<213> ORGANISM: Artificial Sequence
<220> FEATURE:
<223> OTHER INFORMATION: poly(A) tail segment

<400> SEQUENCE: 7

aaaaaaaaaa aaa                                                        13
```

COMPOSITIONS AND METHODS FOR TREATING CANCER

This application claims priority under 35 U.S.C. § 119(e) to U.S. Provisional Patent Application No. 62/771,869, filed on Nov. 27, 2018, U.S. Provisional Patent Application No. 62/796,959, filed on Jan. 25, 2019, and U.S. Provisional Patent Application No. 62/893,492, filed on Aug. 29, 2019. The foregoing applications are incorporated by reference herein.

This invention was made with government support under Grant Nos. TG 32GM008076, CA178601, and CA168452 awarded by National Institutes of Health. The government has certain rights in the invention.

FIELD OF THE INVENTION

This application relates to the field of anti-cancer therapy. More specifically, this invention provides compositions and methods for treating cancer.

BACKGROUND OF THE INVENTION

Several publications and patent documents are cited throughout the specification in order to describe the state of the art to which this invention pertains. Each of these citations is incorporated herein by reference as though set forth in full.

Immunotherapy has revolutionized cancer therapy and provided hope for patients with otherwise intractable malignancies. However, not all patients have benefited from the recent advances in immunotherapy. Despite promising results in melanoma, renal cell carcinoma, and non-small cell lung carcinoma, a significant portion of solid tumors have not been amenable to most immunotherapies. Pancreatic ductal adenocarcinoma (PDAC) affects ~53,000 Americans every year and has a dismal 5-year survival rate of ~15%, due in part to non-responsiveness to conventional therapies (Zhang, et al. (2018) Cancers (Basel) 10(2):E39; Adamska, et al. (2018) Adv. Biol. Regul., 68:77-87). The lack of effective treatments has led to a concerted push to investigate immunotherapies, however the results have been disappointing. The immunosuppressive microenvironment in PDAC is considered a key barrier to effective immunotherapy. PDAC is generally a "cold" cancer, with immune effector cells such as cytotoxic T lymphocytes (CTLs) often excluded from the tumor. Furthermore, those CTLs that do manage to penetrate are often rendered inactive (Johnson, et al. (2017) Clin. Cancer Res., 23(7):1656-69). The immune cells that do infiltrate comprise a heterogenous, but highly pro-tumorigenic combination of $T_{regs}$, M2-polarized macrophages, and myeloid-derived suppressor cells (MDSCs). In order for conventional immunotherapies to be successful, novel approaches must first increase the infiltration of anti-tumor immune effector cells and overcome the highly immune suppressive microenvironment.

Delivery of immunogenic therapies have been shown to not only cause regression of the target lesion, but have also led to clearance of distant metastasis in both pre-clinical models and clinical trials in multiple cancers (Sagiv-Barfi, et al. (2018) Sci. Transl. Med., 10:12). Vectors have been engineered to overexpress a variety immune-stimulating factors such as CXCL10 (Liu, et al. (2002) Cancer Gene Ther., 9(6):533-42), CCL5 (Lavergne, et al. (2004) J. Immunol., 173(6):3755-62), or cancer-testis antigens like NY-ESO-1 (Nishikawa, et al. (2006) J. Clin. Invest., 116(7): 1946-54) in order to elicit an immunogenic response against the tumor. However, the production of a single factor is unlikely to lead to durable responses, as single-agent therapy is rarely successful in cancer. Overexpression of multiple immunogenic pathways will therefore be required to promote a sustained immune response against the cancer. In view of the foregoing, it is clear that improved immunotherapeutic methods are needed.

SUMMARY OF THE INVENTION

In accordance with the instant invention, methods of inhibiting or treating cancer, particularly a "cold" cancer or a cancer lacking CD8+ tumor infiltrating lymphocytes (TILs) and/or other immunostimulatory features, in a subject are provided. In a particular embodiment, the method comprises administering an agent which increases ubiquitin-specific protease 6 (USP6) activity and/or expression to the subject. The agent may be administered as part of a composition further comprising a pharmaceutically acceptable carrier. In a particular embodiment, the agent is administered intratumorally, systemically, and/or to the tumor site. In a particular embodiment, the agent for increasing USP6 activity is a USP6 protein or a USP6 encoding nucleic acid molecule (e.g., an in vitro transcribed USP6 mRNA). The methods of the instant invention may further comprise the administration of an immunotherapy. In a particular embodiment, the cancer to be treated is Ewing sarcoma (ES), acute myeloid leukemia (AML), cervical, lung, ovarian, bladder, or pancreatic cancer.

BRIEF DESCRIPTION OF THE DRAWINGS

FIGS. 1A-1C show that USP6 induces an IFN response in ES cells in vitro and in primary tumors. FIG. 1A: Samples from primary Ewing sarcoma datasets (GSE7007 and GSE37371) were ranked by USP6 expression level, and GSEA was performed comparing the 5 samples with the highest levels to the 5 with the lowest. RNA-sequencing was also performed on USP6/RD-ES treated with or without doxycycline (dox), followed by GSEA pathway analysis. GSEA was also performed for nodular fasciitis dataset, which utilized the Illumina Human HT12 v4.0 BeadChip. This platform contains one USP6 probe, which is specific for USP6. GSEA of the germ cell tumor dataset, comparing seminomas to yolk sac tumors, is also provided. FIG. 1B: The indicated RD-ES cell lines were grown in the presence of doxycycline overnight, then blotted as indicated. The USP6 line represents a pooled population, whereas USP6 (High) and USP6 (Med) are clonal. FIG. 1C: Relative USP6 levels were evaluated in samples from the germ cell tumor dataset GSE10615 (U133A Microarray).

FIG. 2A: Parental or USP6/RD-ES cells were grown in doxycycline overnight, then treated with IFN$\alpha$ (left) or IFN$\gamma$ (right) (1,000 U/mL) for the indicated times, and blotted. FIG. 2B: Cells were treated with doxycycline overnight, then treated with the indicated dose of IFN$\beta$ for 0.5 hours or 8 hours. Samples were blotted as indicated; STAT3 was used as a loading control.

FIG. 3C: Cells were grown in doxycycline, then treated with 1,000 U/mL IFNβ for 18 hours or 24 hours. Apoptosis was quantified by Annexin V staining (n=4). FIG. 3D: USP6(Med), USP6 (High), and parental RD-ES cells were treated with doxycycline (dox) and IFNβ overnight, then blotted as indicated. Arrowhead indicates cleaved PARP product. FIG. 3E: USP6/TC-71 cells were grown in the absence or presence of doxycycline (dox), then treated with 100 U/mL of the indicated IFN for 24 hours. FIG. 3F: Cells were grown in doxycycline (dox), then treated with 100 U/mL of the indicated IFN for 24 hours. Apoptosis was quantified by Annexin V staining (n=3). ERK or p65 was used as a loading control.

FIGS. 4A and 4B: Cells were treated with doxycycline (dox) and IFNβ overnight, in the absence or presence of 50 μmol/L pan-caspase inhibitor ZVAD (pan) or caspase-8 inhibitor IETD. Lysates were blotted as indicated. FIGS. 4C and 4D: Cells treated with doxycycline (dox) and IFNβ overnight, in the presence of caspase inhibitors as indicated, and caspase-9 (n=6) and caspase-3/7 activity was measured (n=3). Activity was calculated as fold relative to that in untreated USP6 (High)/RD-ES. FIG. 4E: USP6 (High)/RD-ES were treated with doxycycline (dox) and IFNβ overnight, in the presence of a pan-Jak inhibitor (1 μmol/L) or NFκB inhibitor PS-1145 (15 μmol/L). FIG. 4F: Jak1, STAT1, or STAT3 were deleted by CRISPR gene editing. Cells were treated with doxycycline and IFNβ overnight, then blotted as shown. Arrowhead indicates cleaved PARP product; ERK was used as a loading control.

FIGS. 5A and 5B: Cells were treated with doxycycline (dox) and the indicated IFN (1,000 U/mL) for 24 hours. TRAIL mRNA levels were quantified by qRT-PCR, and fold-induction relative to untreated RD-ES determined. FIG. 5C: The indicated cells were treated with doxycycline (dox) and IFNβ (1,000 U/mL) for 24 hours, and blotted as indicated. FIGS. 5D and 5E: The indicated cells were treated overnight with IFNβ (1,000 U/mL) or reTRAIL (200 ng/mL), in the presence of increasing amounts (1.0, 1.5, or 2.0 mg) of anti-TRAIL or control IgG. Samples were blotted in FIG. 5D, or subjected to Annexin V staining in FIG. 5E. FIG. 5F: TRAIL was depleted from USP6/RD-ES cells using CRISPR. Cells were treated overnight as indicated, and blotted as shown. FIG. 5G: The indicated Ewing sarcoma cell lines were blotted as shown. ERK or p65 was used as a loading control.

FIGS. 6A-6C: USP6/RD-ES cells were treated with doxycycline (dox) and the indicated doses of TRAIL or IFNα (1,000 U/mL) for the indicated times. In FIG. 6C, TRAIL was used at 10 ng/mL, and pan-caspase inhibitor ZVAD (pan) or caspase-8 inhibitor (8) was added as shown. STAT3 or p65 was used as a loading control. FIG. 6D: Mechanism of IFN-induced apoptosis of USP6-positive Ewing sarcoma cells: Jak1 levels are upregulated by USP6-mediated deubiquitination, greatly sensitizing cells to IFNs. Type I IFNs, particularly IFNβ, induces transcription of TRAIL, which induces apoptosis through binding its receptor DR4. TRAIL/DR4 then triggers USP6 downregulation through caspase activation.

FIG. 15 also provides graphs of a timecourse of protein expression of USP6, CD54, MHC Class I, and DR5 in 293T cells after USP6 mRNA introduction.

FIG. 16B provides graphs of the expression of DR5 and MHC Class I in THP-1 or U937 AML cells after USP6 mRNA introduction.

DETAILED DESCRIPTION OF THE INVENTION

Figure 2A:
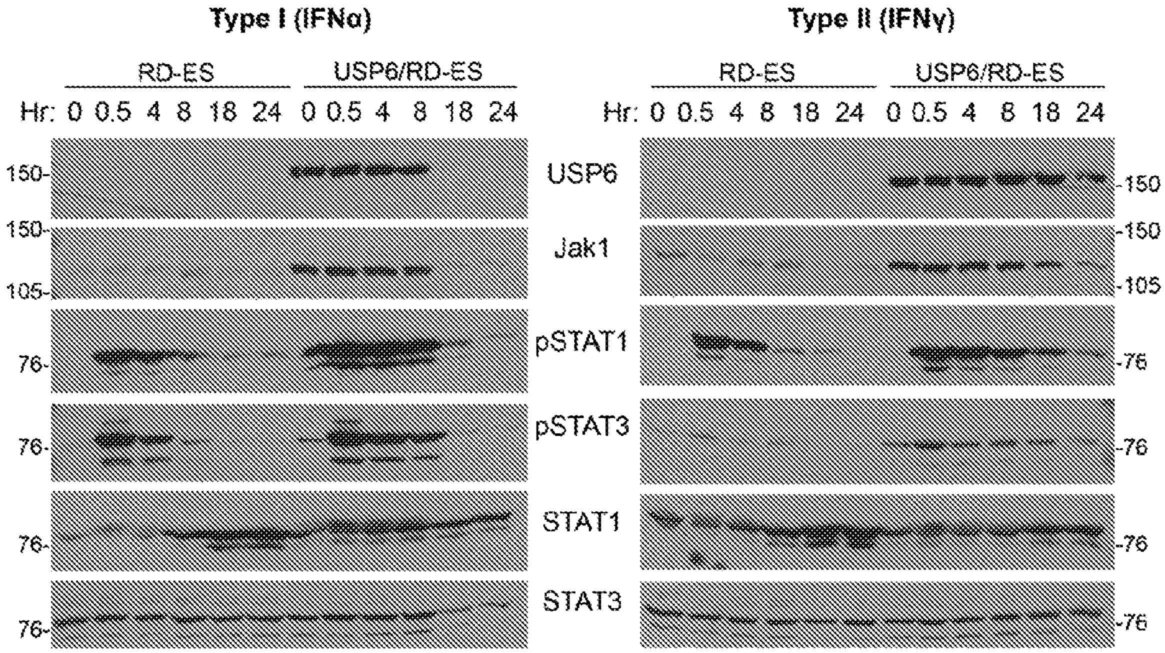
FIGS. 2A-2B show USP6 enhances signaling and sensitivity of Ewing sarcoma cells to type I and type II IFNs.

Herein, it is shown that the ubiquitin-specific protease 6 (USP6) gene has potent anti-tumorigenic properties in Ewing sarcoma, a highly lethal pediatric malignancy. High USP6 expression in Ewing sarcoma cells induces secretion of immunostimulatory cytokines and chemokines, leading to robust tumor immune infiltration, and differentiation of immune cells toward anti-tumorigenic phenotypes. USP6 also triggers increased surface expression of receptors that promote recognition and killing of tumor cells by immune effector cells, such as natural killer and CD8+ T lymphocytes. Specifically, Type I IFN induces synergistic expression of the pro-apoptotic ligand TRAIL, selectively killing USP6+ Ewing sarcoma cells. IFN also induces heightened expression of numerous anti-tumorigenic chemokines, such as CXCL9/10/11 and CCL5, in USP6+ Ewing sarcoma cells. Conditioned medium from these cells enhances migration of primary monocytes and activated CD4+/CD8+ T cells in vitro. USP6 also increases surface expression of MHC I. Mice bearing xenografts of USP6+ ES cells exhibit prolonged event-free survival and time to terminal tumor mass. USP6+ tumors also contain dramatically enhanced immune infiltration. Finally, transcriptome analysis of primary Ewing sarcoma samples reveals that high USP6 expression is associated with an immune infiltration gene signature in vivo.

Moreover, high USP6 expression is associated with dramatically increased survival in Ewing sarcoma, as well as other highly lethal cancers, including pancreatic ductal adenocarcinoma, bladder carcinoma, cervical carcinoma, and lung adenocarcinoma. Indeed, USP6 expression is highly restricted in normal tissues. However, elevated expression of USP6 occurs in several pediatric and adult cancers, including Ewing sarcoma. Approximately 25% of Ewing sarcoma patients were found to harbor elevated USP6 expression. Strikingly, Ewing sarcoma patients with high USP6 levels experienced dramatically increased event-free and overall survival when compared to those with low expression.

These significant survival benefits arise from USP6's potent immunostimulatory effects. For example, USP6 induces the secretion of numerous anti-tumor cytokines that are known to decrease angiogenesis and enhance migration/activation of key anti-tumor immune effector cells. USP6 also sensitizes cells to the immunomodulatory effects of interferon (IFN), a key cytokine involved in immune recognition of the tumor cells. IFN can even directly kill USP6-expressing tumor cells. Tumors that overexpress USP6 also have enhanced infiltration of immune cells. Lastly, USP6 increases the surface expression of several key receptors involved in immune cell recognition and tumor clearance. For example, USP6-expressing tumor cells have enhanced MHC Class I and several ligands involved in natural killer cell-mediated cytotoxicity.

The data provided herein demonstrates that modulating USP6 activity is an effective therapy to combat malignancy. The in vivo data shows that artificially increasing USP6 expression and/or activity within tumor cell leads to decreased tumor growth and enhanced survival in mice, providing proof-of-concept data that increasing USP6 expression is anti-tumorigenic. Many of the cancers that show elevated USP6 expression are refractory to current therapies, including the new classes of immunotherapies such as checkpoint inhibitors and engineered T cells.

Specifically, PDAC is an aggressive cancer, with few treatments currently available. Despite recent progress in other tumors, immunotherapy has not been widely successful in PDAC due to the immunosuppressive microenvironment. Transient overexpression of USP6 in PDAC will turn what is normally considered an immunologically "cold" tumor (i.e. lacking CD8+ tumor infiltrating lymphocytes (TILs) and other immunostimulatory features), into one that allows immunotherapies to reach their full potential. Indeed, as explained hereinabove, USP6 improves patient outcome due to its ability to trigger a "hot" tumor microenvironment and tumor elimination, mediated through its effects on IFN signaling.

Notably, Jak1 is highly expressed in PDAC. Thus, PDAC is particularly susceptible to the immune-stimulatory effects of transient USP6 overexpression based on the mechanism of action of USP6 described herein. Increasing USP6 activity will reverse the immune suppressive microenvironment of PDAC while enhancing recruitment of anti-tumor effector cells.

In accordance with the instant invention, methods for the inhibition (e.g., reduction, slowing, etc.), prevention, and/or treatment of cancer are provided. The methods comprise increasing USP6 expression and/or activity, particularly in the cancer cells or tumor and/or in the tumor microenvironment. In a particular embodiment, the methods comprise administering USP6 protein to the cancer cells or tumor and/or to the tumor microenvironment. In a particular embodiment, the methods comprise administering a USP6 encoding nucleic acid molecule (e.g., mRNA) to the cancer cells or tumor and/or to the tumor microenvironment. The USP6 encoding nucleic acid molecule may be administered, for example, in a vector, viral vector, nanoparticle, liposome, or micelle. In a particular embodiment, USP6 expression and/or activity is increased by pharmacologically enhancing endogenous USP6 expression or activity. Notably, the delivery of exogenous nucleic acid molecules and/or proteins are known to beneficially induce immune activation in a subject (e.g., the delivered agents function as adjuvants). The agents of the instant invention may be administered to the subject in a composition comprising at least one carrier (e.g., pharmaceutically acceptable carrier).

In a particular embodiment, USP6 activity/expression is increased transiently. Transient expression avoids potential constitutive off-target expression of USP6 in non-tumor tissue. The temporary increase in USP6 activity/expression can serve as a therapy by "jumpstarting" the patient's immune system. Moreover, the transient expression of USP6 allows for repeated administration of the agent to tumors or cancer cells as needed. In a particular embodiment, the USP6 encoding nucleic acid molecule administered to the subject is an RNA molecule (e.g., mRNA), thereby avoiding possible integrations within the host genome that could occur with the use of plasmids or viral vectors.

In a particular embodiment, the USP6 encoding nucleic acid molecule administered to the subject is an mRNA, particularly an in vitro transcribed (IVT) mRNA. In a particular embodiment, the mRNA is a mature RNA and/or lacks introns. Unmodified mRNA generally has poor stability, translation, and uptake in vitro and in vivo (Islam, et al. (2015) Biomater. Sci., 3(12):1519-33; Sahin, et al. (2014) Nat. Rev. Drug Discov., 13(10):759-80). However, recent advances have found mRNA modifications that increase efficacy (see, e.g., Loomis et al. (2018) Bioconjugate Chem., 29(9):3072-3083). The mRNA may be modified with one or more (or all) of the following features or as described in Sahin, et al. (Nat. Rev. Drug Discov. (2014) 13(10):759-80).

At the outset, the mRNA will possess the necessary 5' and 3' elements to be translated within a cell. In a particular embodiment, the mRNA comprises a polyA tail. Polyadenylate tails can vary in the number of adenylates present in the tail (Steinle, et al. (2017) Stem Cells 35:68-79). In a particular embodiment, the polyA tail has between 50-500 bases, between 100-250 bases, between 100-200 bases, between 100-175 bases, between 120-150 bases, between 100-150 bases, between 110-130 bases, or about 120 bases.

The mRNA may comprise a 3'UTR or lack a 3'UTR. In a particular embodiment, the mRNA lacks a 3' UTR. In a particular embodiment, the mRNA comprises the USP6 3'UTR. In a particular embodiment, the mRNA comprises a 3'UTR which improves mRNA stability and/or translation. For example, the mRNA may comprise the beta globin 3'UTR (e.g., human).

In a particular embodiment, the mRNA comprises a 5' cap, particularly an ARCA (Anti-Reverse Cap Analog). Robust translation of mRNA is assisted by a functional 5' cap structure. For example, the mRNA product can be transcribed, modified with a 5' cap, and purified using established protocols (Islam, et al. (2015) Biomater. Sci., 3(12):1519-33; Sahin, et al. (2014) Nat. Rev. Drug Discov., 13(10):759-80; Holtkamp, et al. (2006) Blood 108(13): 4009-17). Commercially available kits such as the HiScribe™ T7 ARCA (Anti-Reverse Cap Analog) mRNA Kit (New England BioLabs; Ipswich, MA) can be used to generated capped and tailed mRNA. Examples of 5' caps include, without limitation, 7-methylguanosine ($m^7G$) and $m^7$GpppG cap analogues (e.g., ARCAs) (Wolff, et al. (1990) Science 247:1465-1468; Malone, et al. (1989) Proc. Natl Acad. Sci., 86:6077-6081). Anti-reverse cap analogues (ARCAs; $m_2^{7,3'-O}$GpppG), optionally comprising a phosphorothioate, exhibit superior translational efficiency in various cell types (Stepinski, et al. (2001) RNA 7:1486-1495; Jemielity, et al. (2003) RNA 9:1108-1122; Mockey, et al. (2006) Biochem. Biophys. Res. Commun. 340:1062-1068; Rabinovich, et al. (2006) Hum. Gene Ther. 17:1027-1035; Grudzien-Nogalska, et al. (2007) RNA 13:1745-1755; Kowalska, et al. (2008) RNA 14:1119-1131; Kuhn, et al. (2010) Gene Ther. 17:961-971).

Protamine-conjugated mRNA has been extensively characterized in the clinic (Weide, et al. (2009) J. Immunother., 32(5):9) and has the added benefit of degraded rapidly (<2 hour) in serum, while also enhancing the immunostimulatory effects of its cargo in target cells (Islam, et al. (2015) Biomater. Sci., 3(12):1519-33; Sahin, et al. (2014) Nat. Rev. Drug Discov., 13(10):759-80). Injection of whole tumor, oncogene-containing IVT mRNA in Phase I/II trials has been shown to be safe and effective (Weide, et al. (2008) J. Immunother., 32(2):7). Based on the stability of other modified IVT mRNAs, the half-life of the modified USP6 mRNA will be in the range of several days to a week.

While modifying the poly-A tail and capping the 5' end of USP6 mRNA will enhance stability and expression, modification of the coding region, 5' and 3' UTRs, and/or use of modified nucleosides can be used as well (Sahin, et al. (2014) Nat. Rev. Drug Discov., 13(10):759-80; Steinle, et al. (2017) Stem Cells, 35:68-79). In a particular embodiment, the mRNA comprises at least one modified or non-natural (e.g., not A, C, U, or G) base (Limbach et al. (1994) Nucleic Acids Res. 22(12):2183-2196). In a particular embodiment, the mRNA comprises only modified or non-natural (e.g., not A, C, U, or G) bases. In a particular, embodiment the mRNA comprises pseudouridine (Ψ) and/or 5-methylcytidines (e.g., in place of uridines and cytodines, respectively). In a particular embodiment, at least 10%, at least 20%, at least 30%, at least 40%, at least 50%, at least 60%, at least 70%, or more (including all (100%)) of the uridines of the mRNA are replaced with pseudouridine. In a particular embodiment, about 30% to about 70%, about 40% to about 60%, about 45% to about 55%, or about 50% of the uridines of the mRNA are replaced with pseudouridine. In a particular embodiment, at least 10%, at least 20%, at least 30%, at least 40%, at least 50%, at least 60%, at least 70%, or more (including all (100%)) of the cytodines of the mRNA are replaced with 5-methylcytodine. In a particular embodiment, about 30% to about 70%, about 40% to about 60%, about 45% to about 55%, or about 50% of the cytodines of the mRNA are replaced with 5-methylcytodine. Other modified nucleosides include, without limitation, 5-methoxy uridine, 5-methyl uridine, N1-methyl pseudouridine, 5-hydroxymethyl cytidine, N1-ethyl pseudouridine, 5-methoxy cytidine, 5-carboxy methyl ester uridine, 2-thio uridine, 7-methylguanosine, and $N^6$-methyladenosine.

The mRNA may also be encapsulated. Encapsulated IVT mRNA has been shown in several clinical trials to be both safe and lead to short-term expression of numerous proteins. In a particular embodiment, the IVT mRNA is contained within a nanoparticle, liposome, or micelle (e.g., a lipid nanoparticle or micelle). In a particular embodiment, the encapsulated IVT mRNA may be directed to the tumor or cancer to be treated by using a binding agent which binds a tumor antigen (e.g., a surface protein preferentially expressed on the tumor or cancer compared to other cells). For example, the nanoparticle, liposome, or micelle may be linked to a binding agent, particularly an antibody (e.g., immunologically specific for a tumor antigen) or a nanobody (Bannas, et al., Front. Immunol. (2017) 8:1603) specific for a tumor antigen (e.g., CD13). Notably, as explained above, the transient nature of IVT mRNA in both serum and intracellular likely precludes IVT USP6 mRNA from being pathogenic. Decreasing the dose and mRNA modifications to reduce stability could be used to prevent long-term pathogenic USP6 expression, if necessary.

In a particular embodiment, the USP6 is mammalian. In a particular embodiment, the USP6 is hominoid. In a particular embodiment, the USP6 is human. Amino acid and nucleic acid sequences for USP6 are provided at Gene ID: 9098 and GenBank Accession Nos. NM_001304284.1, NP_001291213.1, NM_004505.3, and NPP_004496.2. An example of an amino acid sequence for USP6 is:

```
                                   (SEQ ID NO: 1)
   1 MDMVENADSL QAQERKDILM KYDKGHRAGL
     PEDKGPEPVG INSSIDRFGI LHETELPPVT
  61 AREAKKIRRE MTRTSKWMEM LGEWETYKHS
     SKLIDRVYKG IPMNIRGPVW SVLLNIQEIK
 121 LKNPGRYQIM KERGKRSSEH IHHIDLDVRT
     TLRNHVFFRD RYGAKQRELF YILLAYSEYN
 181 PEVGYCRDLS HITALFLLYL PEEDAFWALV
     QLLASERHSL PGFHSPNGGT VQGLQDQQEH
 241 VVPKSQPKTM WHQDKEGLCG QCASLGCLLR
     NLIDGISLGL TLRLWDVYLV EGEQVLMPIT
 301 SIALKVQQKR LMKTSRCGLW ARLRNQFFDT
```

-continued

```
     WAMNDDTVLK HLRASTKKLT RKQGDLPPPA
 361 KREQGSLAPR PVPASRGGKT LCKGYRQAPP
     GPPAQFQRPI CSASPPWASR FSTPCPGGAV
 421 REDTYPVGTQ GVPSLALAQG GPQGSWRFLE
     WKSMPRLPTD LDIGGPWFPH YDFEWSCWVR
 481 AISQEDQLAT CWQAEHCGEV HNKDMSWPEE
     MSFTANSSKI DRQKVPTEKG ATGLSNLGNT
 541 CFMNSSIQCV SNTQPLTQYF ISGRHLYELN
     RTNPIGMKGH MAKCYGDLVQ ELWSGTQKSV
 601 APLKLRRTIA KYAPKFDGFQ QQDSQELLAF
     LLDGLHEDLN RVHEKPYVEL KDSDGRPDWE
 661 VAAEAWDNHL RRNRSIIVDL FHGQLRSQVK
     CKTCGHISVR FDPFNFLSLP LPMDSYMDLE
 721 ITVIKLDGTT PVRYGLRLNM DEKYTGLKKQ
     LRDLCGLNSE QILLAEVHDS NIKNFPQDNQ
 781 KVQLSVSGFL CAFEIPVPSS PISASSPTQI
     DFSSSPSTNG MFTLTTNGDL PKPIFIPNGM
 841 PNTVVPCGTE KNFTNGMVNG HMPSLPDSPF
     TGYIIAVHRK MMRTELYFLS PQENRPSLFG
 901 MPLIVPCTVH TRKKDLYDAV WIQVSWLARP
     LPPQEASIHA QDRDNCMGYQ YPFTLRVVQK
 961 DGNSCAWCPQ YRFCRGCKID CGEDRAFIGN
     AYIAVDWHPT ALHLRYQTSQ ERVVDKHESV
1021 EQSRRAQAEP INLDSCLRAF TSEEELGESE
     MYYCSKCKTH CLATKKLDLW RLPPFLIIHL
1081 KRFQFVNDQW IKSQKIVRFL RESFDPSAFL
     VPRDPALCQH KPLTPQGDEL SKPRILAREV
1141 KKVDAQSSAG KEDMLLSKSP SSLSANISSS
     PKGSPSSSRK SGTSCPSSKN SSPNSSPRTL
1201 GRSKGRLRLP QIGSKNKPSS SKKNLDASKE
     NGAGQICELA DALSRGHMRG GSQPELVTPQ
1261 DHEVALANGF LYEHEACGNG CGDGYSNGQL
     GNHSEEDSTD DQREDTHIKP IYNLYAISCH
1321 SGILSGGHYI TYAKNPNCKW YCYNDSSCEE
     LHPDEIDTDS AYILFYEQQG IDYAQFLPKI
1381 DGKKMADTSS TDEDSESDYE KYSMLQ
```

An example of a nucleic acid sequence encoding for USP6 is (4221 nucleotides):

```
                                   (SEQ ID NO: 2)
ATGGACATGGTAGAGAATGCAGATAGTTTGCAGGC
ACAGGAGCGGAAGGACATACTTATGAAGTATGACA
```

-continued

```
AGGGACACCGAGCTGGGCTGCCAGAGGACAAGGGG
CCTGAGCCCGTTGGAATCAACAGCAGCATTGATCG
TTTTGGCATTTTGCATGAGACGGAGCTGCCTCCTG
TGACTGCACGGGAGGCGAAGAAAATTCGGCGGGAG
ATGACACGAACGAGCAAGTGGATGGAAATGCTGGG
AGAATGGGAGACATATAAGCACAGTAGCAAACTCA
TAGATCGAGTGTACAAGGGAATTCCCATGAACATC
CGGGGCCCGGTGTGGTCAGTCCTCCTGAACATTCA
GGAAATCAAGTTGAAAAACCCCGGAAGATACCAGA
TCATGAAGGAGAGGGGCAAGAGGTCATCTGAACAC
ATCCACCACATCGACCTGGACGTGAGGACGACTCT
CCGGAACCATGTCTTCTTTAGGGATCGATATGGAG
CCAAGCAGAGGGAACTATTCTACATCCTCCTGGCC
TATTCGGAGTATAACCCGGAGGTGGGCTACTGCAG
GGACCTGAGCCACATCACCGCCTTGTTCCTCCTTT
ATCTGCCTGAGGAGGACGCATTCTGGGCACTGGTG
CAGCTGCTGGCCAGTGAGAGGCACTCCCTGCCAGG
ATTCCACAGCCCAAATGGTGGGACAGTCCAGGGGC
TCCAAGACCAACAGGAGCATGTGGTACCCAAGTCA
CAACCCAAGACCATGTGGCATCAGGACAAGGAAGG
TCTATGCGGGCAGTGTGCCTCGTTAGGCTGCCTTC
TCCGGAACCTGATTGACGGGATCTCTCTCGGGCTC
ACCCTGCGCCTGTGGGACGTGTATTTGGTGGAAGG
AGAACAGGTGTTGATGCCAATAACCAGCATTGCTC
TTAAGGTTCAGCAGAAGCGCCTCATGAAGACATCC
AGGTGTGGCCTGTGGGCACGTCTGCGGAACCAATT
CTTCGATACCTGGGCCATGAACGATGACACCGTGC
TCAAGCATCTTAGGGCCTCTACGAAGAAACTAACA
AGGAAGCAAGGGGACCTGCCACCCCCAGCCAAACG
CGAGCAAGGGTCCTTGGCACCCAGGCCTGTGCCGG
CTTCACGTGGTGGGAAGACCCTCTGCAAGGGGTAT
AGGCAGGCCCCTCCAGGCCCACCAGCCCAGTTCCA
GCGGCCCATTTGCTCAGCTTCCCCGCCATGGGCAT
CTCGTTTTTCCACGCCCTGTCCTGGTGGGGCTGTC
CGGGAAGACACGTACCCTGTGGGCACTCAGGGTGT
GCCCAGCCTGGCCCTGGCTCAGGGAGGACCTCAGG
GTTCCTGGAGATTCCTGGAGTGGAAGTCAATGCCC
CGGCTCCCAACGGACCTGGATATAGGGGGCCCTTG
GTTCCCCCATTATGATTTTGAATGGAGCTGCTGGG
TCCGTGCCATATCCCAGGAGGACCAGCTGGCCACC
```

-continued

```
TGCTGGCAGGCTGAACACTGCGGAGAGGTTCACAA
CAAAGATATGAGTTGGCCTGAGGAGATGTCTTTTA
CAGCAAATAGTAGTAAAATAGATAGACAAAAGGTT
CCCACAGAAAAGGGAGCCACAGGTCTAAGCAACCT
GGGAAACACATGCTTCATGAACTCAAGCATCCAGT
GCGTTAGTAACACACAGCCACTGACACAGTATTTT
ATCTCAGGGAGACATCTTTATGAACTCAACAGGAC
AAATCCCATTGGTATGAAGGGGCATATGGCTAAAT
GCTATGGTGATTTAGTGCAGGAACTCTGGAGTGGA
ACTCAGAAGAGTGTTGCCCCATTAAAGCTTCGGCG
GACCATAGCAAAATATGCTCCCAAGTTTGATGGGT
TTCAGCAACAAGACTCCCAAGAACTTCTGGCTTTT
CTCTTGGATGGTCTTCATGAAGATCTCAACCGAGT
CCATGAAAAGCCATATGTGGAACTGAAGGACAGTG
ATGGCCGACCAGACTGGGAAGTAGCTGCAGAGGCC
TGGGACAACCATCTAAGAAGAAATAGATCAATTAT
TGTGGATTTGTTCCATGGGCAGCTAAGATCTCAAG
TCAAATGCAAGACATGTGGGCATATAAGTGTCCGA
TTTGACCCTTTCAATTTTTTGTCTTTGCCACTACC
AATGGACAGTTACATGGACTTAGAAATAACAGTGA
TTAAGTTAGATGGTACTACCCCTGTACGGTATGGA
CTAAGACTGAATATGGATGAAAAGTACACAGGTTT
AAAAAAACAGCTGAGGGATCTCTGTGGACTTAATT
CAGAACAAATCCTACTAGCAGAAGTACATGATTCC
AACATAAAGAACTTTCCTCAGGATAACCAAAAAGT
ACAACTCTCAGTGAGCGGATTTTTGTGTGCATTTG
AAATTCCTGTCCCTTCATCTCCAATTTCAGCTTCT
AGTCCAACACAAATAGATTTCTCCTCTTCACCATC
TACAAATGGAATGTTCACCCTAACTACCAATGGGG
ACCTACCCAAACCAATATTCATCCCCAATGGAATG
CCAAACACTGTTGTGCCATGTGGAACTGAGAAGAA
CTTCACAAATGGAATGGTTAATGGTCACATGCCAT
CTCTTCCTGACAGCCCCTTTACAGGTTACATCATT
GCAGTCCACCGAAAAATGATGAGGACAGAACTGTA
TTTCCTGTCACCTCAGGAGAATCGCCCCAGCCTCT
TTGGAATGCCATTGATTGTTCCATGCACTGTGCAT
ACCCGGAAGAAAGACCTATATGATGCGGTTTGGAT
TCAAGTATCCTGGTTAGCAAGACCACTCCCACCTC
AGGAAGCTAGTATTCATGCCCAGGATCGTGATAAC
TGTATGGGCTATCAATATCCATTCACTCTACGAGT
TGTGCAGAAAGATGGGAACTCCTGTGCTTGGTGCC
```

-continued

```
CACAGTATAGATTTTGCAGAGGCTGTAAAATTGAT
TGTGGGGAAGACAGAGCTTTCATTGGAAATGCCTA
TATTGCTGTGGATTGGCACCCCACAGCCCTTCACC
TTCGCTATCAAACATCCCAGGAAAGGGTTGTAGAT
AAGCATGAGAGTGTGGAGCAGAGTCGGCGAGCGCA
AGCCGAGCCCATCAACCTGGACAGCTGTCTCCGTG
CTTTCACCAGTGAGGAAGAGCTAGGGGAAAGTGAG
ATGTACTACTGTTCCAAGTGTAAGACCCACTGCTT
AGCAACAAAGAAGCTGGATCTCTGGAGGCTTCCAC
CCTTCCTGATTATTCACCTTAAGCGATTTCAATTT
GTAAATGATCAGTGGATAAAATCACAGAAAATTGT
CAGATTTCTTCGGGAAAGTTTTGATCCGAGTGCTT
TTTTGGTACCACGAGACCCGGCCCTCTGCCAGCAT
AAACCACTCACACCCCAGGGGGATGAGCTCTCCAA
GCCCAGGATTCTGGCAAGAGAGGTGAAGAAAGTGG
ATGCGCAGAGTTCGGCTGGAAAAGAGGACATGCTC
CTAAGCAAAAGCCCATCCTCACTCAGCGCTAACAT
CAGCAGCAGCCCAAAAGGTTCTCCTTCTTCATCAA
GAAAAAGTGGAACCAGCTGTCCCTCCAGCAAAAAC
AGCAGCCCTAATAGCAGCCCACGGACTTTGGGGAG
GAGCAAAGGGAGGCTCCGGCTGCCCCAGATTGGCA
GCAAAAATAAGCCGTCAAGTAGTAAGAAGAACTTG
GATGCCAGCAAAGAGAATGGGGCTGGGCAGATCTG
TGAGCTGGCTGACGCCTTGAGCCGAGGGCATATGC
GGGGGGGCAGCCAACCAGAGCTGGTCACTCCTCAG
GACCATGAGGTAGCTTTGGCCAATGGATTCCTTTA
TGAGCATGAAGCATGTGGCAATGGCTGTGGCGATG
GCTACAGCAATGGTCAGCTTGGAAACCACAGTGAA
GAAGACAGCACTGATGACCAAAGAGAAGACACTCA
TATTAAGCCTATTTATAATCTATATGCAATTTCAT
GCCATTCAGGAATTCTGAGTGGGGGCCATTACATC
ACTTATGCCAAAAACCCAAACTGCAAGTGGTACTG
TTATAATGACAGCAGCTGTGAGGAACTTCACCCTG
ATGAAATTGACACCGACTCTGCCTACATTCTTTTC
TATGAGCAGCAGGGGATAGACTACGCACAATTTCT
GCCAAAGATTGATGGCAAAAAGATGGCAGACACAA
GCAGTACGGATGAAGACTCTGAGTCTGATTACGAA
AAGTACTCTATGTTACAGTAA
```

In a particular embodiment, the nucleic acid sequence encoding USP6 is an RNA version of SEQ ID NO: 2.

In a particular embodiment, the methods of the instant invention further comprise the administration of a chemotherapeutic agent and/or an immunotherapy to the subject. The immunotherapy may be administered before, after, and/or simultaneously with the agent for increasing USP6 activity/expression. Examples of immunotherapy include, without limitation, checkpoint inhibitors, interferon (IFN), type I IFN (e.g., IFNα and/or IFNβ), IFNγ, adoptive T cell therapy, and engineered T cells. Checkpoint inhibitors (e.g., anti-PD-1L or anti-CTLA4) dramatically enhance the immune response when used as an adjuvant with an immune stimulant (Sagiv-Barfi, et al. (2018) Sci. Transl. Med., 10:12). Examples of checkpoint inhibitors include, without limitation: PD-1 inhibitors (e.g., antibodies, particularly monoclonal antibodies, immunologically specific for PD-1 such as pembrolizumab (Keytruda®) and nivolumab (Opdivo®)); PD-L1 inhibitors (e.g., antibodies, particularly monoclonal antibodies, immunologically specific for PD-L1 such as atezolizumab (Tecentriq®)); and CTLA-4 inhibitors (e.g., antibodies, particularly monoclonal antibodies, immunologically specific for CTLA-4 such as ipilimumab (Yervoy®)).

The cancer that may be treated using the compositions and methods of the instant invention include, but are not limited to, prostate cancer, colorectal cancer, pancreatic cancer, cervical cancer, stomach cancer (gastric cancer), endometrial cancer, brain cancer, glioblastoma, liver cancer, bladder cancer, ovarian cancer, testicular cancer, head and neck cancer, throat cancer, skin cancer, melanoma, basal carcinoma, mesothelioma, lymphoma, leukemia, acute myeloid leukemia, chronic myeloid leukemia, esophageal cancer, breast cancer, rhabdomyosarcoma, sarcoma, lung cancer, small-cell lung carcinoma, non-small-cell lung carcinoma, adrenal cancer, thyroid cancer, renal cancer, bone cancer, neuroendocrine cancer, and choriocarcinoma. In a particular embodiment, the cancer forms a tumor. In a particular embodiment, the cancer involves metastases. In a particular embodiment, the cancer is cervical cancer. In a particular embodiment, the cancer is lung cancer. In a particular embodiment, the cancer is bladder cancer. In a particular embodiment, the cancer is ovarian cancer. In a particular embodiment, the cancer is pancreatic cancer (e.g., pancreatic ductal adenocarcinoma). In a particular embodiment, the cancer is Ewing sarcoma. In a particular embodiment, the cancer is acute myeloid leukemia.

The agents of the instant invention will generally be administered to a patient as a pharmaceutical preparation. The term "patient" as used herein refers to human or animal subjects. These agents may be employed therapeutically, under the guidance of a physician for the treatment of cancer.

The pharmaceutical preparation comprising the agents of the invention may be conveniently formulated for administration with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated.

The dose and dosage regimen of the agents according to the invention that is suitable for administration to a particular patient may be determined by a physician considering the patient's age, sex, weight, general medical condition, and the specific condition and severity thereof for which the agent is being administered. The physician may also consider the route of administration of the agent, the pharmaceutical carrier with which the agents may be combined, and the agents' biological activity.

Selection of a suitable pharmaceutical preparation depends upon the method of administration chosen. For example, the agents of the invention may be administered by direct injection into any cancerous tissue (e.g., tumor) or into the surrounding area. In this instance, a pharmaceutical preparation comprises the agents dispersed in a medium that is compatible with the cancerous tissue.

Agents may also be administered parenterally by intravenous injection into the blood stream, or by subcutaneous, intramuscular or intraperitoneal injection. Pharmaceutical preparations for parenteral injection are known in the art. If parenteral injection is selected as a method for administering the agents, steps must be taken to ensure that sufficient amounts of the molecules reach their target cells to exert a biological effect.

Pharmaceutical compositions containing agents of the present invention as the active ingredient in intimate admixture with a pharmaceutical carrier can be prepared according to conventional pharmaceutical compounding techniques. The carrier may take a wide variety of forms depending on the form of preparation desired for administration. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of the agents of the invention may be determined by evaluating the toxicity of the agents in animal models. Various concentrations of the agents of the instant invention may be administered to mice with transplanted human tumors, and the minimal and maximal dosages may be determined based on the results of significant reduction of tumor size and side effects as a result of the treatment. Appropriate dosage unit may also be determined by assessing the efficacy of the agents in combination with other standard anti-cancer drugs. The dosage units of the agents may be determined individually or in combination with each anti-cancer treatment according to greater shrinkage and/or reduced growth rate of tumors.

The compositions comprising the agents of the instant invention may be administered at appropriate intervals, for example, at least twice a day or more until the pathological symptoms are reduced or alleviated, after which the dosage may be reduced to a maintenance level. The appropriate interval in a particular case would normally depend on the condition of the patient.

Definitions

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., TrisHCl, acetate, phosphate), water, aqueous solutions, oils, bulking substance (e.g., lactose, mannitol), excipient, auxiliary agent or vehicle with which an active agent of the present invention is administered. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, PA); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients (3rd Ed.), American Pharmaceutical Association, Washington.

As used herein, the term "subject" refers to an animal, particularly a mammal, particularly a human.

As used herein, the term "prevent" refers to the prophylactic treatment of a subject who is at risk of developing a condition resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc.

A "therapeutically effective amount" of a compound or a pharmaceutical composition refers to an amount effective to prevent, inhibit, or treat a particular disorder or disease and/or the symptoms thereof.

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diptheria toxin, and *Pseudomonas* exotoxin); taxanes; alkylating agents (e.g., temozolomide, nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes (e.g., cisplatin, carboplatin, tetraplatin, ormaplatin, thioplatin, satraplatin, nedaplatin, oxaliplatin, heptaplatin, iproplatin, transplatin, and lobaplatin); bioreductive alkylators such as mitomycin, procarbazine, dacarbazine and altretamine); DNA strand-breakage agents (e.g., bleomycin); topoisomerase II inhibitors (e.g., amsacrine, menogaril, amonafide, dactinomycin, daunorubicin, N,N-dibenzyl daunomycin, ellipticine, daunomycin, pyrazoloacridine, idarubicin, mitoxantrone, m-AMSA, bisantrene, doxorubicin (adriamycin), deoxydoxorubicin, etoposide (VP-16), etoposide phosphate, oxanthrazole, rubidazone, epirubicin, bleomycin, and teniposide); DNA minor groove binding agents (e.g., plicamydin); antimetabolites (e.g., folate antagonists such as methotrexate and trimetrexate); pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea);

anthracyclines; and tubulin interactive agents (e.g., vincristine, vinblastine, and paclitaxel (Taxol®)).

The following examples are provided to illustrate certain embodiments of the invention. They are not intended to limit the invention in any way.

EXAMPLE 1

Sarcomas are a diverse class of malignancies that represent a significant challenge in oncology. Ewing sarcoma is the second most common bone sarcoma, and typically affects individuals in the first two decades of life (Biswas, et al. (2016) World J. Orthop., 7:527-38). Although patients with localized disease experience 5-year survival rates of 75%, patients with metastatic disease face a dismal survival probability of approximately 20%. Thus, there is an urgent need to identify biomarkers that can predict recurrence and response to therapy, and develop strategies to combat metastatic disease.

The key etiologic agent in Ewing sarcoma is a translocation product that fuses the EWS RNA-binding protein with an Ets family transcription factor, most commonly FLI1 (Cidre-Aranaz, et al. (2015) Front. Oncol., 5:162). Sustained EWS-FLI1 activity is required for transformation, and significant efforts have been aimed at identifying its critical targets. Multiple effectors that contribute to pathogenesis have been identified, both in cultured cells in vitro and in murine models. Furthermore, therapeutics have been developed against some of these effectors, including IGF, VEGF, and EWS-FLI1 itself (Gaspar, et al. (2015) J. Clin. Oncol., 33:3036-46; Toomey, et al. (2010) Oncogene 29:4504-16). However, their clinical efficacy has been limited, underscoring the need to identify novel targets and approaches for Ewing sarcoma treatment.

The ubiquitin-specific protease 6 (USP6) oncogene is translocated in multiple benign mesenchymal tumors, including primary aneurysmal bone cyst (ABC), and nodular fasciitis (Oliveira, et al. (2004) Cancer Res., 64:1920-3; Erickson-Johnson, et al. (2011) Lab. Invest., 91:1427-33). USP6 translocations were also identified in fibroma of tendon sheath and giant-cell rich granuloma (Agaram, et al. (2014) Hum. Pathol., 45:1147-52; Carter, et al. (2016) Mod. Pathol., 8:865-9). In all cases, translocation resulted in promoter swapping and high-level expression of wild-type USP6. USP6 expression is normally highly restricted in adult human tissues, with significant levels observed only in testes (Paulding, et al. (2003) Proc. Natl. Acad. Sci., 100:2507-11). Although USP6 was first cloned in 1992 (Nakamura, et al. (1992) Oncogene 7:733-41), until recently, little was known regarding its molecular functions, either physiologically or during tumorigenesis. When ectopically expressed in candidate cells of origin for ABC and nodular fasciitis (i.e., fibroblasts and preosteoblasts), USP6 induces formation of tumors that recapitulate key clinical, histologic, and molecular features of the human tumors (Pringle, et al. (2012) Oncogene 31:3525-35; Ye, et al. (2010) Oncogene 29:3619-29; Lau, et al. (2010) J. Biol. Chem., 285:37111-20), with its catalytic activity as a deubiquitylating enzyme being essential (Ye, et al. (2010) Oncogene 29:3619-29). USP6 promotes tumorigenesis through multiple pathways, including Jak1/STAT3, Wnt/b-catenin, and NFkB (Pringle, et al. (2012) Oncogene 31:3525-35; Madan, et al. (2016) Proc. Nat. Acad. Sci., 113:E2945-54; Quick, et al. (2016) Cancer Res., 76:5337-47). Within the Jak1/STAT3 pathway, Jak1 itself is the critical target of USP6 (Quick, et al. (2016) Cancer Res., 76:5337-47). Deubiquitylation of Jak1 by USP6 rescues it from proteasomal degradation, leading to greatly elevated levels of the kinase, and sensitizing cells to Jak1 agonists such as IL6 (Quick, et al. (2016) Cancer Res., 76:5337-47).

Although translocation-driven overexpression of USP6 plays a key role in benign neoplasms, its role in malignant entities where it is not the oncogenic driver remains unexplored. It is often incorrectly cited that USP6 is widely expressed in cancer cell lines. However, this erroneous conclusion is based on an early study in which Northern probes cross-reacted with the highly related, widely expressed USP32 gene (Nakamura, et al. (1992) Oncogene 7:733-41). Later reverse transcription-quantitative PCR (RT-qPCR) of primary tumors with USP6-specific primers indicated that its expression is far more restricted: high USP6 expression appears to occur predominantly in tumors of mesenchymal origin (Oliveira, et al. (2005) Oncogene 24:3419-26). Yet, to date, there have been few publications exploring USP6 functions in malignant cells, with most in HeLa cells (Madan, et al. (2016) Proc. Nat. Acad. Sci., 113:E2945-54; Masuda-Robens, et al. (2003) Mol. Cell Biol., 23:2151-61; Rueckert, et al. (2012) Biol. Cell., 104:22-33; Li, et al. (2017) Mol. Cell. Biol., 38:e00320-17; Funakoshi, et al. (2014) J. Cell. Sci., 127:4750-61).

The functions of USP6 were investigated in Ewing sarcoma, one of the malignancies shown to express high levels (Oliveira, et al. (2005) Oncogene 24:3419-26). Herein, it is shown that USP6 triggers a gene signature reflective of response to IFN, a Jak1 agonist that functions in immunity. USP6 renders Ewing sarcoma cells exquisitely sensitive to exogenous IFNs: not only is STAT1-mediated gene expression dramatically potentiated in USP6-expressing cells by IFN treatment, but Type I IFN is selectively cytotoxic to USP6-positive but not USP6-negative Ewing sarcoma cells. IFN-induced death is mediated by TRAIL, a potent proapoptotic ligand. This represents one of the first studies to examine USP6 functions in malignant cells, and indicates that it might serve as a prognostic indicator for response of Ewing sarcoma to IFN treatment.

Materials and Methods

Cell Lines and CRISPR-Mediated Gene Targeting

RD-ES and TC-71 were obtained from National Cancer Institute (Bethesda, MD) and Children's Hospital of Los Angeles, Keck School of Medicine (Los Angeles, CA), respectively. CHLA-10 and SK-N-MC were obtained from Perelman School of Medicine at the University of Pennsylvania (Philadelphia, PA). Lines expressing USP6 in a doxycycline-inducible manner were generated as described (Ye, et al. (2010) Oncogene 29:3619-29). Cells were tested for mycoplasma every 3 to 6 months, and prophylactically maintained in Mycoplasma Removal Agent (MP Biomedicals #09350044) for 2 weeks after thawing. All experiments used cells maintained for fewer than 20 passages after thawing. Cell line identity was confirmed by short tandem repeat analysis just prior to manuscript submission.

Validated CRISPR target sequences for Jak1, STAT1, and STAT3 were from published sequences (Sanjana, et al. (2014) Nat. Methods 11:783-4). Target gRNAs [Jak1 (CACCGTCCCATACCTCATCCGGTAG; SEQ ID NO: 3), STAT1 (CACCGTCCCATTACAGGCTCAGTCG; SEQ ID NO: 4), and STAT3 (CACCGAGATTGCCCGGATTGTGGCC; SEQ ID NO: 5)] were subcloned into LentiCRISPRv2 (Addgene #52961) as described (Sanjana, et al. (2014) Nat. Methods 11:783-4). USP6/RD-ES cells were transfected with CRISPR constructs and subjected to puromycin selection. Clones were screened by immunoblotting.

Reagents

Doxycycline was obtained from ClonTech (#8634-1). Jak Inhibitor I (CAS 457081-03-7; #420099) and PS-1145 (P6624) were obtained from Sigma-Aldrich. Lipofectamine 2000 was obtained from Life Technologies. IFNα, IFNβ, and IFNγ were obtained from PBL Assay Science (#11410-2 and #11200-1) and PeproTech (#300-02), respectively. ZVAD (FMK001) and IETD (FMK007) were obtained from R&D Systems. TRAIL (catalog no. 752904) and anti-TRAIL (catalog no. 308202) were obtained from BioLegend. Caspase-3/7 (#G8090) and caspase-9 (#G8210) activation kits were purchased from Promega, and assays were performed on Molecular Devices SpectroMax. Annexin V staining kit was obtained from eBioscience (#88-8007-72), and samples were analyzed on BD Biosciences Accuri C6 and LSR II machines.

Immunoblotting and qRT-PCR

Cell lysis was performed as described (Sanjana, et al. (2014) Nat. Methods 11:783-4). Jak1 (cs-3332), pSTAT1 (cs-9167), pSTAT3 (cs-9145), TRAIL (cs-3219), PARP (cs-9542), caspase-8 (cs-9746), and Bid (cs-2002) were obtained from Cell Signaling Technology. HA (sc-805), STAT1 (sc-346), STAT3 (sc-482), and p65 (sc-372) were obtained from Santa Cruz Biotechnology. Erk antibody was obtained from Weill Cornell Medical College (New York, NY). Quantification was performed using the Image Studio Lite. TRIzol was used for RNA isolation, and qPCR was performed using SYBR Green (catalog no. 436765, Thermo Fisher Scientific). Erk, STAT3, and p65 were used as protein-loading controls as described (Hwang, et al. (2005) J. Biol. Chem., 280:12758-65; Huang, et al. (2004) J. Biol. Chem., 279:13866-77; Banerjee, et al. (2010) Cancer Res., 70:1356-66; Chien, et al. (2011) Genes Dev., 25:2125-36); their levels were comparable across conditions as shown.

Gene Expression Profiling/pathway Analysis and DNA Methylation

RNA was isolated from USP6/RD-ES cells treated with or without doxycycline and IFNα for 24 hours. RNA sequencing (RNA-seq), alignment, processing, and repository deposit was performed by the University of Pennsylvania Next-Generation Sequencing Core (GSE107307). The CDF files for the Affymetrix U133A and U133 Plus 2.0 arrays were edited to remove probes from the USP6 probe set (206405_x_at) that cross-reacted with USP32 or other genes. This refined USP6-specific probe set comprised Probe 4, 8, 9, and 11. Publicly available Ewing sarcoma datasets [GSE7007 (Tirode, et al. (2007) Cancer Cell 11:421-9) and GSE37371 U133A (Martignetti, et al. (2012) PLoS One, 7:e41770)] were sorted by USP6 expression. Patients with the highest USP6 levels were compared to those with the lowest (5 per group). For the germ cell tumor dataset GSE10615 (Palmer, et al. (2008) Cancer Res., 68:4239-47), samples were segregated as seminomas ($USP6^{high}$) versus yolk sac tumors ($USP6^{low}$). Gene Set Enrichment Analysis (GSEA) was performed as described previously, using the "Hallmarks" molecular signature database. Gene expression analysis in nodular fasciitis was compared with other USP6-nonexpressing mesenchymal tumors, as described (Quick, et al. (2016) Cancer Res., 76:5337-47).

DNA methylation datasets for five Ewing sarcoma cell lines (CADO-ES1, SK-NMC, A673, RD-ES, and SK-ES-1) were procured from the Cancer Cell Line Encyclopedia (CCLE; portals.broadinstitute.org/ccle; Barretina, et al. (2012) Nature 483:603-7; Cancer Cell Line Encyclopedia Consortium (2015) Nature 528:84-7), and relative CpG methylation for various genes was plotted using GraphPad. Methylation probe IDs for the USP6 promoter were obtained from MExpress (Koch, et al. (2015) BMC Genomics 16:636) and used in conjunction with GSE89041 (Huertas-Martinez, et al. (2017) Cancer Lett., 386:196-207).

Results

USP6 Triggers an IFN Response in Ewing Sarcoma in Patient Samples and Cultured Cells Little is known about how USP6 functions in the context of malignant cells where it is not the oncogenic driver, with only a handful of reports largely restricted to HeLa (Madan, et al. (2016) Proc. Nat. Acad. Sci., 113:E2945-54; Masuda-Robens, et al. (2003) Mol. Cell Biol., 23:2151-61; Rueckert, et al. (2012) Biol. Cell., 104: 22-33; Li, et al. (2017) Mol. Cell. Biol., 38:e00320-17; Funakoshi, et al. (2014) J. Cell. Sci., 127:4750-61). As mentioned, USP6 expression in neoplasms is far more restricted than initially believed: screening of a broad panel of primary samples demonstrated that high expression was predominantly confined to tumors of mesenchymal origin, including Ewing sarcoma (Oliveira, et al. (2005) Oncogene 24:3419-26).

To explore what functions USP6 might have in Ewing sarcoma, gene expression patterns were investigated in primary patient samples. Most large Ewing sarcoma patient datasets utilize Affymetrix microarrays, which use probe sets consisting of 11 distinct probes against a given gene. However, most probes in the USP6 probeset (206405_x_at) cross-reacted with USP32 or other genes. Therefore, GSEA analysis was refined to use only the USP6-specific subset of probes, comparing Ewing sarcoma tumors with the highest versus lowest levels of USP6 expression. From two independent patient datasets, IFNα (type I) and IFNγ (type II) responses emerged among the top signatures associated with high USP6 expression (FIG. 1A). In addition, the IL6/Jak/STAT3 pathway was potently activated.

To determine whether USP6 directly induces these gene signatures, mechanistic studies were performed in immortalized Ewing sarcoma cells. However, none of the commonly used Ewing sarcoma lines expressed appreciable USP6 levels. Extensive CpG methylation was found across the USP6 promoter in all immortalized Ewing sarcoma cell lines examined, while comparatively low methylation was observed in primary Ewing sarcoma tumors. CpG methylation heatmaps revealed significant silencing of USP6 in multiple Ewing sarcoma cell lines relative to genes known to be highly expressed in Ewing sarcoma, such as Myc and EZH2. How USP6 becomes methylated upon cell immortalization is unknown, but regardless, this necessitated expression of USP6 ectopically. Clonal and pooled stable lines expressing varied levels of USP6 in a doxycycline-inducible manner were generated in the patient-derived Ewing sarcoma cell line, RD-ES (FIG. 1B). USP6 induced dose-dependent upregulation of the Jak1 kinase (which is stabilized by direct deubiquitylation by USP6) and phosphorylation of STAT3 (FIG. 1B), similar to that observed in models of ABC and nodular fasciitis (Quick, et al. (2016) Cancer Res., 76:5337-47). In addition, robust phosphorylation of STAT1, the key STAT family member that mediates IFN signaling, was observed (FIG. 1B). RNA-seq was performed comparing the pooled cell line, USP6/RD-ES, in the presence versus absence of doxycycline. As in primary Ewing sarcoma samples, IFNα and IFNγ responses emerged as the top "hits," followed by IL6/Jak/STAT3 activation (FIG. 1A). Together, these results demonstrate that not only is USP6 associated with an IFN response in Ewing sarcoma in vivo, but that it is sufficient to activate this pathway. They also validate that the RD-ES cell model faithfully reflects physiologic USP6 functions in Ewing sarcoma patient samples.

It was then explored whether USP6 was associated with an IFN response in other tumor types. An IFN signature was also induced in nodular fasciitis, which is driven by translocation-driven overexpression of USP6 (FIG. 1A). In addition, USP6 expression was associated with an IFN response in germ-cell tumors. Yolk sac tumors (i.e., germ-cell tumors arising from cells lining the yolk sac that are normally destined to become ovaries or testes) uniformly express low USP6 levels, whereas seminomas (i.e., germ cell tumors arising from the germinal epithelium of the testes) exhibit high levels (FIG. 1C). GSEA comparing seminomas to yolk sac tumors revealed that high USP6 expression was again correlated with IFN and Jak-STAT3 signatures (FIG. 1A). Together, these results indicate that USP6 is more broadly associated with an IFN response in human tumors.

USP6 Sensitizes Ewing Sarcoma Cells to Exogenous IFN Treatment

In addition to triggering an IFN response by itself, USP6 can render RD-ES hypersensitive to exogenous IFN due to the elevated Jak1 levels. Indeed, dramatic enhancement and prolongation of STAT1/3 activation in USP6/RD-ES cells were observed with Type I and II IFNs (IFNα/IFNβ and IFNγ, respectively; FIG. 2). Treatment of parental RD-ES cells with IFNα or IFNγ induced phosphorylation of STAT1 and STAT3, which peaked within 30 minutes and gradually declined by 8 hours. In contrast, STAT1 and STAT3 phosphorylation was augmented and prolonged in USP6/RD-ES, with significant activation persisting at 8 hours (FIGS. 2A and B). Interestingly, type I IFNs induced downregulation of USP6 (FIG. 2A).

Figure 2B:
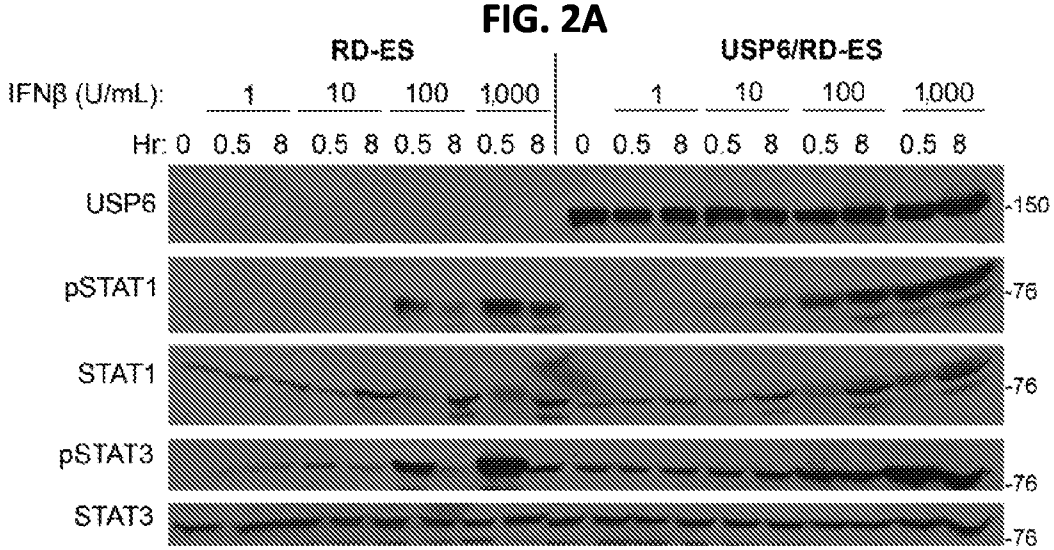

In addition to prolonging STAT1/3 activation, USP6 heightened sensitivity to low-dose IFN (FIG. 2B). At doses ranging from 10 to 1,000 U/mL, USP6/RD-ES cells showed elevated STAT1/3 phosphorylation compared with parental RD-ES. The ability of USP6 to enhance and/or prolong STAT activation was confirmed in three additional patient-derived Ewing sarcoma lines, TC-71, CHLA-10, and SKN-MC, indicating that its effects are widely observed in Ewing sarcoma, and are not a peculiarity of the RD-ES line.

Figure 3A:
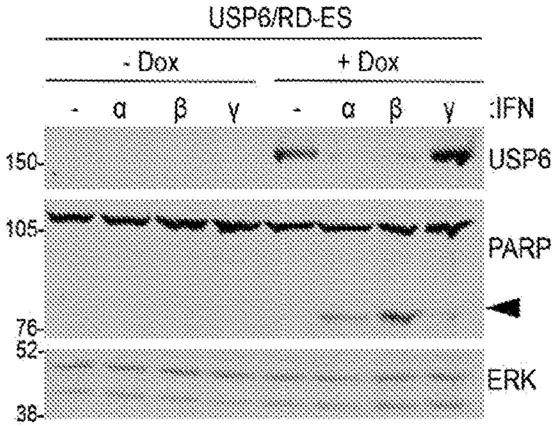
FIGS. 3A-3F show that USP6 renders Ewing sarcoma cells sensitive to apoptosis by type I IFN. USP6/RD-Ewing sarcoma cells were grown in the absence or presence of doxycycline (dox), then treated with the indicated IFN at 1,000 U/mL for 24 hours. Cells were subjected to blotting (FIG. 3A), or Trypan blue exclusion assays to monitor viability (n=3) (FIG. 3B).
Figure 3B:
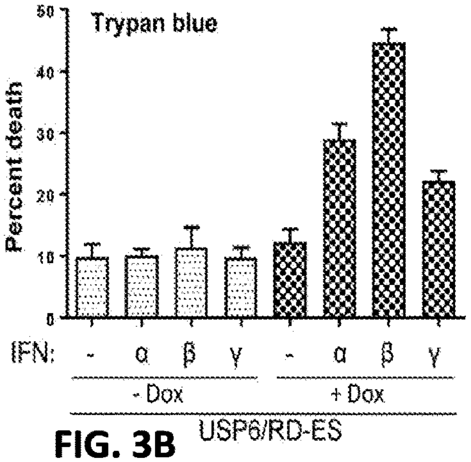
Figure 3C:
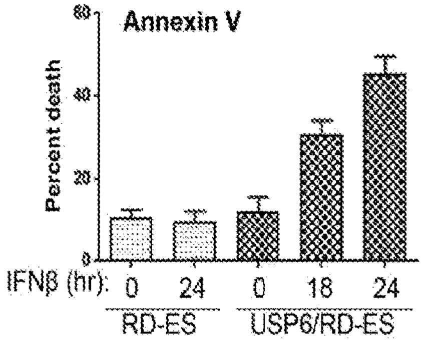
Figure 3D:
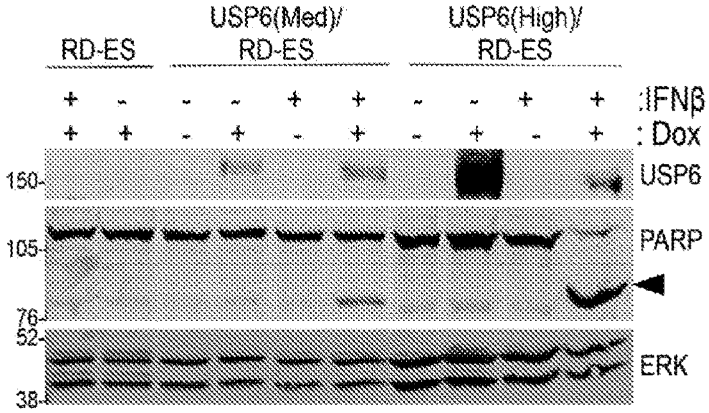
Figure 3E:
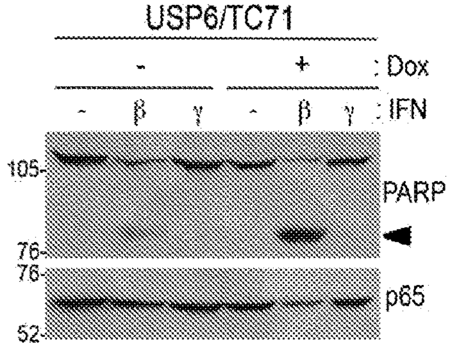
Figure 3F:
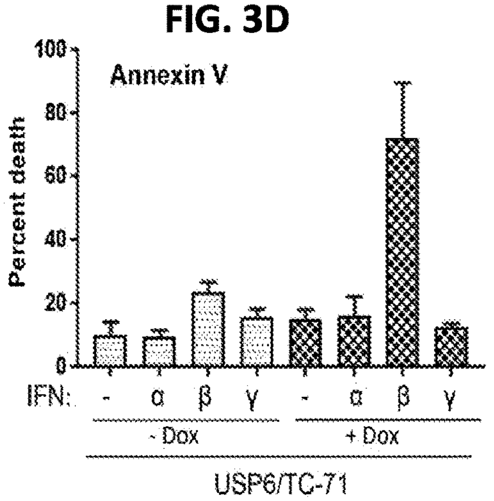

Strikingly, with prolonged treatment, type I IFN was selectively cytotoxic to USP6-expressing but not parental RDES cells. IFNβ exhibited the greatest cytotoxicity, followed by IFNα, then IFNγ, as monitored by PARP cleavage and Trypan blue exclusion (FIGS. 3A and B). Annexin V staining confirmed that IFNβ-induced death occurred through apoptosis (FIG. 3C). IFNβ induced apoptosis more effectively than IFNα at doses up to 2,500 U/mL, likely due to its greater affinity for the type I IFN receptor. Furthermore, USP6 conferred sensitivity to IFNβ in a dose-dependent manner, as the extent of death correlated with the level of USP6 expression (FIG. 3D). USP6 also sensitized TC-71 cells to IFNβ-induced apoptosis (FIGS. 3E and F). However, USP6 minimally enhanced death in CHLA-10 cells and SK-N-MC cells. Notwithstanding, these results indicate that USP6 can dictate the magnitude of response to IFN, and can greatly sensitize ES cells to the apoptotic potential of IFN.

IFN-induced Apoptosis Involves Extrinsic and Intrinsic Pathways, and Requires Jak1-STAT1/3

Depending on cell type, IFN can trigger extrinsic apoptosis, which occurs through ligand binding to cell surface receptors, or intrinsic apoptosis, which occurs through mitochondrial dysregulation. These pathways can be distinguished by their requirement for distinct caspase proteases. Extrinsic apoptosis requires cleavage/activation of caspase-8, followed by caspase-3/7; intrinsic apoptosis entails cleavage of the mitochondrial protein, Bid, and caspase-9 activation, which also triggers caspase-3/7 activation. However, in some circumstances extrinsic apoptosis induced by IFN can feed into the mitochondrial route, and trigger cleavage/activation of Bid and caspase-9.

Figure 4A:
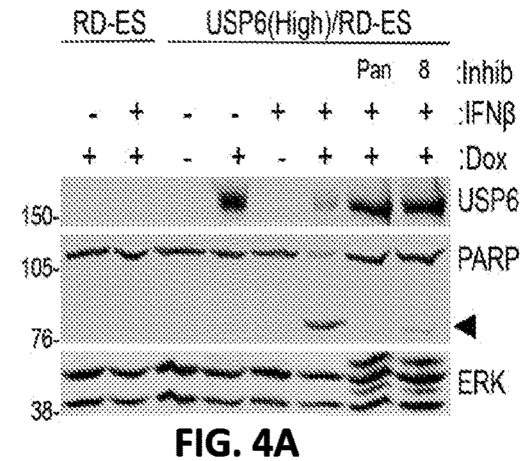
FIGS. 4A-4F show that IFNβ-induced apoptosis requires Jak1-STAT1/STAT3 and entails extrinsic and intrinsic death pathways.
Figure 4C:
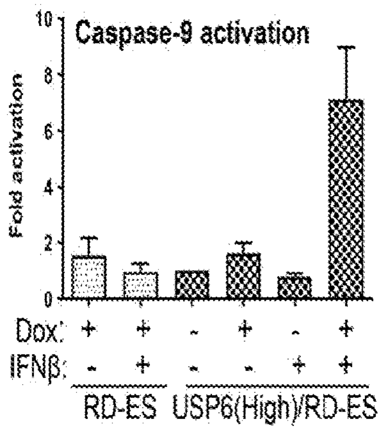
Figure 4B:
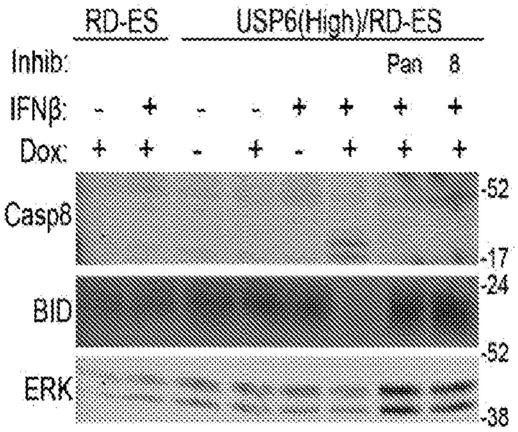
Figure 4D:
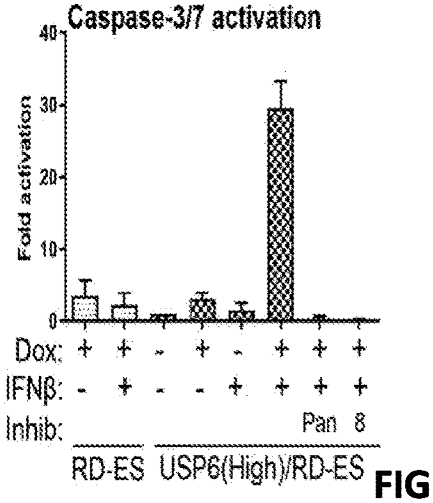

IFN-induced death of USP6/RD-ES was blocked by the caspase-8-specific inhibitor, IETD (FIG. 4A), and was accompanied by caspase-8 cleavage (FIG. 4B), implicating the extrinsic pathway. However, IFNβ also induced Bid cleavage (FIG. 4B) and caspase-9 activation (FIG. 4C), indicating engagement of the mitochondrial route. Activation of Caspase-3/7 was also observed, and could be blocked by caspase-8 inhibitor (FIG. 4D). In sum, these data indicate that IFNβ-induced death of USP6/RD-ES cells occurs through a cell surface-mediated, extrinsic route that entails mitochondrial dysregulation.

Figure 4E:
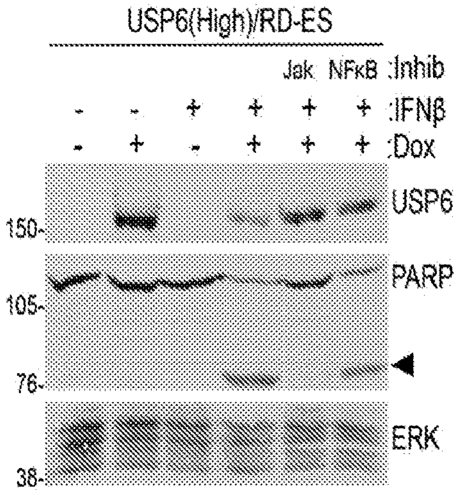
Figure 4F:
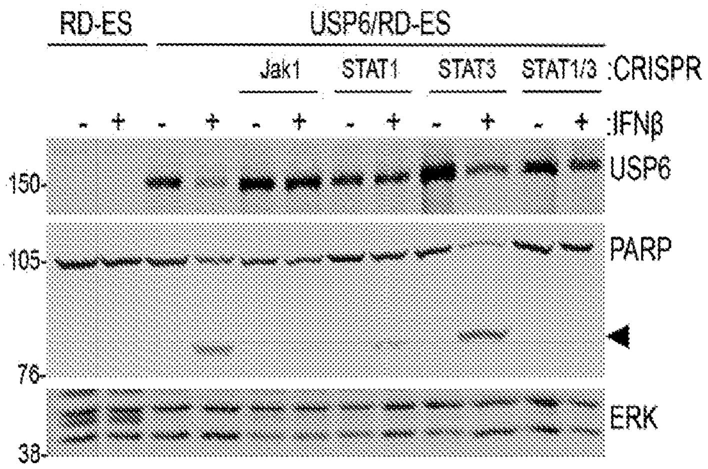

To further dissect the signaling mechanisms underlying apoptosis, the roles of Jak1-STAT and NFkB were examined, both of which have been shown to participate in IFN-mediated death (Hwang, et al. (2005) J. Biol. Chem., 280:12758-65; Huang, et al. (2004) J. Biol. Chem., 279: 13866-77). A pan-Jak family inhibitor completely blocked apoptosis of USP6/RD-ES, whereas the NFkB inhibitor was ineffective (FIG. 4E). Reporter assays confirmed that the NFkB inhibitor was functional. To confirm the requirement of the Jak1/STAT pathway, CRISPR-mediated knockouts of Jak1, STAT1, and STAT3 were generated in USP6/RD-ES cells (FIG. 4F). FIG. 4F shows that Jak1 deletion significantly reduced death. Deletion of both STAT1 and STAT3 was required to obtain robust inhibition of death, indicating that they play distinct roles in the apoptotic response, consistent with their ability to function as homo- and heterodimers in response to IFN. These genetic and pharmacologic approaches demonstrate that Jak1, STAT1, and STAT3 are required for IFNβ-mediated apoptosis of USP6/RD-ES.

IFNβ-induced Apoptosis of USP6/RD-ES Cells is Mediated by TRAIL Pathway

Figure 5A:
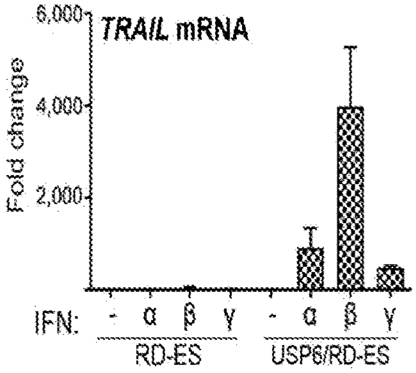
FIGS. 5A-5G show that IFNβ induces apoptosis of USP6-positive Ewing sarcoma cells through synergistic production of TRAIL.

IFN can induce expression of the proapoptotic ligands, FasL and TRAIL. The RNA-seq data indicated that TRAIL, but not Fas, was synergistically induced by IFN in USP6/RD-ES relative to parental cells. RT-qPCR confirmed that IFNs had little or no effect on TRAIL expression in RD-ES (FIG. 5A). However, TRAIL mRNA levels were dramatically increased in USP6/RD-ES treated with IFNβ. Induction was also observed, but to a much lesser degree, with IFNα and IFNγ (FIG. 5A), correlating with the extent of death induced by each (FIG. 3). In contrast, FasL expression was not significantly affected by USP6. Expression of the five TRAIL receptors was also examined, both the active (DR4/DR5) and inactive decoy (TNFRSF10C/D and OPG) forms, whose balance has been shown to a play an important role in sensitization of cancer cells to TRAIL-induced apoptosis (von Karstedt, et al. (2017) Nat. Rev. Cancer 17:352-66). USP6 did not alter expression of receptors in a manner consistent with sensitization to death.

Figure 5B:
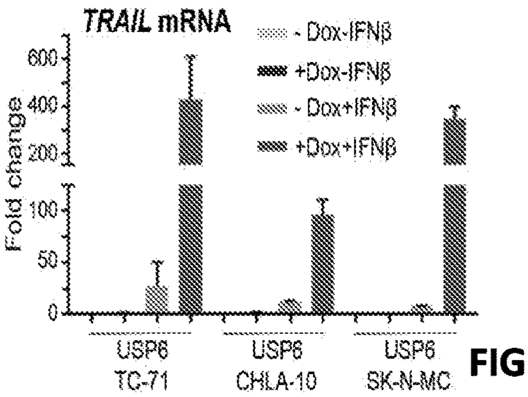
Figure 5C:
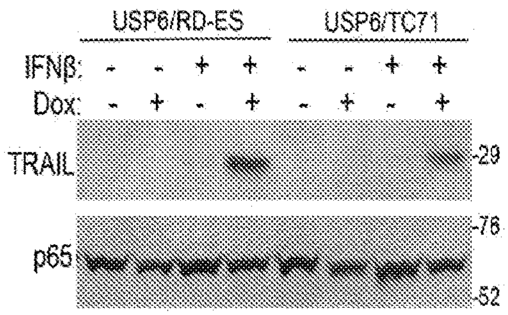
Figure 5E:
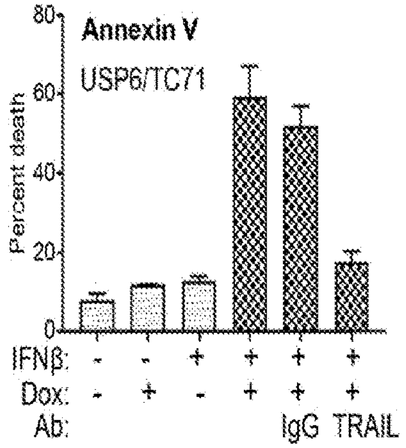
Figure 5D:
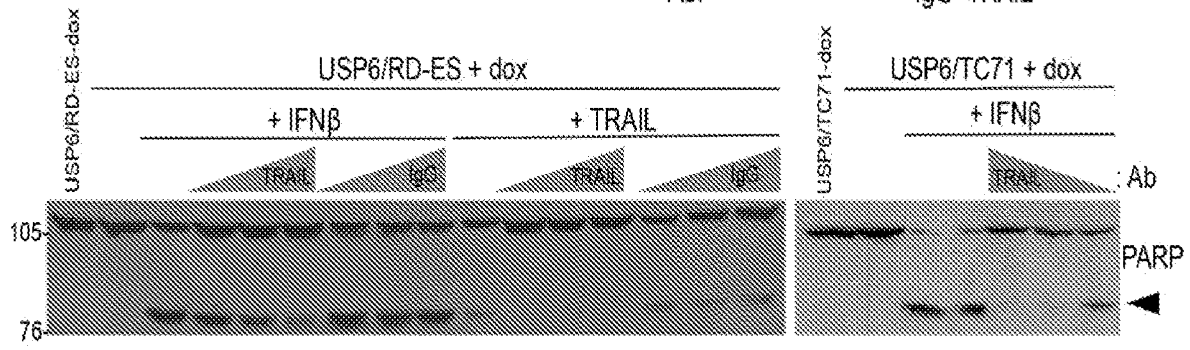
Figure 5F:
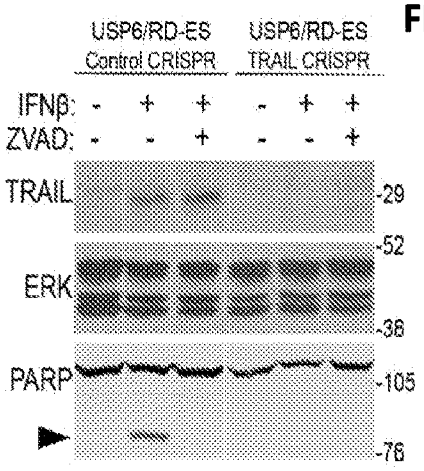

FIG. 5C confirms that TRAIL protein was strongly induced upon IFNβ treatment in USP6/RD-ES in a doxycycline-dependent manner. Induction of TRAIL transcription and protein was also confirmed in the USP6/TC-71 Ewing sarcoma cell line (FIGS. 5B and C). Neutralizing anti-TRAIL antibody inhibited IFNβ-induced apoptosis of both of USP6/RD-ES and USP6/TC-71 cells, as measured by PARP cleavage and Annexin V staining (FIGS. 5D and E). Furthermore, CRISPR-mediated deletion of TRAIL completely abrogated death of USP6/RD-ES by IFNβ (FIG.

5F). These data confirm that TRAIL plays a dominant role in mediating IFNβ-induced apoptosis of USP6-positive Ewing sarcoma cells.

Figure 5G:
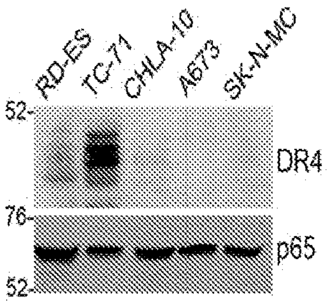

As described above, the various Ewing sarcoma lines exhibited differential sensitivities to IFNβ-induced apoptosis in the presence of USP6: RD-ES and TC-71 were very sensitive, while CHLA-10 and SK-N-MC were largely unresponsive (FIG. 3). To determine whether this was due to disparate induction of TRAIL in these lines, qRT-PCR was performed. However, TRAIL transcription was also synergistically induced in insensitive Ewing sarcoma lines (FIG. 5B). It was then explored whether the differential responsiveness might arise from varied expression of TRAIL receptor. Strikingly, it was found sensitivity to IFNβ in the presence of USP6 correlated precisely with expression of the TRAIL receptor DR4: DR4 levels were highest in RD-ES and TC-71, and largely undetectable in the insensitive Ewing sarcoma lines (FIG. 5G).

IFN Triggers USP6 Downregulation Through TRAIL-Dependent Caspase Activation

Figure 6A:
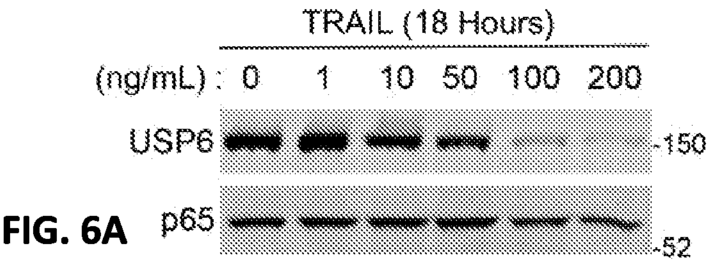
FIGS. 6A-6D show that Type I IFN induces USP6 downregulation through a TRAIL- and caspase-mediated mechanism.
Figure 6B:
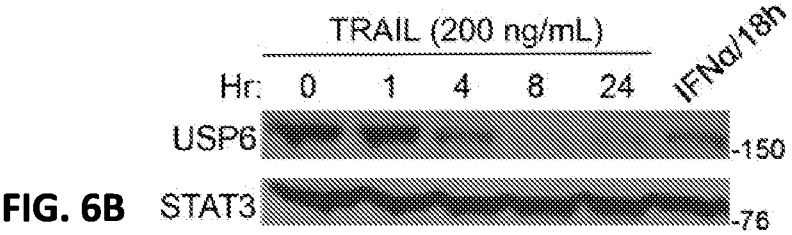
Figure 6C:
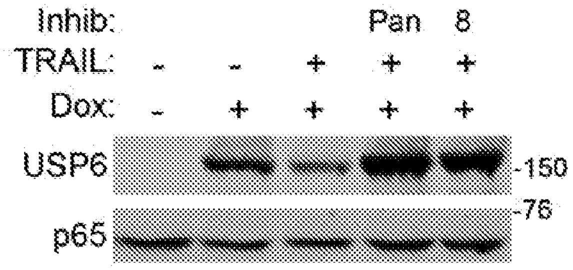
Figure 6D:
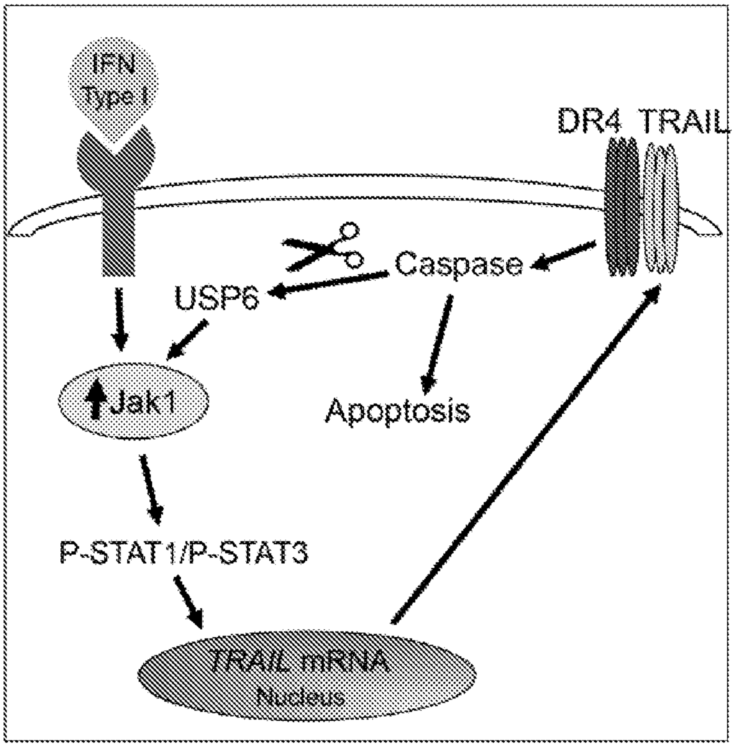

As mentioned above, type I IFNs induce downregulation of USP6 protein (FIGS. 2,3,4). TRAIL also triggered USP6 downregulation, in a time- and dose-dependent manner (FIGS. 6A and B). TRAIL acted more rapidly, with USP6 downregulation observed within 4 hours, whereas IFNβ required 12 to 18 hours (FIGS. 2A and 6B). Because caspases play a key role in TRAIL signaling, it was tested whether they mediate USP6 downregulation. Both the pan-caspase inhibitor ZVAD and the caspase-8 inhibitor IETD completely blocked IFNβ- and TRAIL induced USP6 downregulation (FIGS. 4A and 6C, respectively). Together, these results reveal a negative feedback mechanism whereby USP6 induces TRAIL transcription, which then signals through DR4 to trigger caspase-dependent downregulation of USP6 (see Model FIG. 6D). Notably, this identifies type I IFNs and TRAIL as the first physiologic agonists to regulate USP6.

Although it has long been recognized that USP6 plays a key etiologic role in several benign neoplasms, its functions in the biology of malignant entities is poorly understood. Analysis of primary tumor samples revealed that among human malignancies, highest USP6 expression was most commonly observed in mesenchymal cancers, including Ewing sarcoma. The current study is the first to explore functions of USP6 in Ewing sarcoma. USP6 expression is associated with an IFN signature in primary Ewing sarcoma tumors. Furthermore, USP6 is sufficient to trigger this response when inducibly expressed in cultured Ewing sarcoma cells. USP6 also confers exquisite sensitivity of Ewing sarcoma cells to exogenous IFNs. Strikingly, Type I IFNs (particularly IFNβ) induce TRAIL-mediated apoptosis of USP6-positive but not USP6-negative Ewing sarcoma cells, in a DR4-dependent manner (see FIG. 6D for results summary).

To date there are notably few studies on USP6, and thus nothing is known of how its expression is regulated, how its activity modulated, or what normal physiologic processes it participates in. Type I IFNs and TRAIL are identified herein as the first physiologic agonists to induce posttranslational modification of USP6. TRAIL triggers the caspase-dependent processing and downregulation of USP6, and that type I IFN can also trigger this downregulation through induction of TRAIL signaling. This negative feedback loop (wherein USP6 serves to amplify IFN-mediated induction of TRAIL, which then elicits downregulation of USP6) may play an important role during normal physiology to restrict TRAIL-induced functions, which include not only apoptosis but also inflammation (Zoller, et al. (2017) Sci. Rep., 7:5691; Azijli, et al. (2013) Cell Death Differ., 20:858-68).

Along this vein, a key area for future pursuit is determining the consequences of USP6-mediated IFN signaling in Ewing sarcoma pathogenesis. Numerous studies have indicated that IFNs can either promote or antagonize tumor progression across broad tumor types (Bekisz, ET AL. (2013) J. Interferon Cytokine Res., 33:154-61; Wang, E T A L. (2013) J. Interferon Cytokine Res., 33:181-8; Zaidi, et al. (2011) Clin. Cancer Res., 17:6118-24). This complexity can be ascribed to its ability to act not only on tumor cells, but also on immune cells and other cells in the tumor microenvironment. In some scenarios, IFNs can promote an inflammatory microenvironment that enhances proliferation and metastasis of tumor cells (Zaidi, et al. (2011) Clin. Cancer Res., 17:6118-24). In others, IFNs can stimulate immune infiltration and thereby promote tumor-cell killing. Notably, IFNs and TRAIL largely function in an antitumorigenic capacity in Ewing sarcoma, both in vitro and in murine xenografts (Kontny, et al. (2001) Cell Death Differ., 8:506-14; Wietzerbin, et al. (2003) Ann. NY Acad. Sci., 1010:117-120; Picarda, et al. (2010) Clin. Cancer Res., 16:2363-74).

Standard of care for patients with Ewing sarcoma has progressed minimally over the past two decades. General cytotoxic chemotherapy is typically inefficacious in patients with disseminated or recurrent disease. Therefore, essential goals have been to develop novel therapies to prevent and treat recurrent/disseminated disease, and to identify biomarkers that can predict response to therapy. Type I IFN has been explored as a potential therapeutic for several cancers, but its use is currently restricted to advanced cases of melanoma (Wang, et al. (2011) J. Interferon Cytokine Res., 31:545-52). However, its broader use has been limited by severe systemic side effects due to its potent immunostimulatory activity (Wang, et al. (2011) J. Interferon Cytokine Res., 31:545-52). The current results alleviate this issue, because USP6 greatly sensitizes cells to low-dose IFN. Thus, reduced IFN doses can be utilized that would retain tumoricidal activity while minimizing systemic side effects. Furthermore, because USP6 can be associated with an IFN response in other cancers, the findings are applicable to other malignancies in which USP6 is overexpressed.

EXAMPLE 2

Ubiquitin-specific Peptidase 6 (USP6) stimulates the production of numerous immune-stimulatory factors. USP6 is a hominid-specific gene that is highly restricted in most tissues and organs, with only appreciable expression detected in testis. Among malignancies, it is most highly expressed in several sarcomas, including Ewing sarcoma, but it is uncommonly expressed at high levels in other cancers (Oliveira, et al. (2014) Hum. Pathol., 45(1):1-11; Oliveira, et al. (2005) Oncogene 24(21):3419-26). USP6 is the key etiological agent in two benign bone and soft tissue tumors known as aneurysmal bone cyst (ABC) and nodular fasciitis (NF). In NF and ABC, USP6 undergoes a promoter swapping translocation, resulting in sustained high expression of the wild-type protein. The clinical course of NF is peculiar, with rapid growth followed by spontaneous regression over the course of several weeks or months (Erickson-Johnson, et al. (2011) Lab Invest., 91(10):1427-33). NF lesions exhibit abundant infiltration of immune cells, including CD163+ macrophages, and CD8+ and CD4+ T cells, but no $T_{regs}$. The role of USP6 in ABC and NF was investigated, which led to the discovery that USP6 directly de-ubiquitinates and stabilizes the Jak1 kinase (Quick et al. (2016) Cancer Res., 76(18): 5337-47), a key effector in mediating the adaptive and innate immune response.

Figure 7A:
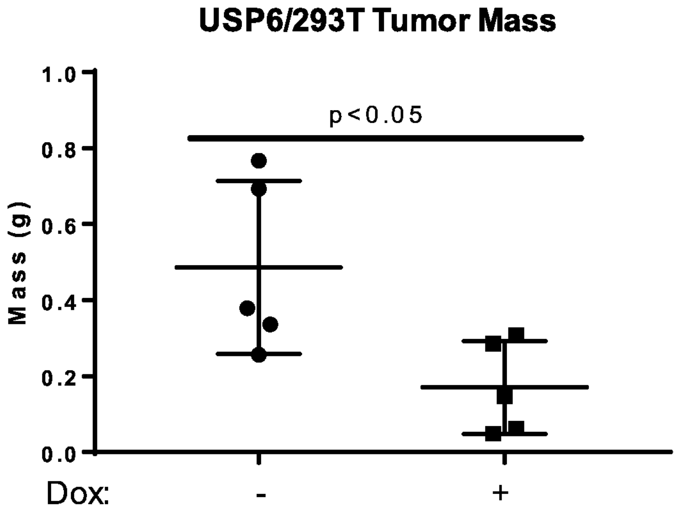
FIG. 7A: USP6 under a doxycycline promoter decreases growth of the tumorigenic cell line 293T in J:NU mice.
Figure 7B:
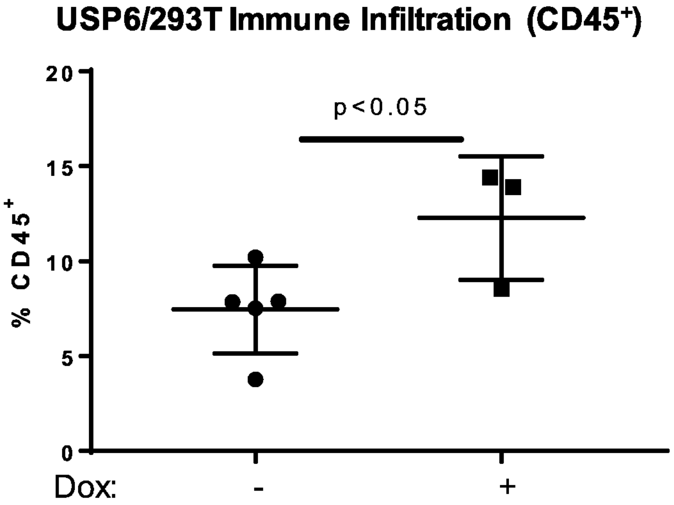
FIG. 7B: USP6 enhances immune cell infiltration (CD45+) in Ewing sarcoma in J:NU mice.
Figure 7C:
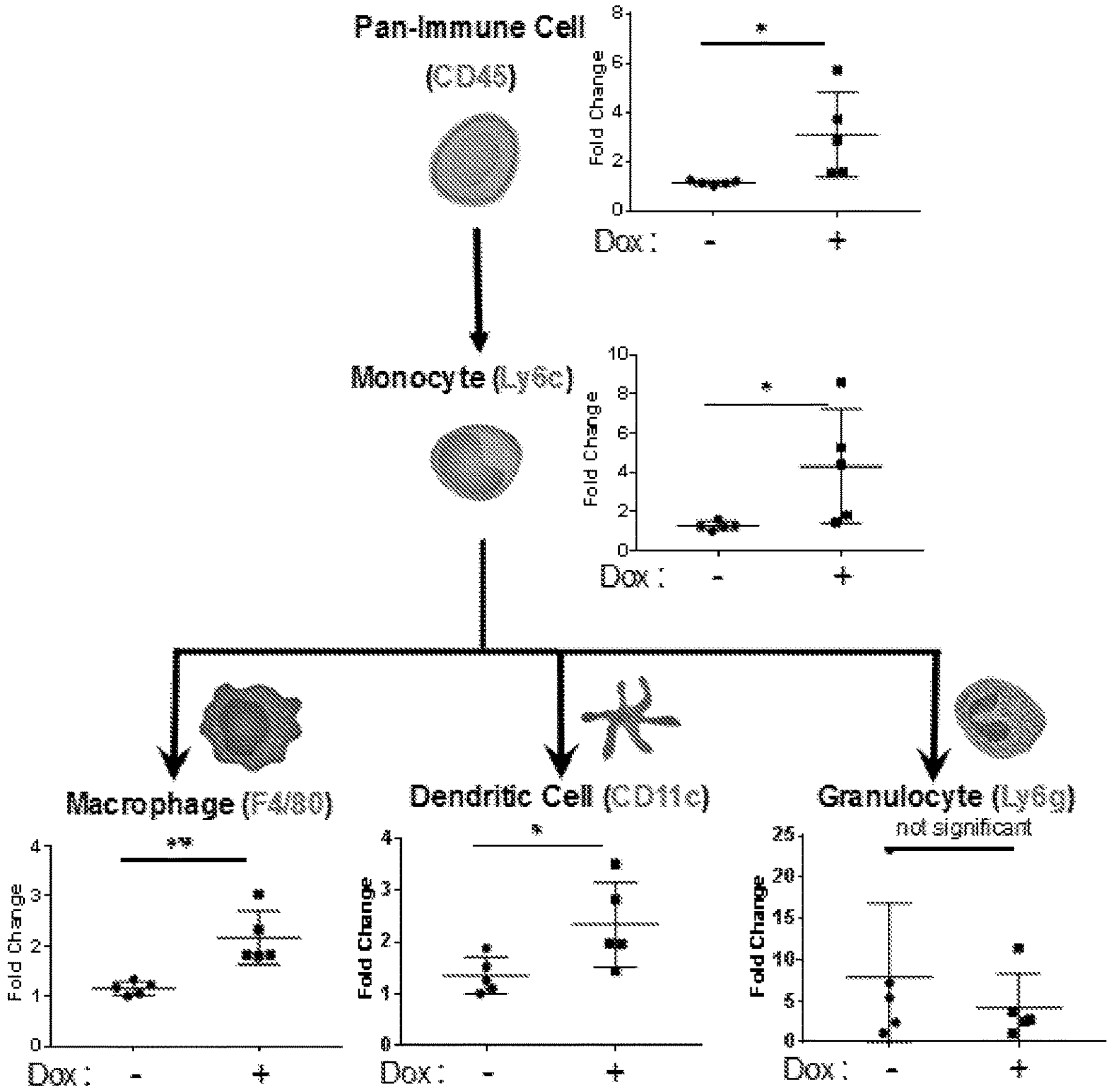
FIG. 7C: USP6 stimulates tumor infiltration of monocyte-derived lineages based on an analysis of Ewing sarcoma xenografts in nude mice.
Figure 7D:
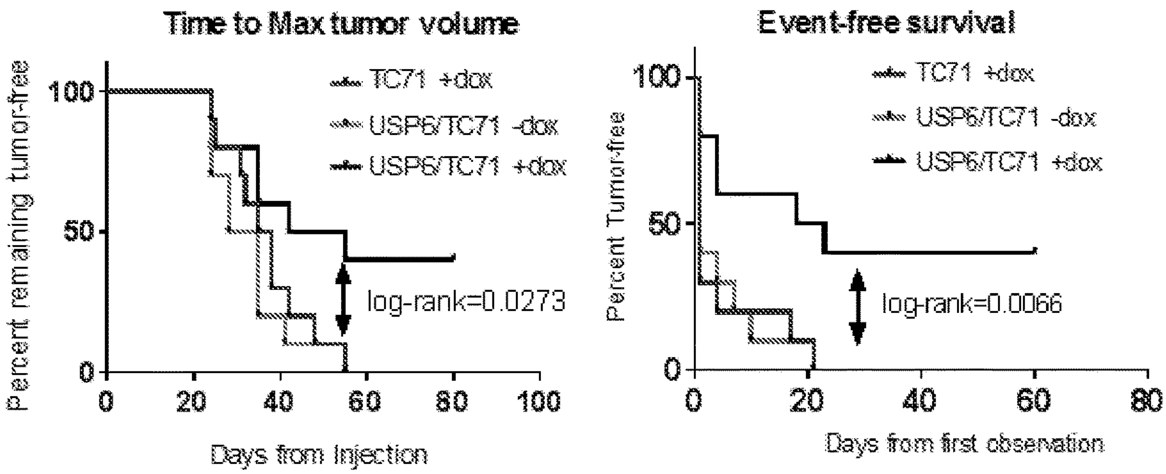
FIG. 7D: USP6 delays tumor growth in nude mice, which retain an innate immune system, and increases survival.
Figure 7E:
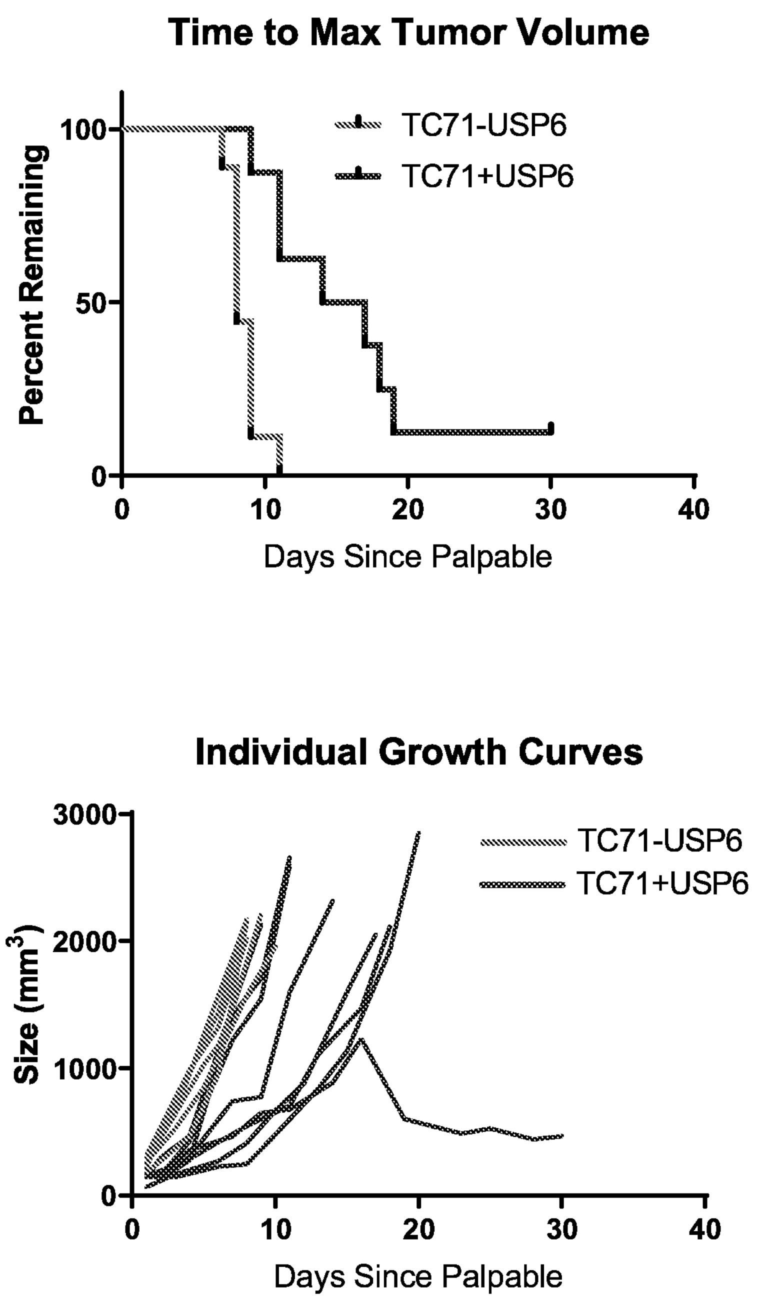
FIG. 7E: Graphs of time to max tumor volume and individual growth curves.
Figure 7F:
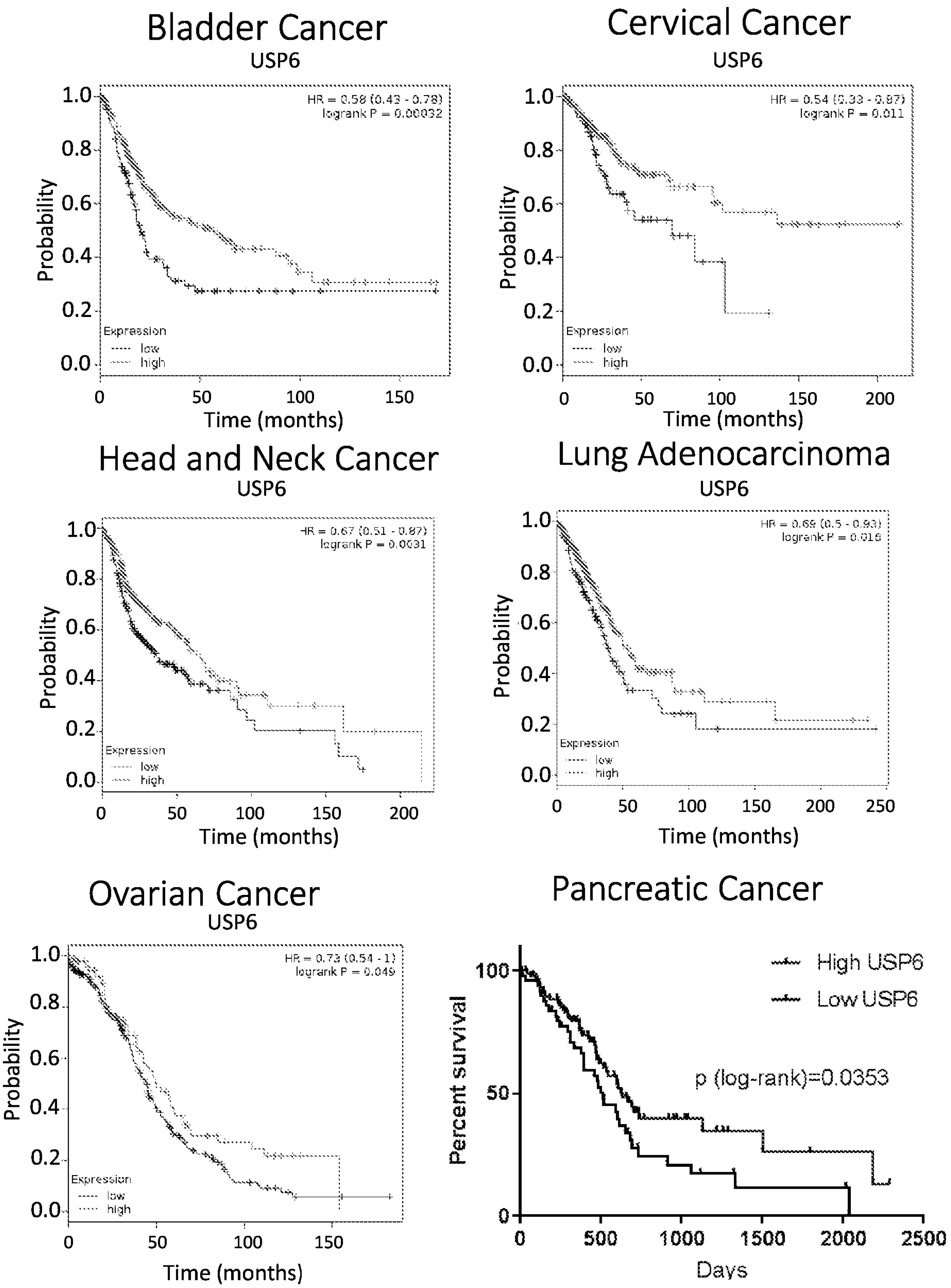
FIG. 7F: High USP6 expression is associated with improved survival in the indicated cancers.

The role of USP6 in Ewing sarcoma, one of the few cancers to have elevated levels of USP6, was also investigated. USP6 was expressed in a doxycycline-inducible manner in the patient-derived sarcoma cell lines A673 and RD-ES. USP6 expression levels were confirmed to approximate those in primary patient tumor samples. High USP6 expression triggers an interferon-response signature and enhances surface MHC Class I expression (Funakoshi, et al. (2014) J. Cell Sci., 127(Pt 21):4750-61) and leads to the production of numerous immune-stimulating factors, including, but not limited to CCL5, CCL20, CXCL9, CXCL10, CXCL11, and TRAIL. Interestingly, cytokines known to promote immune suppression such as CCL2, CXCL8, or CXCL12 are not induced by USP6. Expression of USP6 in Ewing sarcoma attenuates tumor growth (FIG. 7A) and enhances immune cell infiltration in vivo (FIGS. 7B and 7C). USP6 expression induced by dox inhibits growth of xenografted Ewing sarcoma cells (TC71) in nude mice and increases survival (FIG. 7D). As seen in FIG. 7E, USP6 expression increases the time to max tumor volume and slows the growth of tumors. Further, USP6 induces the secretion of factors that increase CD8+ T cell activation in vitro and enhances abundance of mature dendritic cells but reduces abundance of M2 macrophages within the tumor microenvironment. Ewing sarcoma patients with high USP6 expression also have better overall and event-free survival compared to those with low expression, in line with the murine Ewing sarcoma xenograft model. Notably, high USP6 expression is associated with improved survival in a number of other cancers (FIG. 7F).

EXAMPLE 3

Figure 8A:
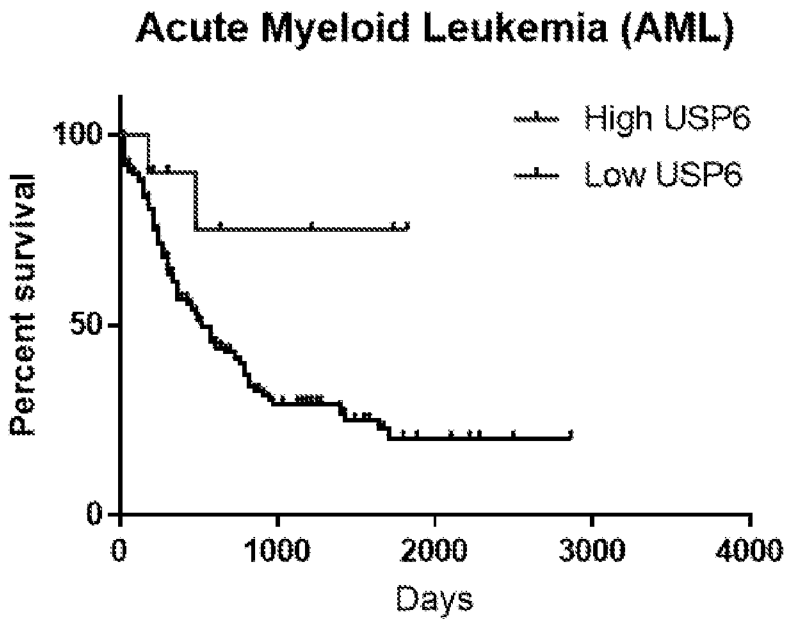
FIG. 8A provides a graph of the survival of acute myeloid leukemia patients based on high or low USP6 expression.
Figure 8B:
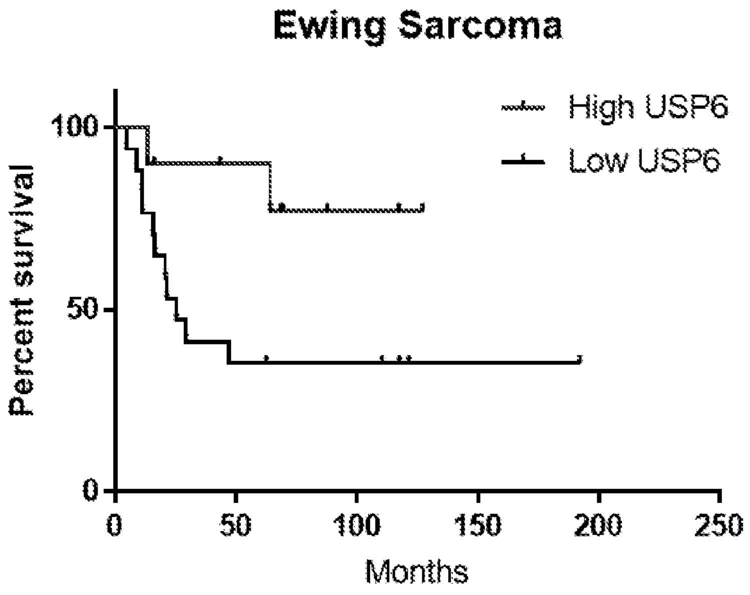
FIG. 8B provides a graph of the survival of Ewing sarcoma patients based on high or low USP6 expression.

As see in FIG. 8A, acute myeloid leukemia patients with high USP6 expression have a significantly improved prognosis. Similarly, FIG. 8B shows that Ewing sarcoma patients with high USP6 expression have a significantly improved prognosis.

Figure 9:
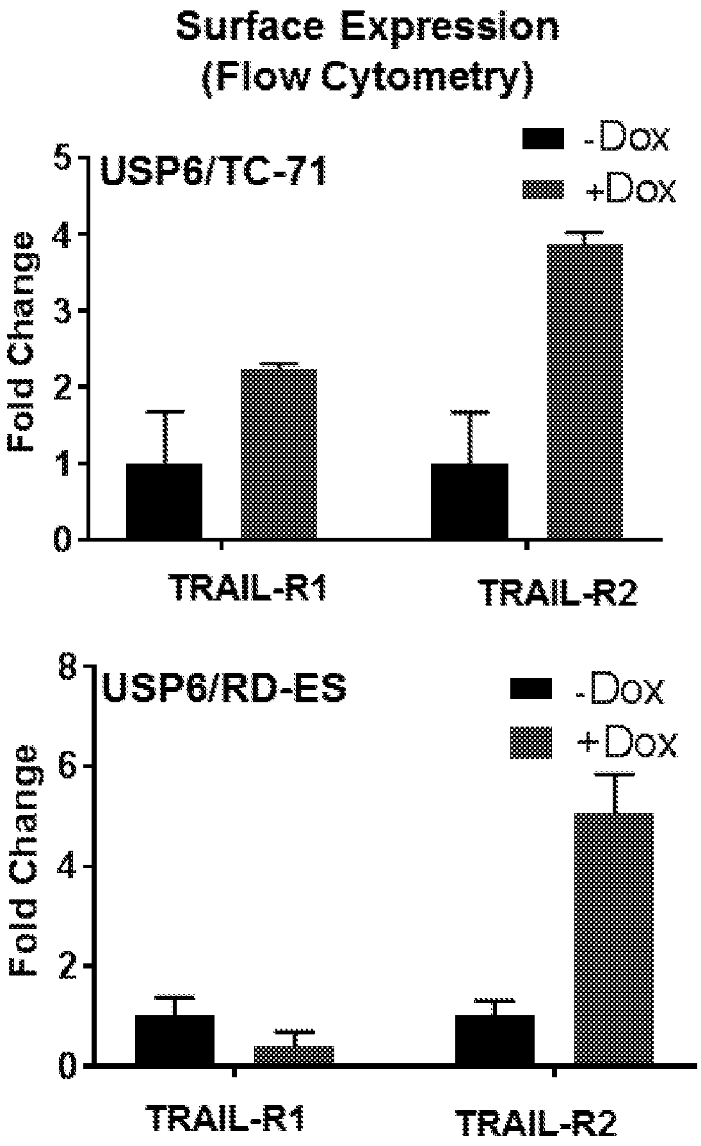
FIG. 9 shows the expression of TRAIL-R1 and TRAIL-R2 with (+Dox) or without (−Dox) USP6 expression in Ewing sarcoma cell lines TC-71 (top) and RD-ES (bottom). Surface expression was determined by flow cytometry.
Figure 10:
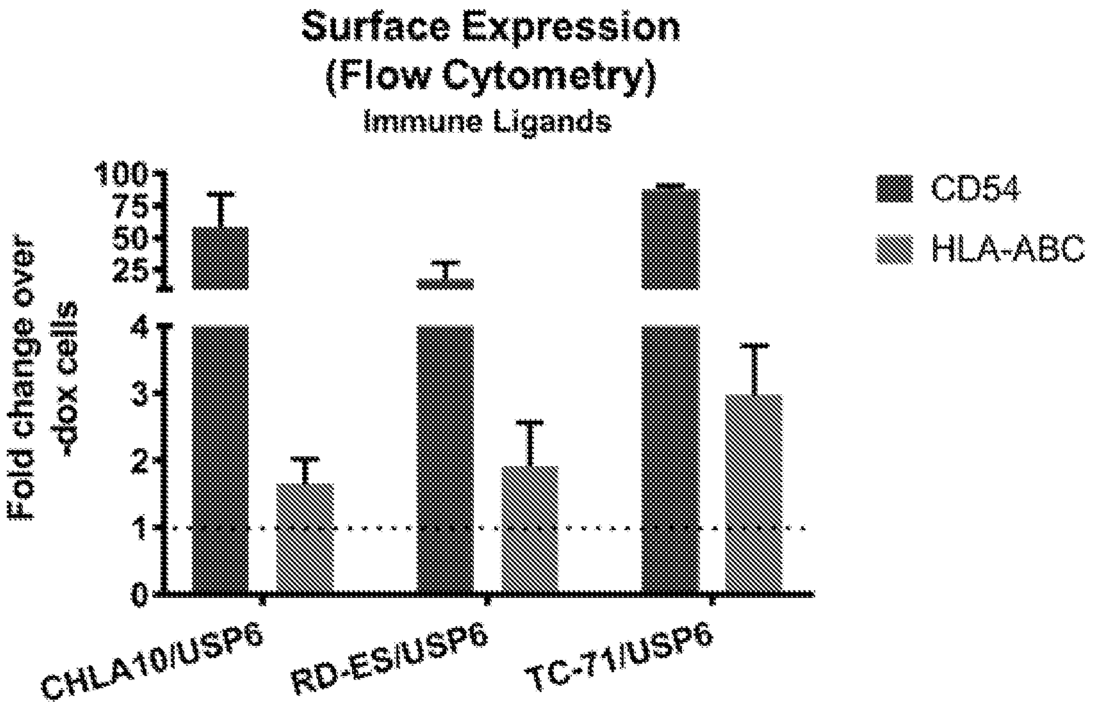
FIG. 10 shows the increase in expression of CD54 and HLA-ABC in Ewing sarcoma cell lines CHLA10, RD-ES, and TC-71. Surface expression was determined by flow cytometry.
Figure 11:
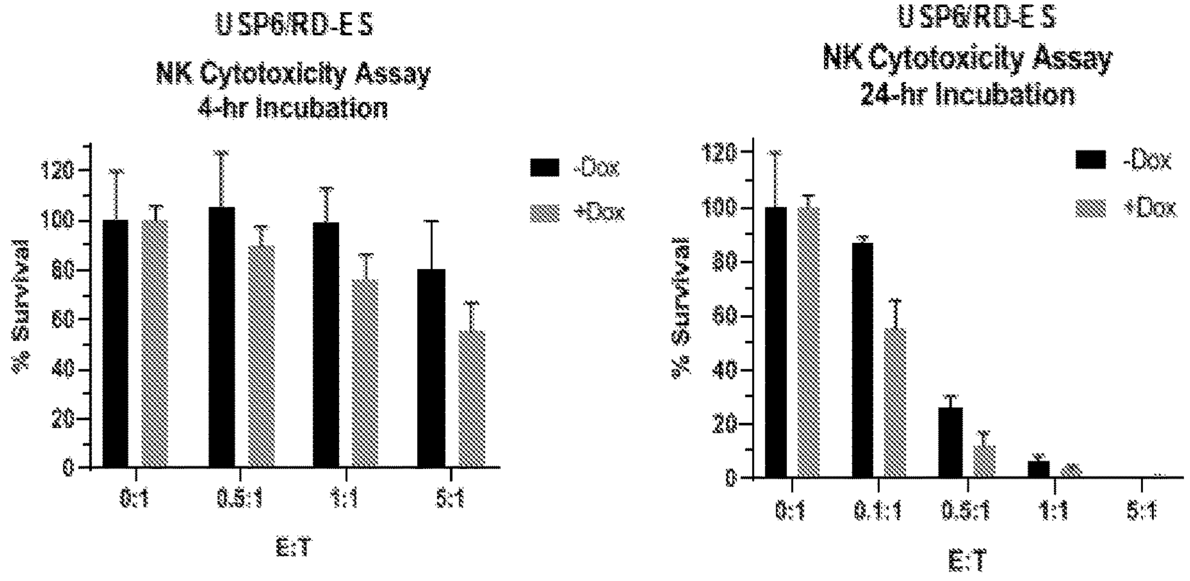
FIG. 11 provides graphs of a Natural killer (NK) cytotoxic assay with Ewing sarcoma cell line RD-ES with (+Dox) or without (−Dox) USP6. E:T represents Effector (NK cells): Target (tumor cell) ratio.

Ewing sarcoma cell lines TC-71, RD-ES, and CHLA10 were used in additional experiments. Notably, the addition of doxycycline (dox) results in USP6 expression. As seen in FIG. 9, USP6 upregulates the expression of TRAIL-R1 and TRAIL-R2, which hare the receptors for TRAIL, a pro-apoptotic ligand and useful for controlling tumor growth. As seen in FIG. 10, USP6 also upregulates the expression of CD54 (which allows cytotoxic immune cells to bind to target tumor cells) and HLA-ABC/MHC Class I (used by cytotoxic T cells to recognize and kill tumor cells). Natural killer (NK) cells are cytotoxic immune cells that can kill tumor cells. Notably, the induction of USP6 sensitizes tumor cells to the NK cell line NK-92 (FIG. 11).

EXAMPLE 4

Figure 12:
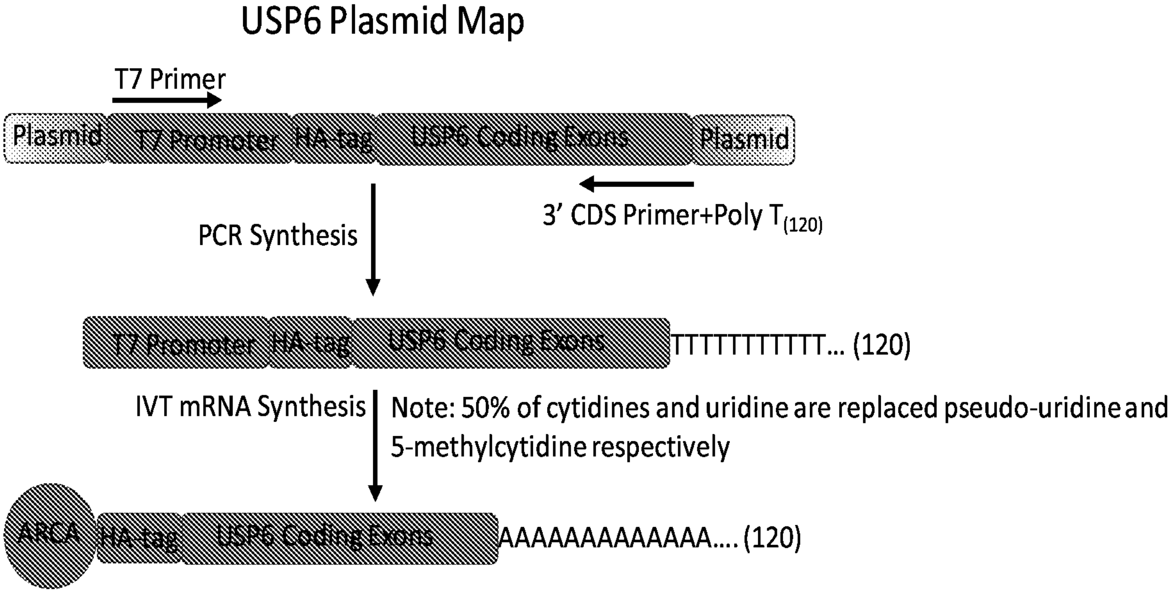
FIG. 12 provides a schematic of a USP6 plasmid map for expression of USP6. Presented thymidine sequence is SEQ ID NO: 6 and presented polyA tail is SEQ ID NO: 7.

FIG. 12 provides a schematic of a USP6 plasmid map for in vitro transcribed (IVT) mRNA. Commercially available kits such as the HiScribe™ T7 ARCA (Anti-Reverse Cap Analog) mRNA Kit (New England BioLabs; Ipswich, MA) can be used to generate capped and tailed mRNA. In vitro transcribed RNA can be administered to cells (e.g., via nanoparticles, liposomes, or micelles). Here, the commercial lipid carrier Lipofectamine® MessengerMax™ (Invitrogen, Carlsbad, CA) was used to encapsulate the mRNA and deliver it to the cell. Encapsulation and transfection was performed using the manufacturer's recommendations.

USP6 comprises a TBC (Tre-2/Bub2/Cdc16) domain and a ubiquitin-specific protease domain (USP). The A6 mutant of USP6 is a triple point mutant in the TBC domain that ablates USP6's ability to activate Arf6 and surface receptor trafficking (Lau et al. (2010) J. Biol. Chem., 285(47): 37111-37120). The CS mutant of USP6 comprises a point mutation in a key catalytic residue (Cys541→Ser) and ablates protein rescue activity (Madan et al. (2016) PNAS 113(21):E2945-E2954).

Figure 13:
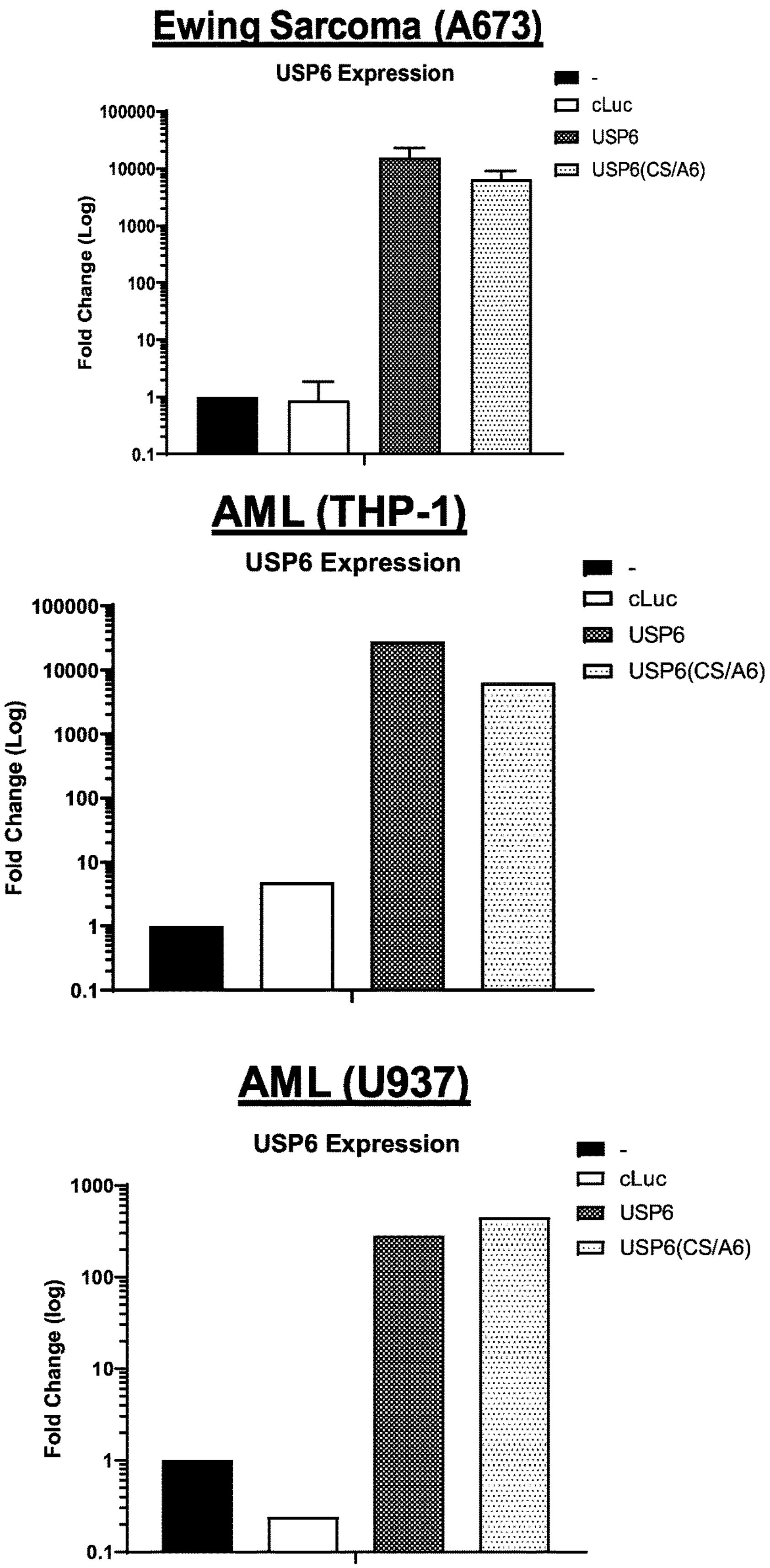
FIG. 13 provides graphs of the fold change of USP6 mRNA in Ewing Sarcoma cells (A673) and acute myeloid leukemia (AML) cells (THP-1 and U937). Cells were untreated (−), treated with a control (cLuc), or treated with USP6 or USP6(CS/A6) mRNA.

As seen in FIG. 13, quantitative PCR (qPCR) showed the successful expression of USP6 mRNA in Ewing Sarcoma and AML. USP6 expression was greater in cells with USP6 or USP6(CS/A6) compared to untreated cells or cells treated with a control (cLuc (*Cypridina* luciferase)).

Figure 14:
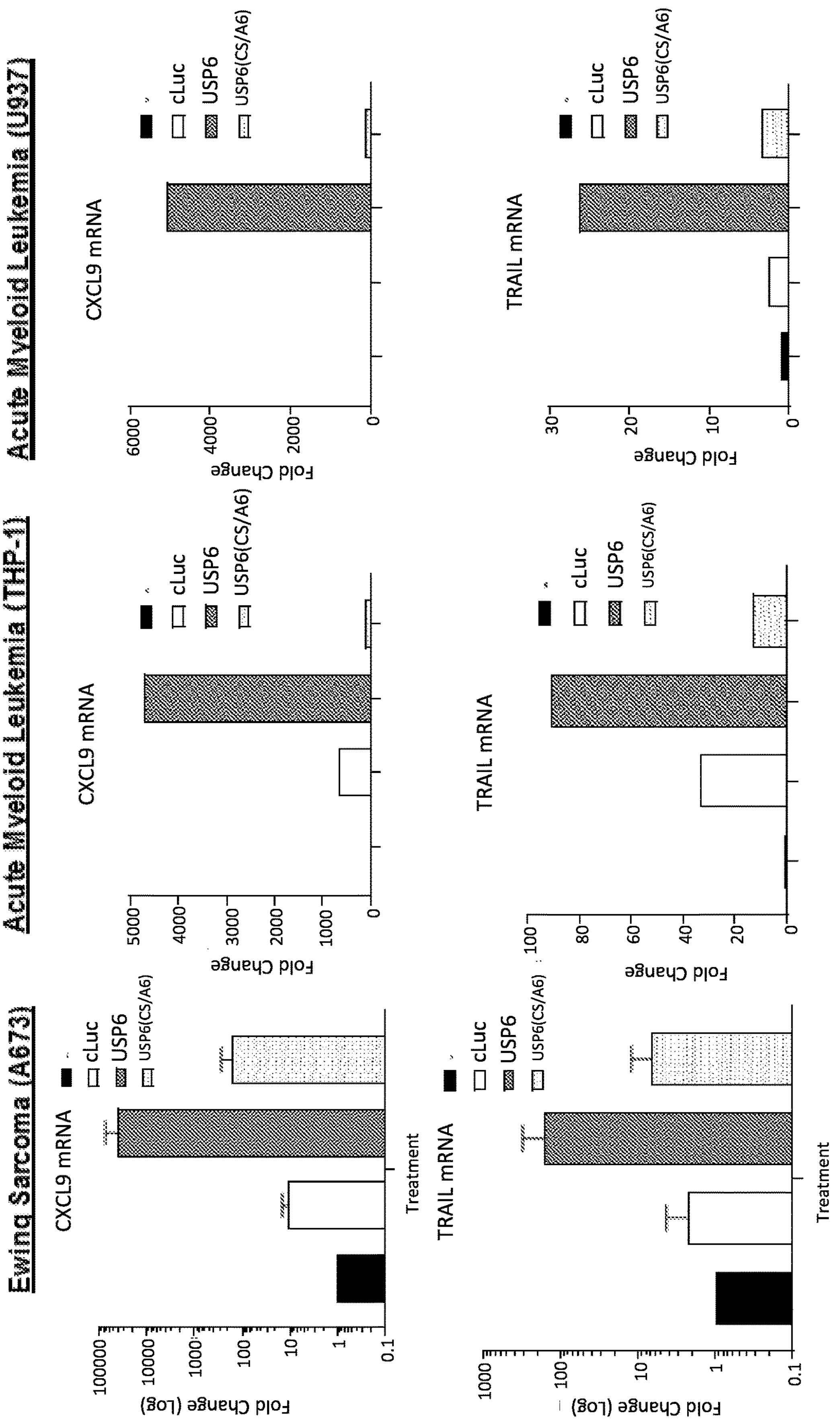
FIG. 14 provides graphs of the fold change of CXCL9 mRNA (top row) or TRAIL mRNA (bottom row) in Ewing Sarcoma cells (A673) and acute myeloid leukemia (AML) cells (THP-1 and U937). Cells were untreated (−), treated with a control (cLuc), or treated with USP6 or USP6(CS/A6) mRNA.

As seen in FIG. 14, USP6 mRNA induces anti-tumor cytokines in AML and Ewing Sarcoma. Indeed, CXCL9 and TRAIL mRNA expression was significantly increased in cells treated with USP6 compared to untreated cells, cells treated with a control (cLuc), or cells treated with the inactive mutant USP6(CS/A6).

Figure 15:
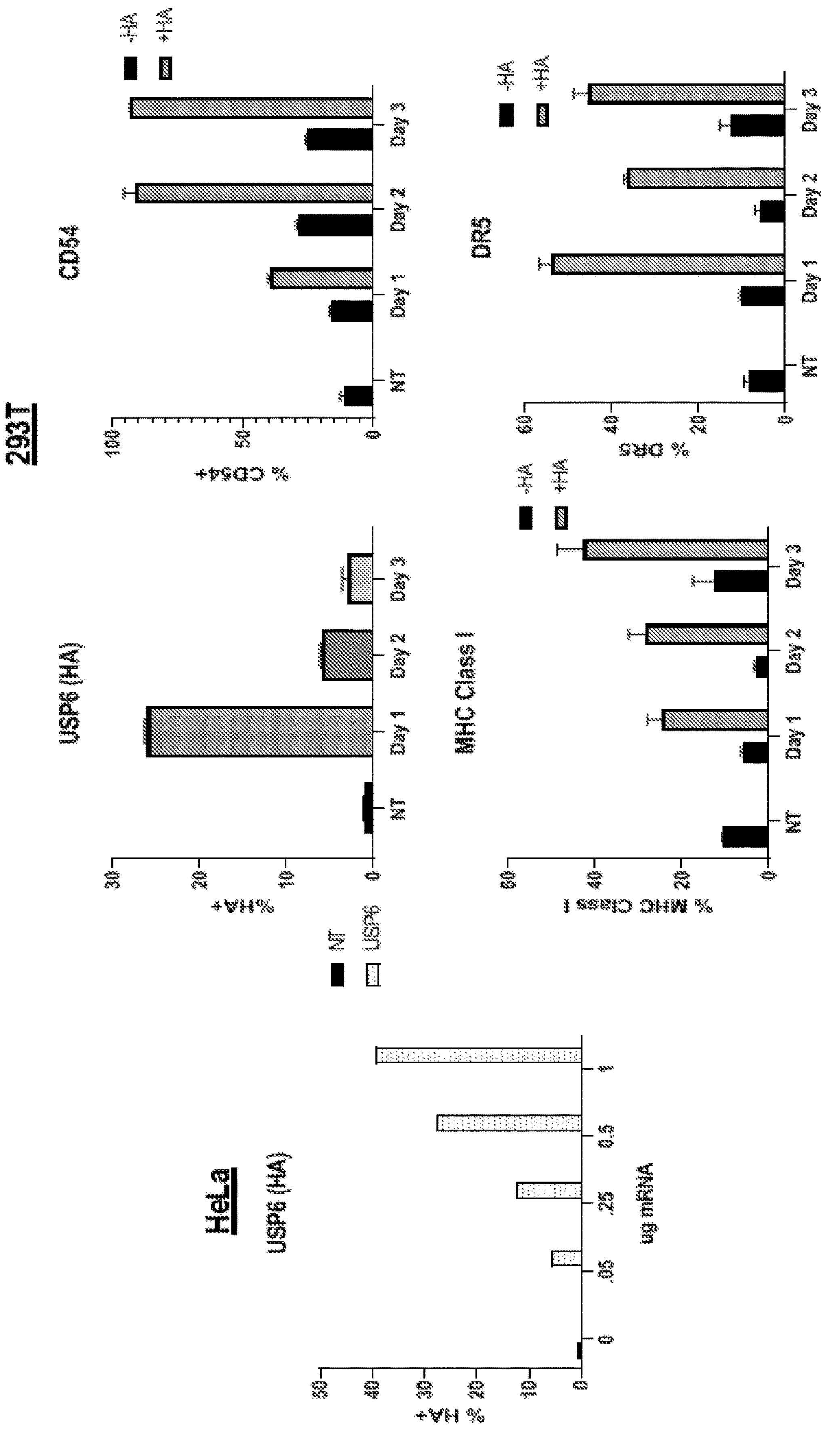
FIG. 15 provides a graph of the amount of HA-tagged USP6 protein in HeLa cells transduced with increasing amounts of USP6 mRNA.
Figure 16A:
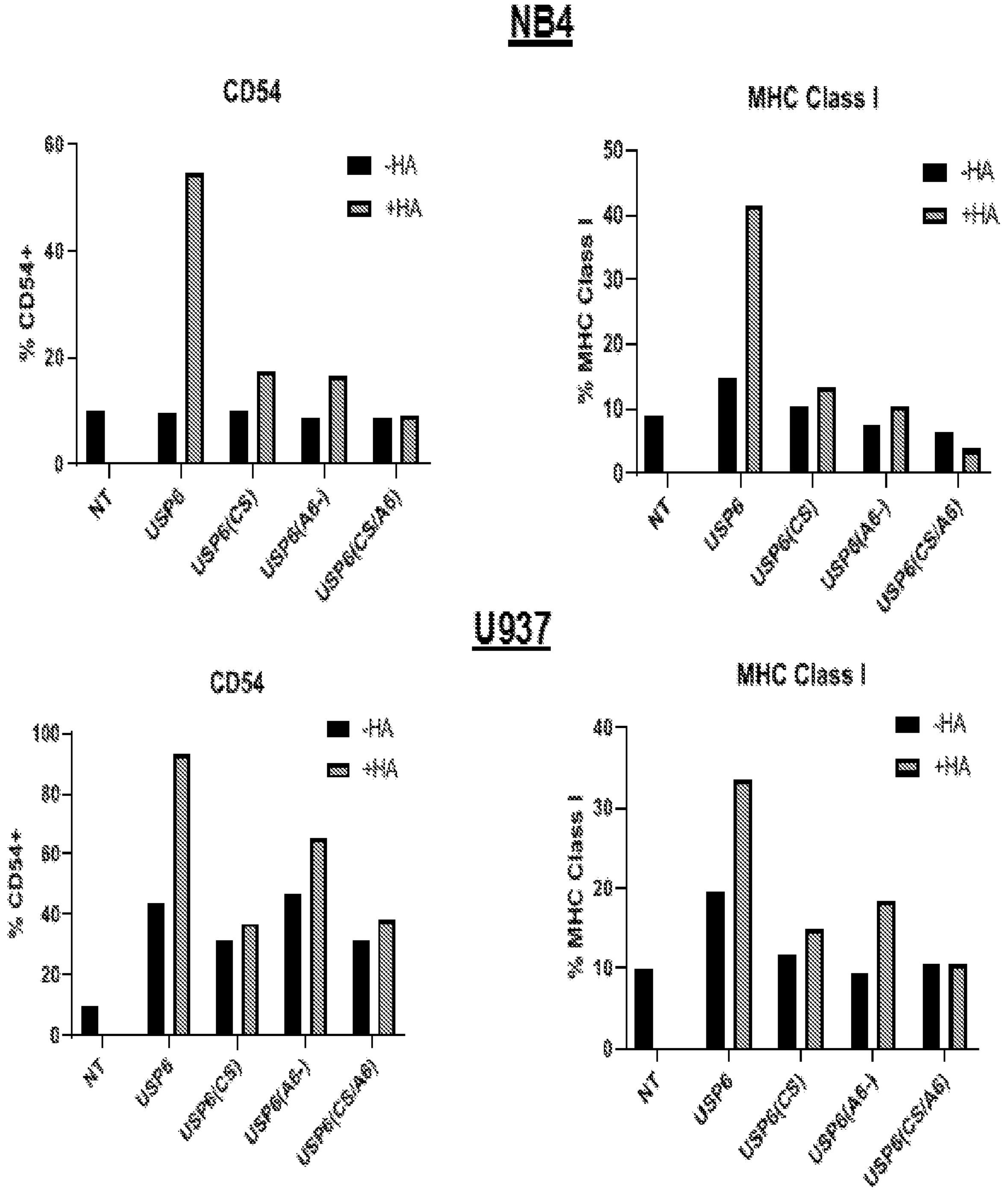
FIG. 16A provides graphs of the expression of CD54 and MHC Class I in NB4 or U937 AML cells after USP6 mRNA introduction. The presence of USP6 mRNA led to the increased surface expression of CD54 and MHC Class I compared to untreated cells or cells treated with the mutants USP6(CS) and USP6(A6) or the double mutant USP6(CS/A6).

As seen in FIG. 15, USP6 mRNA is translated into functional protein. HA-tagged USP6 protein was measured in HeLa cells transduced with increasing amounts of USP6 mRNA (FIG. 15). Experiments in 293T cells shows that the increase of HA-tagged USP6 protein is transient and that the introduction of USP6 mRNA led to the increased surface expression of CD54, MHC Class I, and DR5. USP6 mRNA also increases surface expression of immune recognition markers in several AML cell lines (NB4, U937) (FIG. 16A). Indeed, the presence of USP6 mRNA led to the increased expression of CD54 and MHC Class I compared to untreated cells or cells treated with the mutants USP6(CS) and USP6 (A6) or the double mutant USP6(CS/A6). FIG. 16B shows the increased expression of DR5 and MHC Class I in THP-1 or U937 AML cells after USP6 mRNA introduction, compared to controls.

Figure 17:
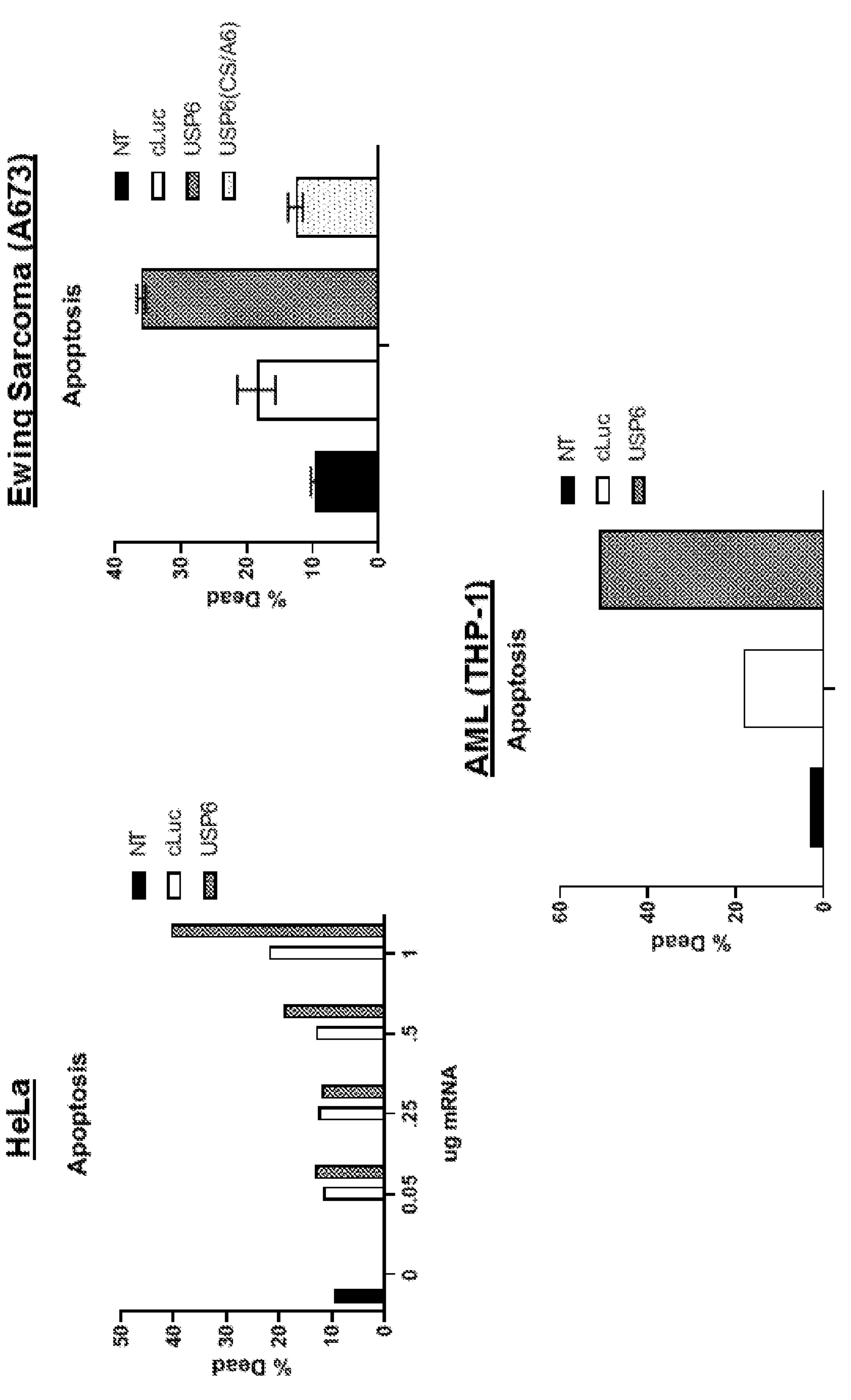
FIG. 17 provides graphs of the percentage of dead cells in HeLa, Ewing Sarcoma cells (A673) and acute myeloid leukemia (AML) cells (THP-1) that were untreated (NT), treated with a control (cLuc), or treated with USP6 or USP6(CS/A6).

As seen in FIG. 17, USP6 mRNA selectively induces death in several cell lines. Apoptosis was induced in HeLa, Ewing Sarcoma (A673), and AML (THP-1) cells when the cells were treated with USP6 mRNA but not in untreated cells or cells treated with either the control cLuc or the inactive double mutant USP6(CS/A6).

Figure 18:
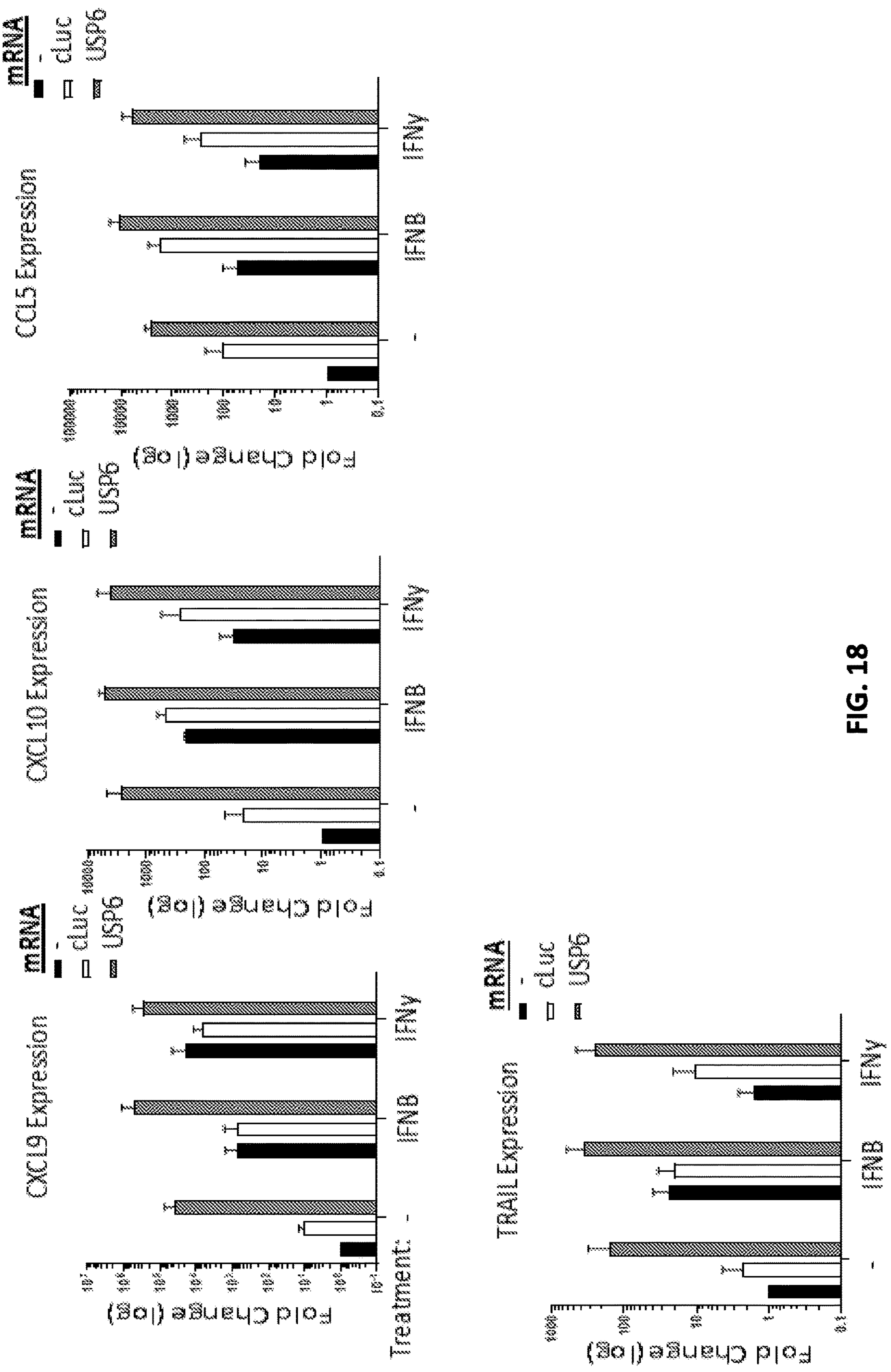
FIG. 18 provides graphs of the fold change of CXCL9, CXCL10, CCL5, and TRAIL mRNA in Ewing Sarcoma cells (A673). Cells were untreated (−), treated with a control (cLuc), or treated with USP6 mRNA.

The Ewing sarcoma cell line A673 was also transfected with Lipofectamine® MessengerMax™ with 1 μg of the control mRNA (cLuc) or USP6 mRNA. The cells were then treated with 1000 U/mL IFNβ or 0.5 ng/mL IFNγ. USP6 mRNA selectively induces potent expression of anti-tumor cytokines CXCL9, CXCL10, CCL5, and TRAIL compared to controls (FIG. 18).

Figure 19:
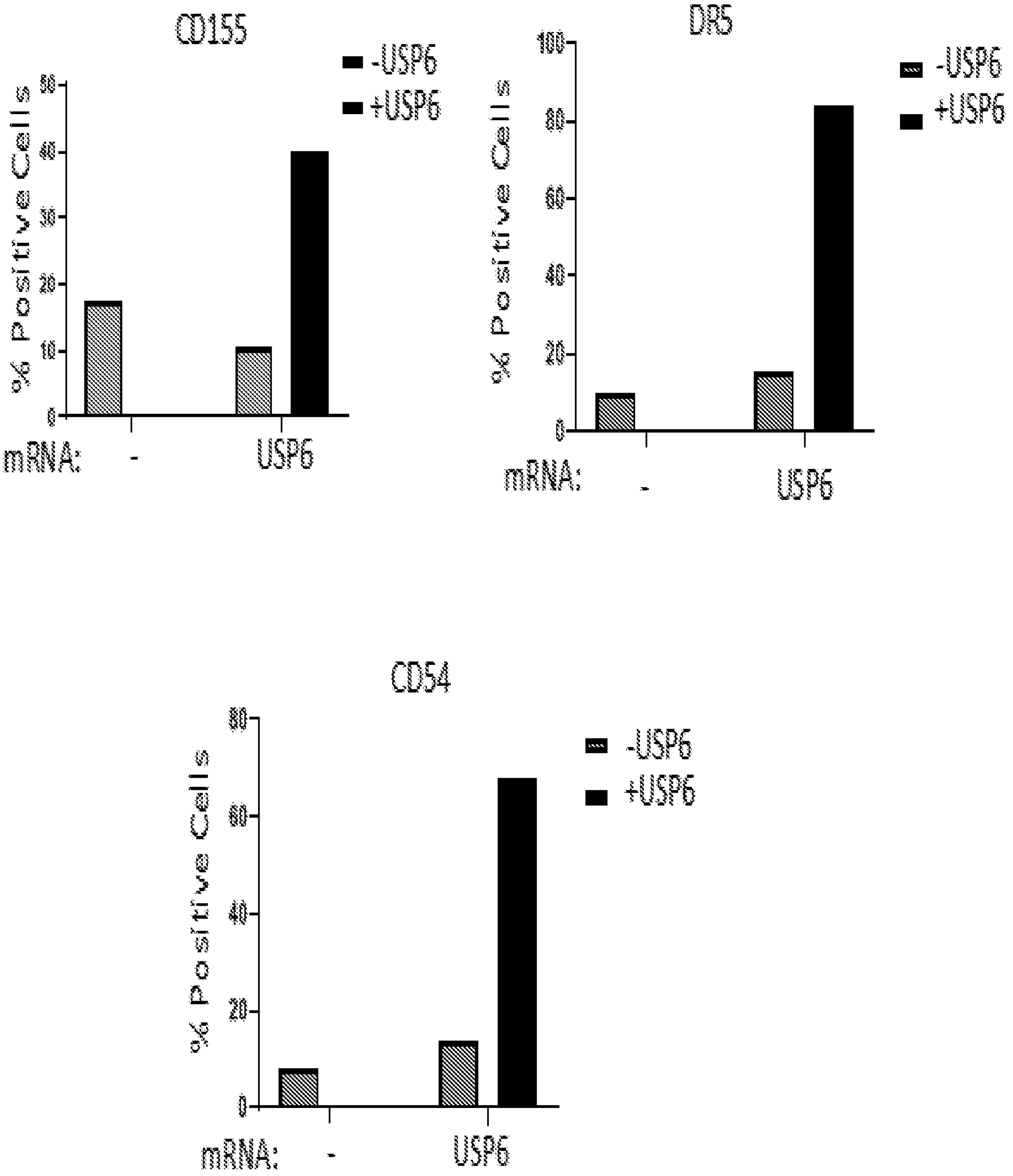
FIG. 19 provides a graph of the percentage of cells positive for surface CD54, DR5, and CD155. The Ewing sarcoma cells (A673) were either untreated or transfected with USP6 mRNA and then sorted into $USP6^-$ or $USP6^+$ populations prior to surface expression determination of the anti-tumor surface receptors.

The Ewing sarcoma cell line A673, either untreated or transfected with USP6 mRNA, were sorted into $USP6^-$ or $USP6^+$ populations. The surface expression of anti-tumor surface receptors was then analyzed. As seen in FIG. 19, USP6-expressing cells express high levels of the anti-tumor receptors CD54, DR5, and CD155.

EXAMPLE 5

The requirements of the USP6 3' UTR for protein expression were investigated with three different constructs. In order to synthesize IVT mRNA, the first step is to create a workable fragment using primers against the 3' and 5' end. Here, a T7 promoter was used which serves as the binding site for T7 RNA polymerase to synthesize IVT mRNA. The constructs also comprise an HA tag at the 5' end of the USP6 coding region to help detect USP6 protein expression. At the 3' end, the first construct ends at the 3' end of the USP6 coding region (termed CDS). The second construct further comprises the USP6 3'UTR. The third construct further comprises the USP6 3'UTR (termed UTR) and the SP6 site located just downstream of the USP6 3' UTR.

IVT mRNA was synthesized with a kit from NEB (www.neb.com/products/e2060-hiscribe-t7-arca-mma-kit-with-tailing#Product%20Information). The mRNA was capped with ARCA (Anti-Reverse Cap Analog) to improve expression. 50% of the uridines and cytosines were replaced with synthetic 5-methylcytosine and pseudouridine to also improve expression and reduce cell death. Notably, the USP6 used in these experiments contained a point mutation (Y162H), which does not appear to affect USP6's function or expression. An enzymatic process was employed for the addition of a poly A tail for proper mRNA translation and stability. The enzymatic method creates a pool of products with a variable length tail (typically 100-200 bases).

Figure 20A:
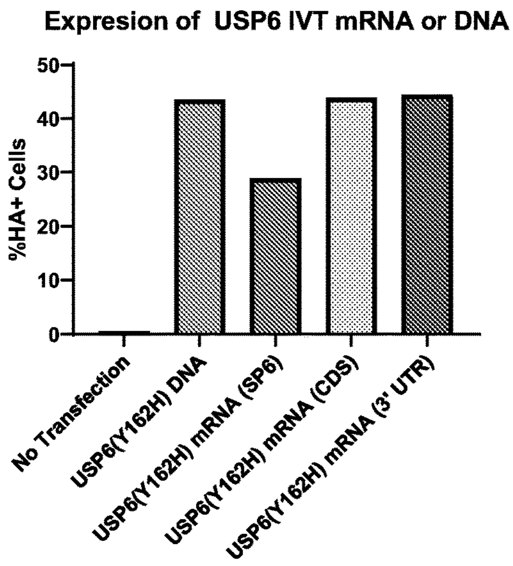
FIG. 20A provides a graph of the expression of various USP6(Y162H) IVT mRNA constructs or a DNA control after transfection into 293T.

USP6(Y162H) IVT mRNA or a DNA control was transfected into 293T using a commercially available lipid carrier (Lipofectamine® MessengerMax™ for mRNA and Lipofectamine® 2000 for DNA). 1.6 μg of DNA or mRNA were used per sample. The percentage of cells that expressed USP6 was determined by intracellular flow cytometry using an anti-HA antibody. As seen in FIG. 20A, all of the constructs expressed USP6. However, the CDS and UTR versions were better than the SP6 version. The CDS construct was selected for further experimentation as the 3' UTR of USP6 appears to be targeted by multiple miRNAs which can negatively regulate its expression.

As stated above, the poly A tail was initially added using an enzymatic method. This technique gives a pool of products with variable length tails. In order to provide a more defined product, the poly A tail was added directly via a reverse CDS primer that contained 120 thymines. The resulting IVT mRNA, therefore, contains a defined poly A tail of 120 adenosines.

USP6(Y162H) IVT mRNA whose poly A tail was added via the enzymatic or PCR method or a DNA control were transfected into 293T using a commercially available lipid carrier (Lipofectamine® MessengerMax™ for mRNA and Lipofectamine® 2000 for DNA) at various amounts. The percentage of cells that expression USP6 was determined by intracellular flow cytometry using an anti-HA antibody. USP6 can increase surface expression of CD155 and CD54, which are two important receptors for immune cell recognition of tumors. Accordingly, it was also determined if the USP6(Y162H) IVT mRNA was functional by looking at surface expression of CD155 and CD54 via flow cytometry.

Figure 20B:
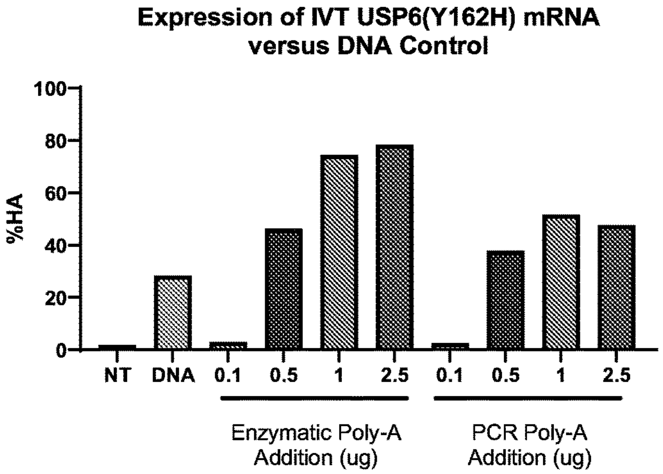
FIG. 20B provides a graph of the expression of USP6(Y162H) IVT mRNA constructs with either an enzymatically added polyA tail or a defined polyA tail or a DNA control after transfection into 293T.
Figure 20C:
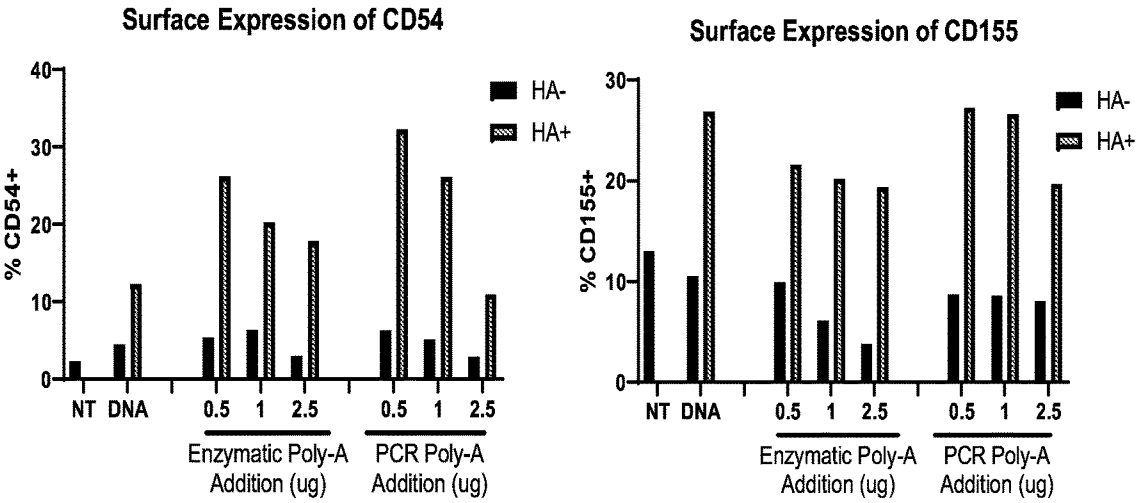
FIG. 20C provides graphs of the surface expression of CD54 and CD155 in 293T cells after transfection with USP6(Y162H) IVT mRNA constructs with either an enzymatically added polyA tail or a defined polyA tail or a DNA control.

As seen in FIG. 20B, enzymatic poly(A) tailing slightly increases the expression of USP6 mRNA. However, the addition of a defined 120-base poly(A) tail does not negatively affect expression of USP6 or key anti-tumor surface markers (CD155 and CD54) by USP6 (FIG. 20C). Therefore, the USP6 mRNA product containing a defined 120-base poly(A) tail was selected for further study.

The expression of wild-type USP6 against USP6(Y162H) was tested in several cell lines including 293T (embryonic kidney), A673 (Ewing sarcoma), and K562 (chronic myeloid leukemia). USP6(Y162H) or USP6 IVT mRNA with a defined 120-base poly(A) tail or a DNA control were transfected into 293T using a commercially available lipid carrier (Lipofectamine® MessengerMax™ for mRNA and Lipofectamine® 2000 for DNA). mRNA was used at 0.5 μg and DNA at 1.6 μg. The percentage of cells that expression USP6 was determined by intracellular flow cytometry using an anti-HA antibody.

Figure 21A:
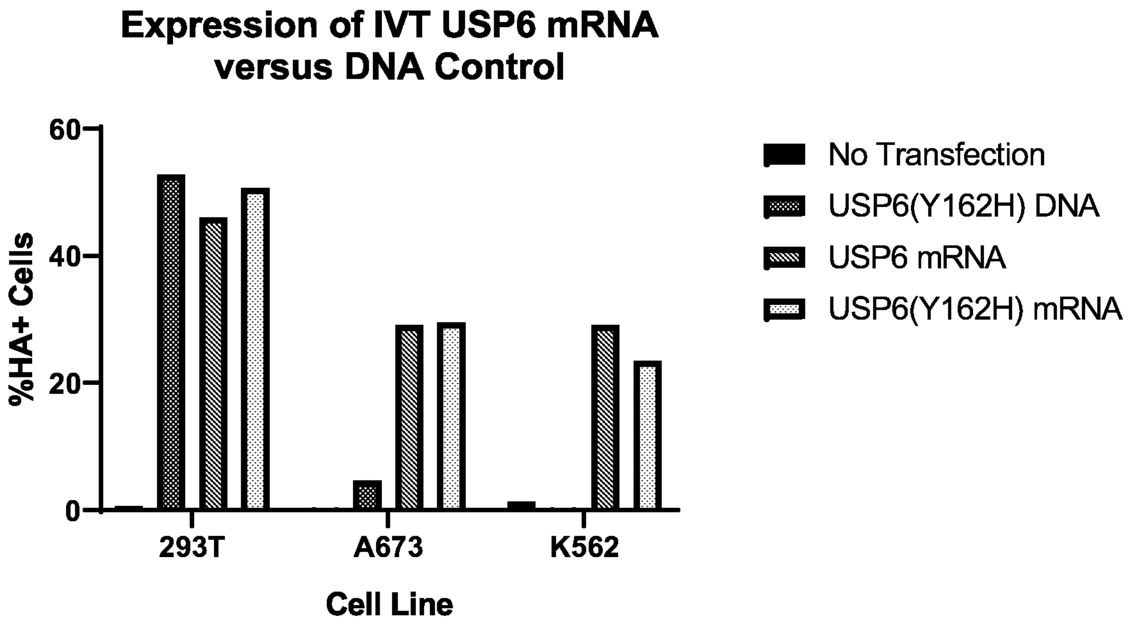
FIG. 21A provides a graph of the expression of USP6 in various cell lines. Cells were either not transfected or transfected with USP6(Y162H) IVT mRNA, USP6 IVT mRNA, or USP6(Y162H) DNA.

As seen in FIG. 21A, all cell lines express high levels of IVT USP6 or USP6(Y162H), even exceeding the expression of the DNA control in the A673 and K562 lines. WT USP6 mRNA expression was identical to USP6(Y162H) mRNA.

Figure 21B:
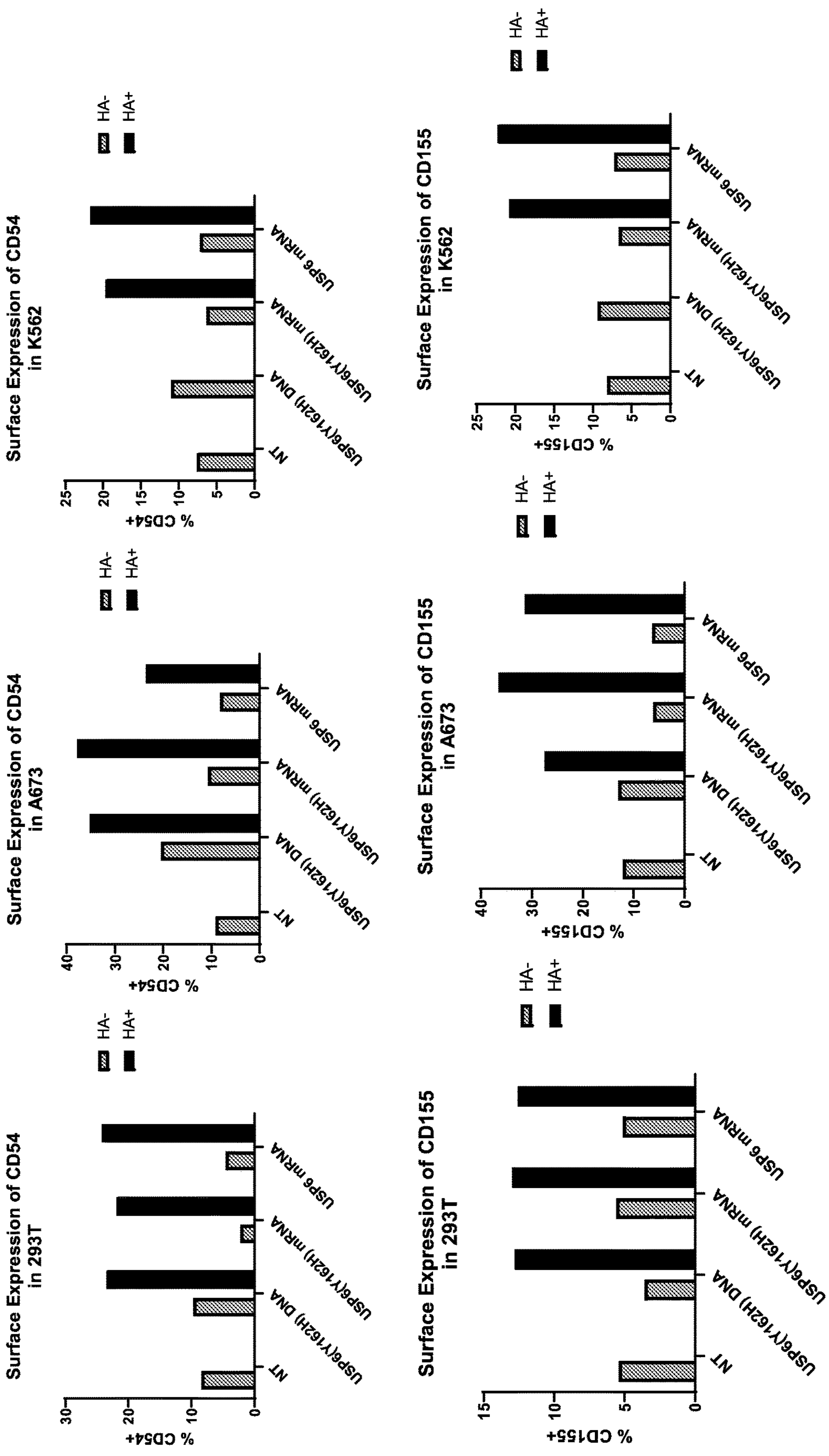
FIG. 21B provides graphs of the expression of CD54 and CD155 in 293T in various cell lines after transfection with USP6(Y162H) IVT mRNA, USP6 IVT mRNA, or USP6(Y162H) DNA. NT: not transfected.

The functionality of USP6 IVT mRNA was confirmed in the above cell lines by looking at surface upregulation of CD54 and CD155. The HA+ population for the DNA sample was non-existent in the K562 system and was excluded from analysis. As seen in FIG. 21B, WT USP6 mRNA results in upregulation of key anti-tumor surface markers and performs identically to USP6(Y162H) mRNA.

Figure 22:
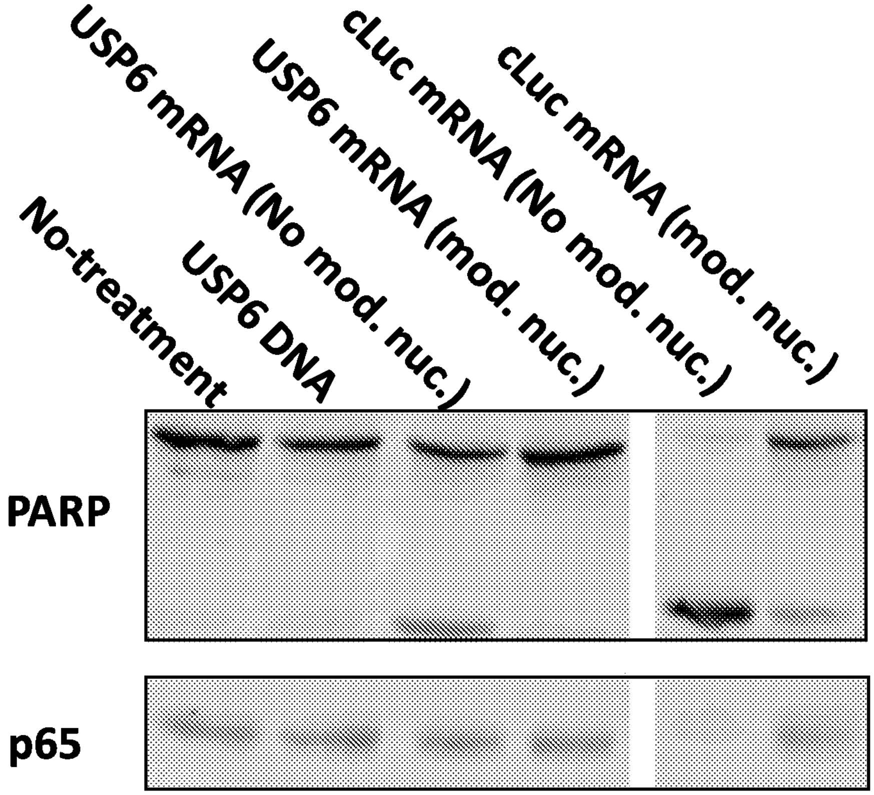
FIG. 22 provides an image of a Western blot of PARP expression in untreated cells or cells transfected with USP6 DNA, USP6 mRNA (unmodified), USP6 mRNA (modified nucleotides), cLuc mRNA (unmodified), or cLuc mRNA (modified nucleotides).

Exogenous IVT mRNA can mimic a virus and cause the target cell die. This non-specific cell death can be avoided by the incorporation of modified nucleotides that prevent the cell from recognizing the IVT mRNA as foreign. The replacement (e.g., of 50%) of the uridines and cytosines with pseudouridine and 5-methylcytosine, respectively, can prevent non-specific cell death. To test this, USP6 or *Cypridina* luciferase (cLuc) mRNA with or without any modified nucleotides were tested in cells. cLuc mRNA served as a control mRNA. Cell death was monitored by PARP cleavage. When cells die, the PARP protein is cleaved and lower molecular weight band appears. Protein p65 served as a loading control. As seen in FIG. 22, modified nucleotides prevent non-specific cell death. USP6 mRNA or control cLuc mRNA that did not contain modified nucleotides lead to significant, non-specific cell death.

Figure 23:
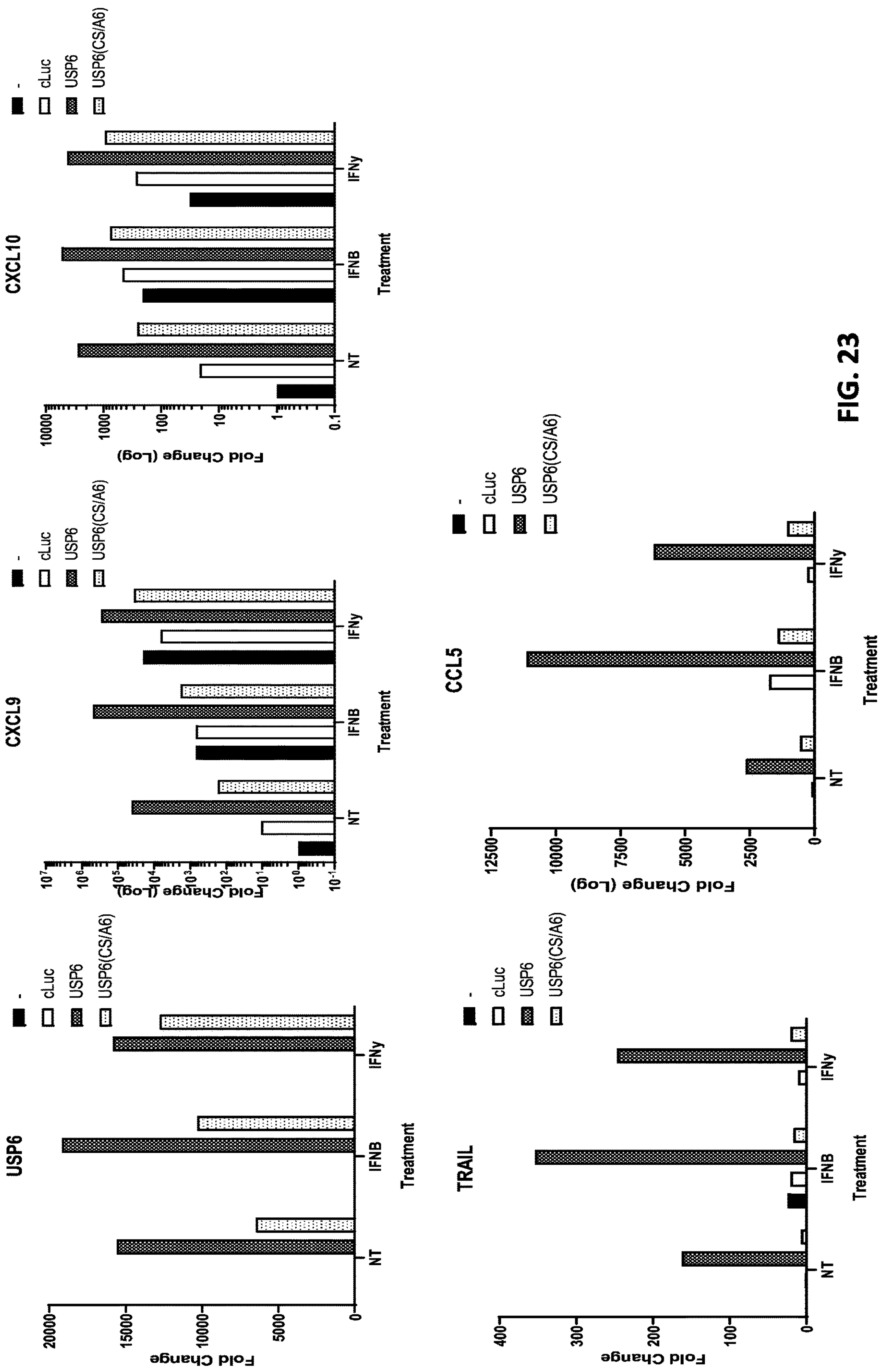
FIG. 23 provides graphs of the expression of USP6, CXCL9, CXCL10, TRAIL, or CCL5 in A673 after transfection with cLuc, USP6 mRNA, or USP6(CS/A6) mRNA.

USP6 can dramatically enhance tumor cell's response to interferons (IFNs), a potent anti-tumor cytokine. USP6 can induce the production of the anti-tumor cytokines CXCL9, CXCL10, CCL5, and TRAIL and IFN treatment leads to the synergistic increase in expression of these chemokines. A mutant USP6 mRNA (termed USP6(CS/A6−)) was also generated. USP6(CS/A6−) is identical to WT USP6 mRNA except it has inactivating mutations in both the TBC and USP domains, thereby rendering it functionally inert. Here, A673 cells were transfected with USP6 mRNA (ARCA cap, modified nucleotides, no 3'UTR, defined polyA) or cLuc/USP6(CS/A6−) as controls. Following transfection, these cells were treated with either 1000 U/mL IFNβ or 0.5 ng/mL IFNγ for 24 hours. USP6 and anti-tumor cytokine expression were measured by RT-qPCR. As seen in FIG. 23, USP6 mRNA and mutant USP6 mRNA express in target cells. However, only USP6 mRNA induces potent cytokine expression which is synergistically enhanced upon IFN treatment.

Figure 24:
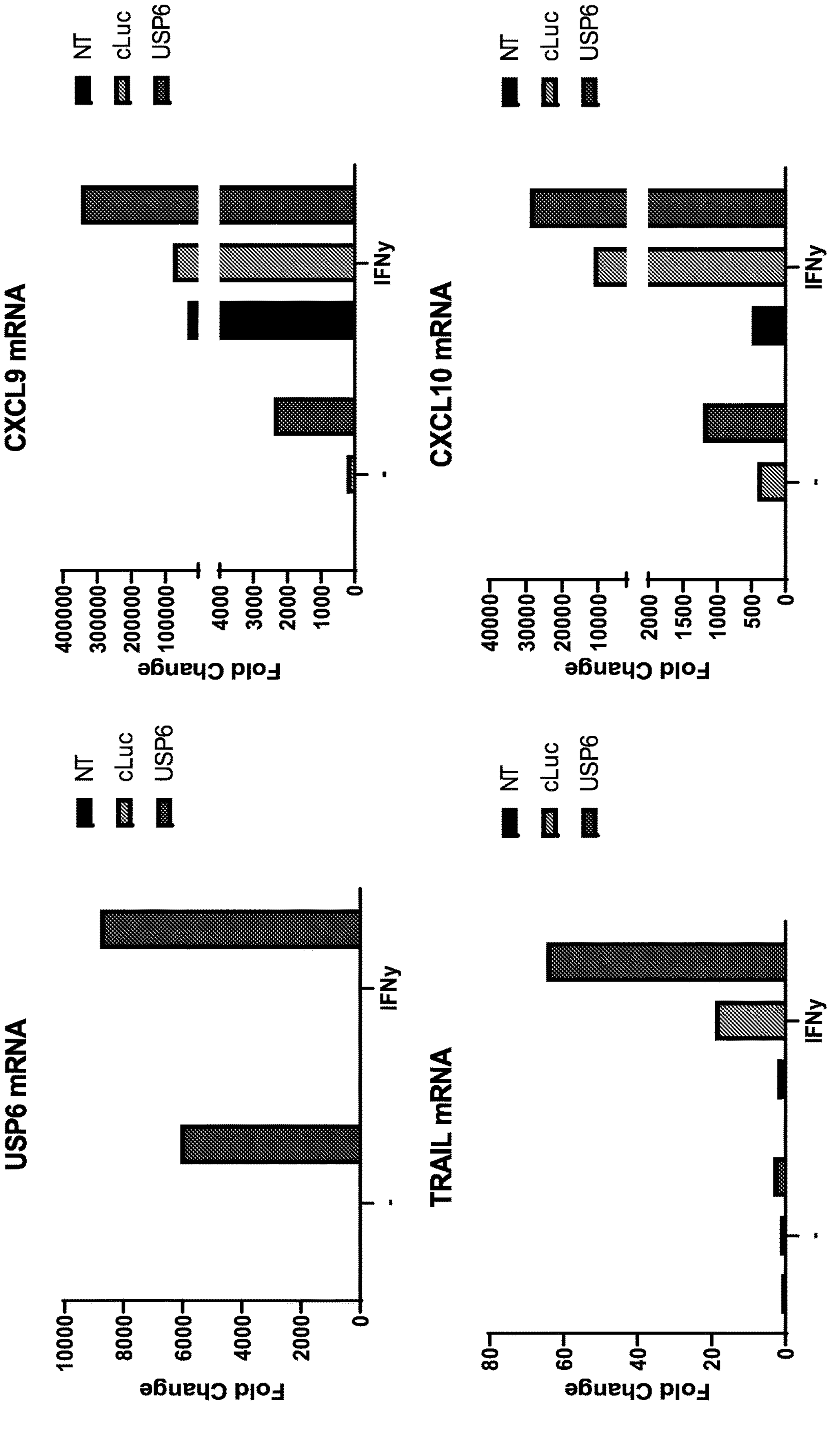
FIG. 24 provides graphs of the expression of USP6, CXCL9, TRAIL, and CXCL10 mRNA in TC-71 cells transfected with cLuc or USP6 mRNA with or without IFNγ treatment. NT: not transfected.

Since strong, synergistic anti-tumor cytokine production was observed in the Ewing sarcoma cell line A673, another Ewing sarcoma cell (TC-71) was also tested. Here, TC-71 cells were transfected with USP6 mRNA or cLuc as a control. Following transfection, these cells were treated with 5 ng/mL IFNγ for 24 hours. USP6 and anti-tumor cytokine expression was measured by RT-qPCR. As seen in FIG. 24, USP6 mRNA was expressed in TC-71 cells and induced potent ant-tumor cytokine expression by itself and synergized with IFNγ. These results recapitulate those seen in A673 cells.

Figure 25:
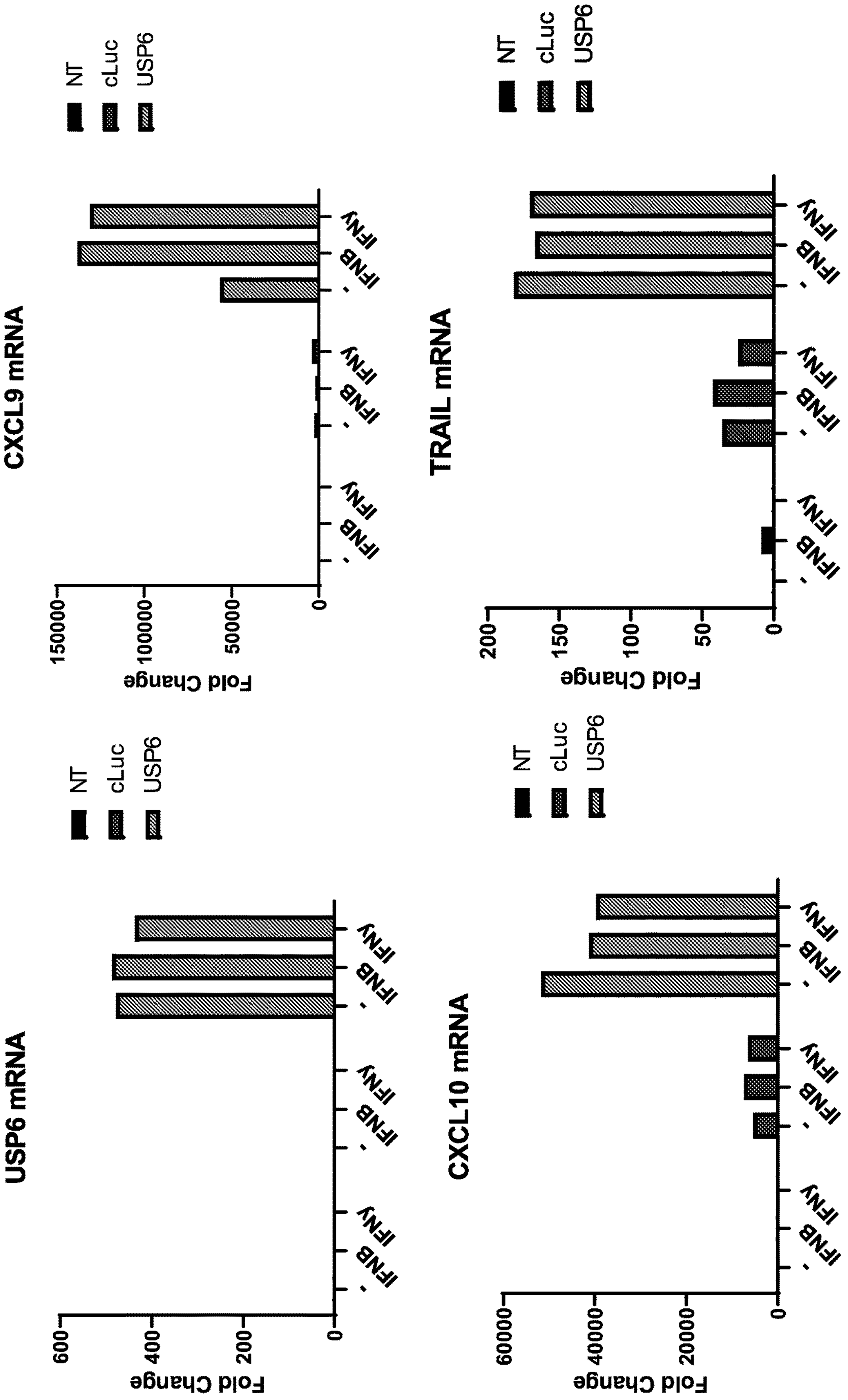
FIG. 25 provides graphs of the expression of USP6, CXCL9, TRAIL, and CXCL10 mRNA in the AML cell line THP-1 transfected with USP6 mRNA or cLuc as a control. Following transfection, these cells were treated with either 1000 U/mL IFNβ or 5 ng/mL IFNγ for 24 hours. NT: not transfected.

To confirm that the effects of the USP6 mRNA were not limited to just Ewing sarcoma, the AML cell line THP-1 was transfected with USP6 mRNA or cLuc as a control. Following transfection, these cells were treated with either 1000 U/mL IFNβ or 5 ng/mL IFNγ for 24 hours. USP6 and anti-tumor cytokine expression was measured by RT-qPCR. As seen in FIG. 25, USP6 mRNA was expressed in the AML cell line THP-1 and induced potent ant-tumor cytokine expression by itself and synergized with IFNβ/γ. These results recapitulate those seen in Ewing sarcoma cell lines.

Figure 26:
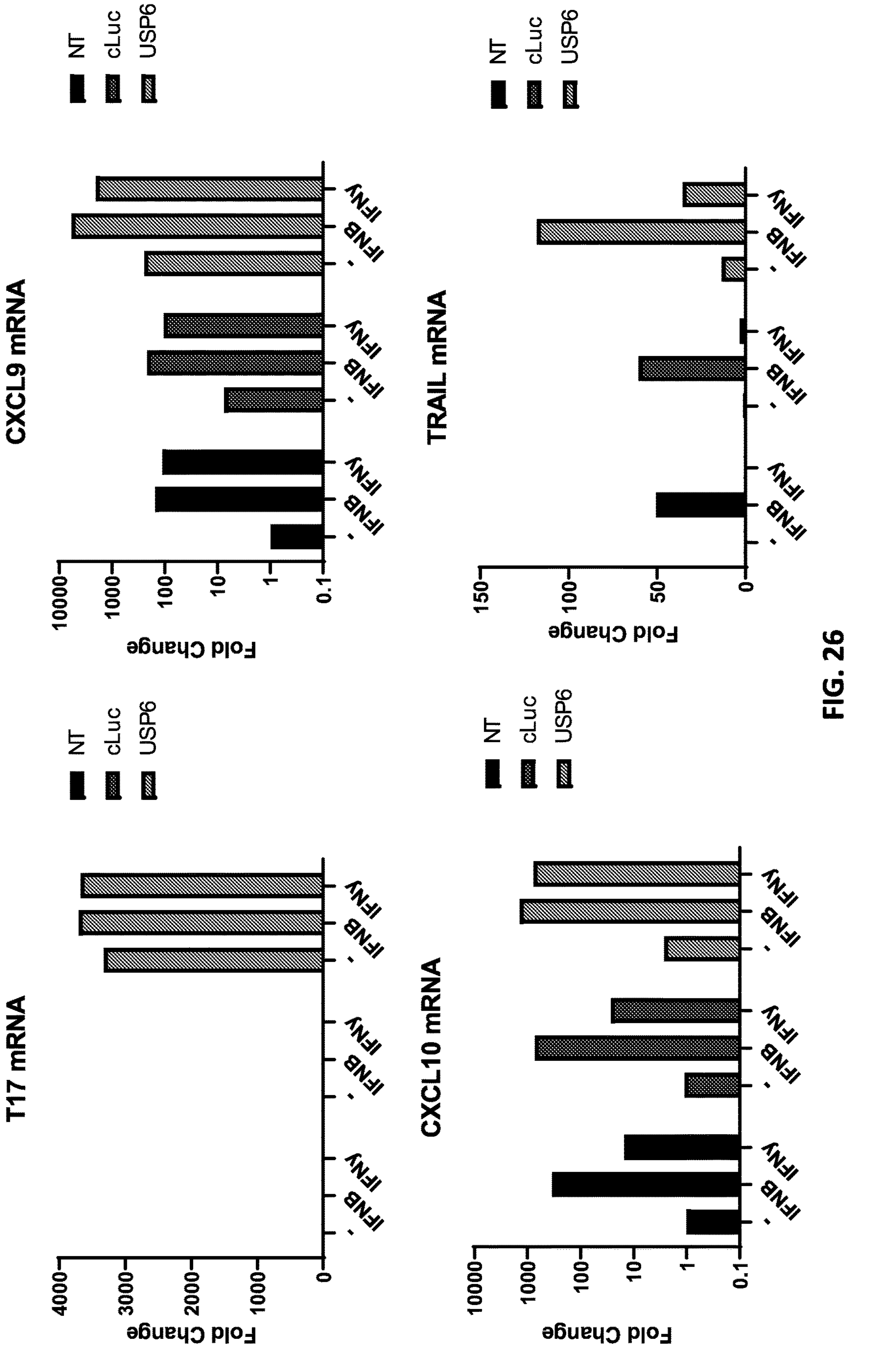
FIG. 26 provides graphs of the expression of T17, CXCL9, TRAIL, and CXCL10 mRNA in the AML cell line U937 transfected with USP6 mRNA or cLuc as a control. Following transfection, these cells were treated with either 1000 U/mL IFNβ or 5 ng/mL IFNγ for 24 hours. NT: not transfected.

Additionally, the AML cell line U937 was transfected with USP6 mRNA or cLuc as a control. Following transfection, these cells were treated with either 1000 U/mL IFNβ or 5 ng/mL IFNγ for 24 hours. USP6 and anti-tumor cytokine expression was measured by RT-qPCR. As seen in FIG. 26, USP6 mRNA was expressed in the AML cell line U937 and induced potent ant-tumor cytokine expression by itself and synergized with IFNβ/γ. These results recapitulate those seen in Ewing sarcoma cell lines.

Figure 27:
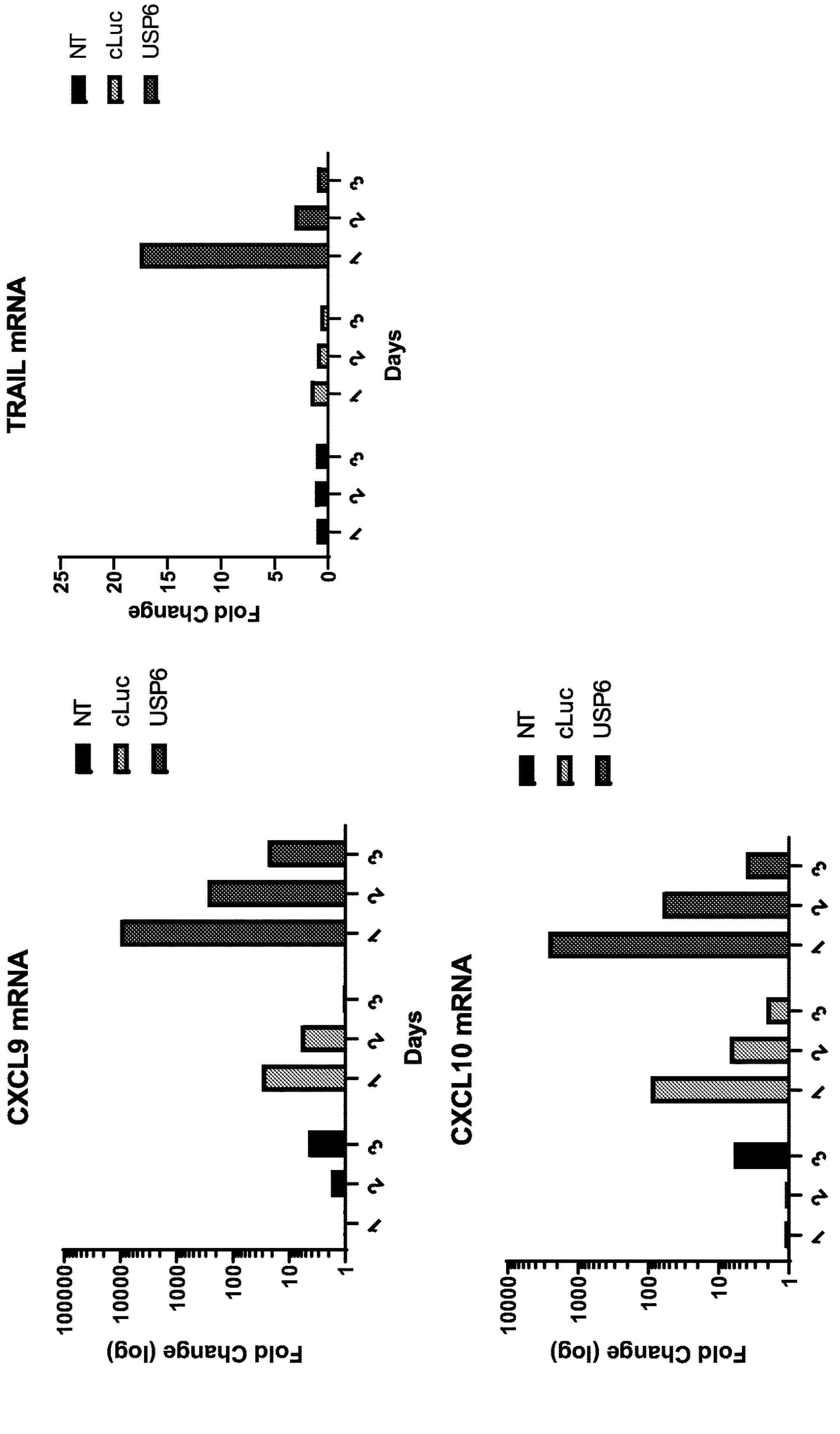
FIG. 27 provides graphs of the expression of CXCL9, TRAIL, and CXCL10 mRNA at days 1, 2, and 3 in the AML cell line THP-1 after transfection with USP6 mRNA or cLuc as a control.

Strong, long-term expression of an inflammatory agent would be detrimental to a patient. Accordingly, it is desirable to have the expression of USP6 to be transient. Here, the THP-1 cell line was transfected with USP6 mRNA or cLuc as a control. Following transfection, the cells were harvested 1, 2, or 3 days after transfection. As seen in FIG. 27, USP6 mRNA causes potent ant-tumor cytokine production after 1 day that rapidly declines by day 3.

As seen above, the expression of USP6 mRNA has been confirmed by qPCR. Here, the functional protein levels were examined. Since the mRNA encodes USP6 tagged with HA, an intracellular flow cytometry (IC flow) was used to observe the percent of cells that expressed USP6 over the course of several days. Furthermore, the cells could be divided into USP6+ and USP6− populations (HA+ and HA−) to observe the expression of the anti-tumor receptors known to be affected by USP6. As seen in FIG. 15, USP6 expression in 293T cells peaks at day 1, but rapidly declines back to baseline by day 3, which is similar to the previous qPCR timecourse in THP-1. Even though the percentage of cells expressing USP6 decreases, those cells that still express USP6 (i.e., HA+) still have high expression of anti-tumor surface receptors.

In further experiments, HeLa (cervical cancer) were transfected with nothing (NT), cLuc, and USP6 mRNA. USP6 protein expression was then detected by IC flow (staining with HA antibody) and upregulation of anti-tumor surface receptors DR5 and CD54 was detected. Samples were harvested at 6 and 24 hours after treatment. The expression of USP6 was detectable after 6 hours of mRNA treatment and rapidly increased by 24 hours. Upregulation of key anti-tumor surface markers was also observed as early as 6 hours after treatment.

Figure 28:
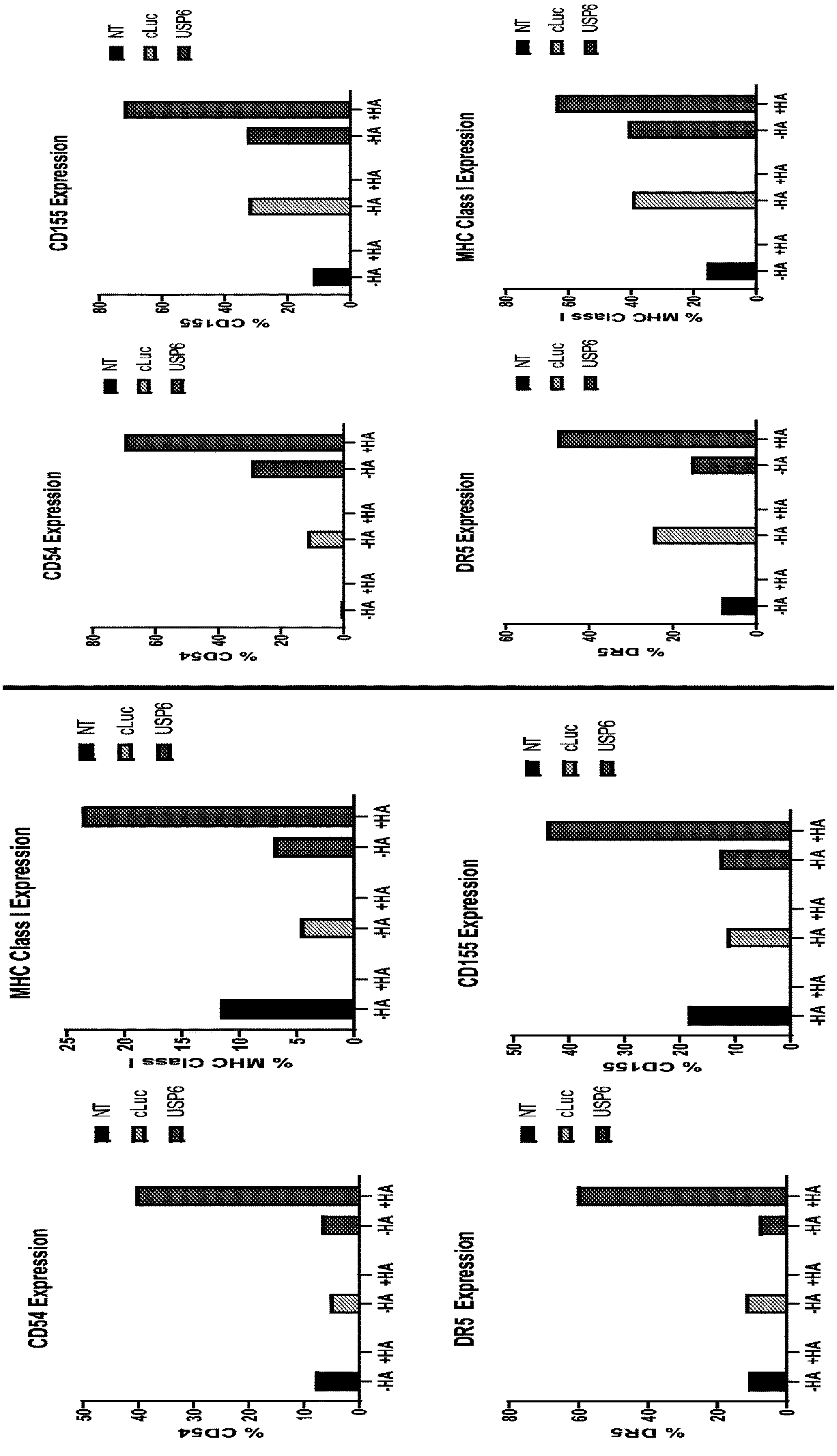
FIG. 28 provides graphs of the percentage of cells expressing surface MHC Class I, DR5, CD155, and CD54 in U937 (left) or THP-1 (right) cells transfected with cLuc or USP6 mRNA. Cells were sorted as USP6− (HA−) or USP6+ (HA+). NT: not transfected.

It was also determined with USP6 mRNA can also upregulate anti-tumor surface markers on AML cells. AML cells (U937 and THP-1) were transfected with either cLuc or USP6 mRNA and surface expression of anti-tumor surface markers such as DR5, CD155, MHC Class I, and CD54 were analyzed by flow cytometry by dividing the sample into HA− and HA+ populations (USP6− and USP6+). As seen in FIG. 28, strong, specific upregulation of key anti-tumor surface receptors was observed only in USP6+ cells.

Figure 29:
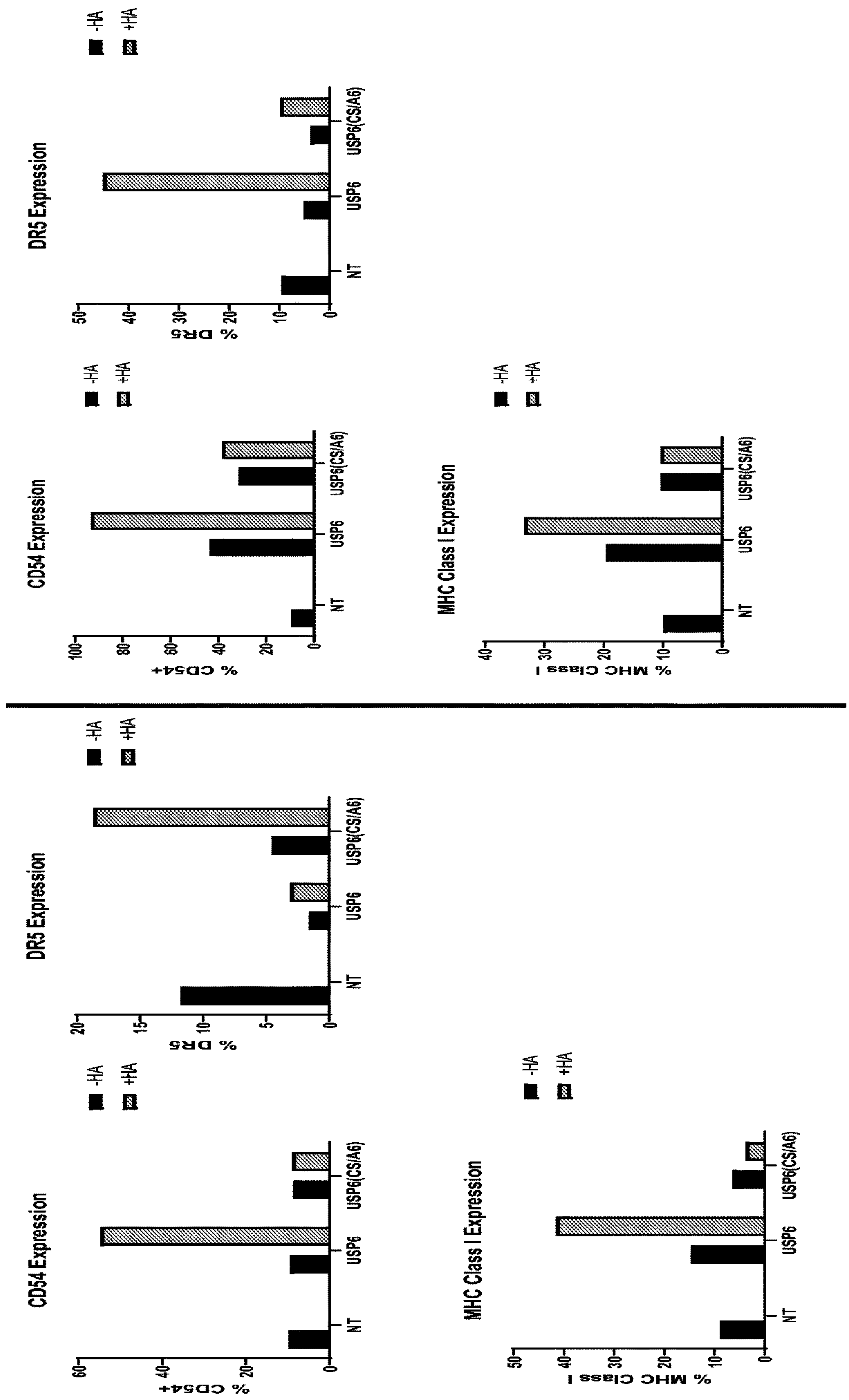
FIG. 29 provides graphs of the percentage of cells expressing surface MHC Class I, DR5, and CD54 in NB4 (left) or U937 (right) cells transfected with USP6(CS/A6−) or USP6 mRNA. Cells were sorted as USP6− (HA−) or USP6+ (HA+). NT: not transfected.

In further experiments, AML cells were transfected with either USP6 mRNA or the inactive USP6(CS/A6−) mutant as a control. Anti-tumor surface receptors were analyzed in the USP6−/+ populations as above. As seen in FIG. 29, strong, specific upregulation of key anti-tumor surface receptors was observed in USP6+ cells, but not the inactive USP6(CS/A6−) mutant, with the exception of DR5 in the NB4 cells.

Figure 30:
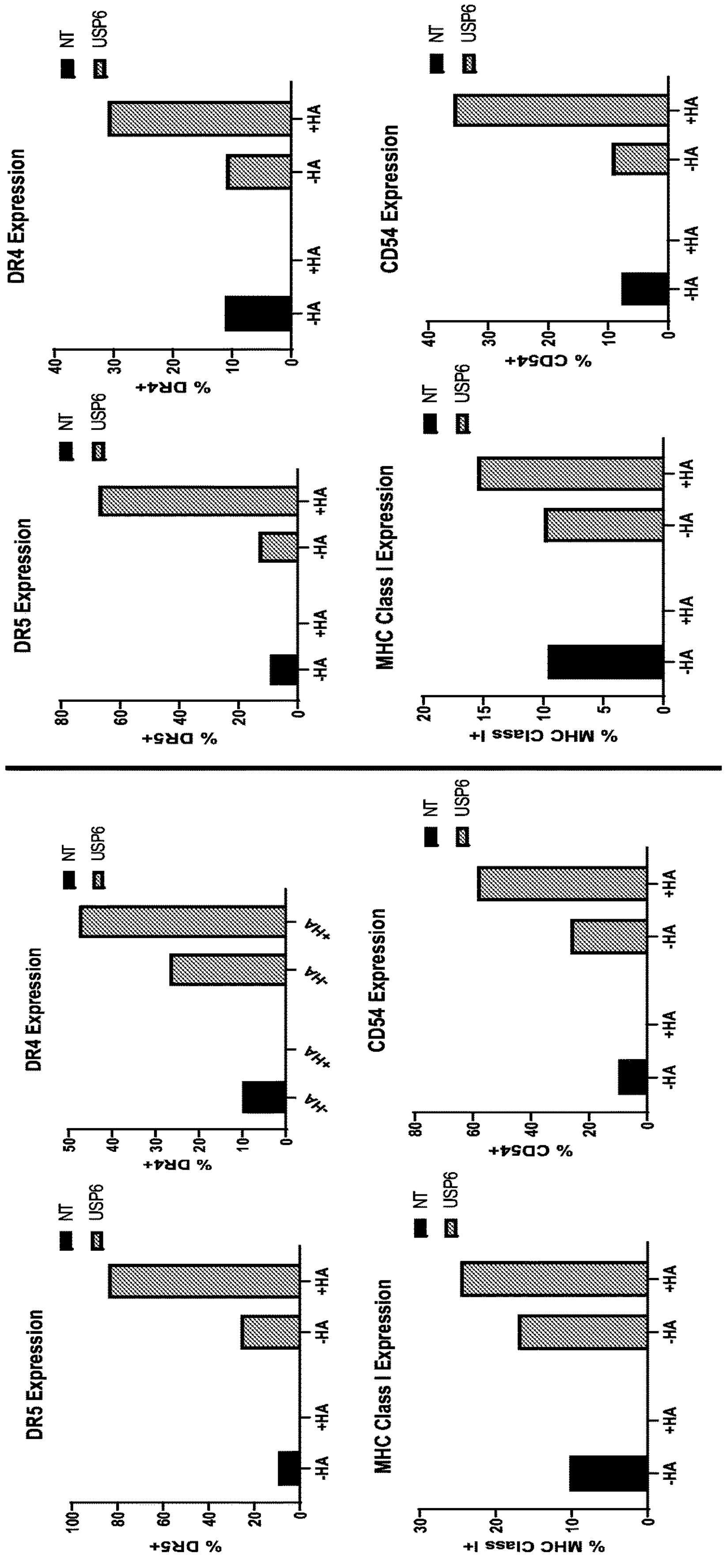
FIG. 30 provides graphs of the percentage of cells expressing surface MHC Class I, DR5, DR4, and CD54 in HeLa (left) or A673 (right) cells transfected with USP6 mRNA. Cells were sorted as USP6− (HA−) or USP6+ (HA+). NT: not transfected.

Additionally, the cell lines HeLa and A673 were transfected with lead USP6 mRNA. Anti-tumor surface receptors were analyzed in the USP6−/+ populations as above. As seen in FIG. 30, strong, specific upregulation of key anti-tumor surface receptors was observed only in USP6+ cells and in both cell lines.

Figure 31A:
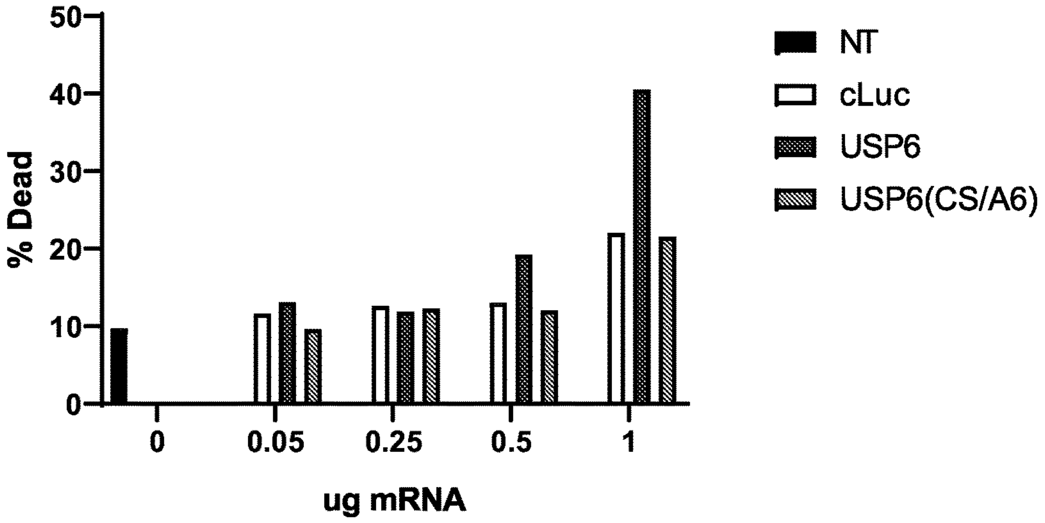
FIGS. 31A-31C provide graphs of the percentage of dead cells of HeLa (FIG. 31A), A673 (FIG. 31B), and THP-1 (FIG. 31C) transfected with USP6 mRNA, cLuc mRNA, or USP6(CS/A6−) mRNA. NT: not transfected.
Figure 31B:
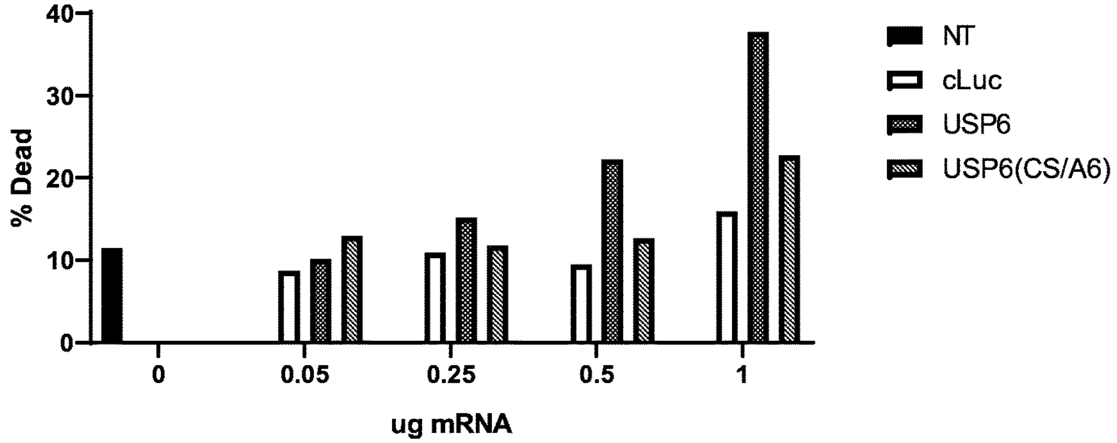
Figure 31C:
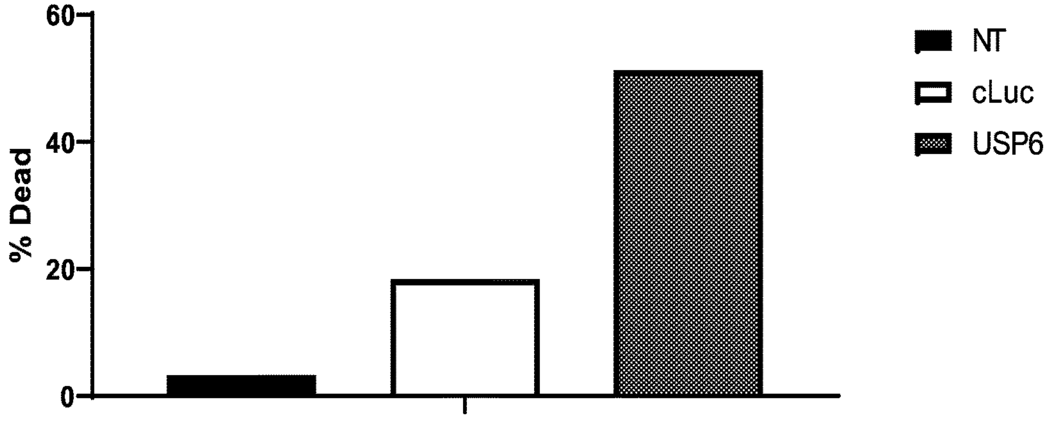

USP6 can sensitize cancer cells to interferon (IFN) cytotoxicity and TRAIL, a potent pro-apoptotic ligand. Due to the upregulation of key death receptors by USP6, it was tested whether USP6 mRNA could selectively induce death in cancer cell lines. HeLa, A673, and THP-1 cell lines were transfected with USP6 or control mRNA (cLuc or USP6 (CS/A6−)) and then the cells were monitored for death by annexin staining. As seen in FIG. 31, USP6 mRNA selectively induces death in several distinct cancer cell lines. These results expand upon the data provided in FIG. 17.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of treating cancer in a subject in need thereof, said method comprising administering to said subject an agent which increases ubiquitin-specific protease 6 (USP6) protein levels, wherein said agent is a USP6 encoding nucleic acid molecule, wherein said cancer forms a tumor, wherein said cancer is Ewing sarcoma or acute myeloid leukemia, and wherein said agent is administered intratumorally and/or to the tumor site.

2. The method of claim 1, wherein said agent is administered as a composition further comprising a pharmaceutically acceptable carrier.

3. The method of claim 1, wherein said agent is administered intratumorally.

4. The method of claim 1, wherein said USP6 encoding nucleic acid molecule is an mRNA.

5. The method of claim 4, wherein said USP6 encoding nucleic acid molecule is an in vitro transcribed USP6 mRNA.

6. The method of claim 4, wherein said mRNA comprises a 5' cap.

7. The method of claim 6, wherein said 5' cap is an anti-reverse cap analogue (ARCA).

8. The method of claim 4, wherein said mRNA comprises a polyadenylate tail.

9. The method of claim 8, wherein said polyadenylate tail comprises 100 to 150 adenosines.

10. The method of claim 4, wherein said mRNA comprises at least one pseudouridine and/or 5-methyl cytidine.

11. The method of claim 4, wherein at least 40% of the uridines are substituted with pseudouridines and at least 40% of the cytidines are substituted with 5-methyl cytidines.

12. The method of claim 4, wherein said mRNA comprises an ARCA and a polyadenylate tail of 100 to 150 adenosines, and wherein at least 40% of the uridines are substituted with pseudouridines and at least 40% of the cytidines are substituted with 5-methyl cytidines.

13. The method of claim 1, further comprising the administration of an immunotherapy.

14. The method of claim 13, further comprising the administration of interferon (IFN).

15. The method of claim 14, wherein the IFN is IFNβ.

16. The method of claim 1, wherein said agent is contained within a lipid nanoparticle, optionally comprising a targeting moiety or a nanobody.

17. The method of claim 1, wherein said agent is administered intratumorally, and wherein said USP6 encoding nucleic acid molecule is an mRNA.

18. The method of claim 17, wherein said agent is contained within a lipid nanoparticle, optionally comprising a targeting moiety or nanobody.

19. The method of claim 1, wherein said cancer is Ewing sarcoma.

20. The method of claim 1, wherein said cancer is acute myeloid leukemia.

* * * * *